US010131626B2

(12) United States Patent
Wagner et al.

(10) Patent No.: US 10,131,626 B2
(45) Date of Patent: Nov. 20, 2018

(54) 3-ARYL PROPIOLONITRILE COMPOUNDS FOR THIOL LABELING

(71) Applicants: UNIVERSITE DE STRASBOURG, Strasbourg (FR); CENTRE NATIONAL DE LA RECHERCHE SCIENTIFIQUE, Paris (FR)

(72) Inventors: Alain Wagner, Strasbourg (FR); Oleksandr Koniev, Strasbourg (FR)

(73) Assignees: UNIVERSITE DE STRASBOURG, Strasbourg (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/480,420

(22) Filed: Apr. 6, 2017

(65) Prior Publication Data
US 2017/0210700 A1    Jul. 27, 2017

Related U.S. Application Data

(62) Division of application No. 14/899,883, filed as application No. PCT/EP2014/064387 on Jul. 4, 2014, now Pat. No. 9,663,454.

(30) Foreign Application Priority Data

Jul. 4, 2013   (EP) ..................................... 13305950

(51) Int. Cl.
| C07K 16/00 | (2006.01) |
|---|---|
| C07C 255/34 | (2006.01) |
| C07K 1/13 | (2006.01) |
| C07C 255/37 | (2006.01) |
| C07C 255/42 | (2006.01) |
| C07C 255/44 | (2006.01) |
| C07C 255/41 | (2006.01) |
| C07C 255/35 | (2006.01) |
| C07C 309/42 | (2006.01) |
| C07D 249/06 | (2006.01) |
| C07C 331/28 | (2006.01) |
| C07C 335/22 | (2006.01) |
| C07C 271/16 | (2006.01) |
| C07C 275/42 | (2006.01) |
| C07C 271/28 | (2006.01) |
| C07F 7/08 | (2006.01) |
| C07C 271/22 | (2006.01) |
| C07D 495/04 | (2006.01) |
| C07F 9/54 | (2006.01) |
| C07D 207/452 | (2006.01) |
| C07D 207/46 | (2006.01) |
| C07D 337/04 | (2006.01) |
| C07D 409/12 | (2006.01) |
| C07D 405/12 | (2006.01) |
| C07D 265/38 | (2006.01) |
| C07D 403/12 | (2006.01) |
| C07C 323/42 | (2006.01) |
| C07D 311/82 | (2006.01) |
| C07C 323/60 | (2006.01) |
| C07K 16/32 | (2006.01) |
| C12N 9/36 | (2006.01) |

(52) U.S. Cl.
CPC .......... *C07C 255/34* (2013.01); *C07C 255/35* (2013.01); *C07C 255/37* (2013.01); *C07C 255/41* (2013.01); *C07C 255/42* (2013.01); *C07C 255/44* (2013.01); *C07C 271/16* (2013.01); *C07C 271/22* (2013.01); *C07C 271/28* (2013.01); *C07C 275/42* (2013.01); *C07C 309/42* (2013.01); *C07C 323/42* (2013.01); *C07C 323/60* (2013.01); *C07C 331/28* (2013.01); *C07C 335/22* (2013.01); *C07D 207/452* (2013.01); *C07D 207/46* (2013.01); *C07D 249/06* (2013.01); *C07D 265/38* (2013.01); *C07D 311/82* (2013.01); *C07D 337/04* (2013.01); *C07D 403/12* (2013.01); *C07D 405/12* (2013.01); *C07D 409/12* (2013.01); *C07D 495/04* (2013.01); *C07F 7/0818* (2013.01); *C07F 9/5442* (2013.01); *C07K 1/13* (2013.01); *C07K 16/32* (2013.01); *C12N 9/2462* (2013.01); *C12Y 302/01017* (2013.01); *C07C 2602/24* (2017.05); *C07K 2317/24* (2013.01)

(58) Field of Classification Search
None
See application file for complete search history.

(56) References Cited

U.S. PATENT DOCUMENTS

2009/1026384       10/2009   Anderson et al.
2011/0152234 A1    6/2011    Faull et al.

FOREIGN PATENT DOCUMENTS

WO    WO 2013067084    *    5/2013

OTHER PUBLICATIONS

Estarellas, et al, "Theoretical Study on Cooperativity Effects between Anion-[pi] and Halogen-Bonding Interactions" *Chemphyschem*, Oct. 24, 2011, pp. 2742-2750, vol. 12, No. 15.
Furstner, et al. "Platinum-Catalyzed Cycloisomerization Reactions of Enynes" *J. Am. Chem. Soc.*, 2001, pp. 11863-11869, vol. 123.
Govindappa, et al. "Synthesis of 3,5-diaryl-isoxazole-4-carbonitriles and their efficacy as antimicrobial agents" *Der Pharma Chemica*, Jan. 1, 2012, pp. 2283-2287.
Kim, et al. "One-pot synthesis of conjugated alkynenitriles from aldehydes" *Tetrahedron Letters*, Mar. 15, 2007, pp. 2299-2301, vol. 48, No. 13.

(Continued)

*Primary Examiner* — Ana Z Muresan
(74) *Attorney, Agent, or Firm* — Saliwanchik, Lloyd & Eisenschenk

(57) ABSTRACT

The present invention relates to a process for labeling compounds comprising thiol moieties with 3-arylpropiolonitrile compounds, to 3-arylpropiolonitrile compounds substituted with tag moieties and to specific 3-arylpropiolonitrile linkers.

2 Claims, 16 Drawing Sheets

(56) References Cited

OTHER PUBLICATIONS

Koniev, et al. "Selective Irreversible Chemical Tagging of Cysteine with 3-Arylpropiolonitriles" *Bioconjugate Chemistry*, Feb. 19, 2014, pp. 202-206, vol. 25, No. 2.

Lacy, et al. "Post-Cycloaddition-Retroelectrocyclization Transformations of Polycyanobutadienes" *European Journal of Organic Chemistry*, Feb. 17, 2013, pp. 869-879, vol. 2013, No. 5.

Lucas, et al. "Substituent Effects in Ion-[pi] Interactions: Fine-Tuning via the Ethyl Group" *The Journal of Physical Chemistry A*, Feb. 4, 2010, pp. 1926-1930, vol. 114, No. 4.

McIntosh, et al. "Synthesis and Computational Analysis of Densely Functionalized Triazoles Using o-Nitrophenylalkynes" *The Journal of Organic Chemistry*, Jan. 20, 2012, pp. 1101-1112, vol. 77, No. 2.

Tancini, et al. "1,1-Dicyano-4-[4-(diethylamino)phenyl]buta-1,3dienes: Structure-Property Relationships" *European Journal of Organic Chemistry*, Mar. 22, 2012, pp. 2756-2765, vol. 2012, No. 14.

Trofimov, et al. "Synthesis of Functionalized I-Cysteine and I-Methionine by Reaction with Electron-Deficient Acetylenes" *Synthesis*, Jul. 10, 2009, pp. 3136-3142, vol. 2009, No. 18.

Wang, et al. "Copper-Catalyzed Oxidative Transformation of Aryl Propargylic Azides to Aryl Propiolonitriles" *Advanced Synthesis & Catalysts*, Apr. 8, 2013, pp. 1207-1210, vol. 355, No. 6.

Weber, et al. "Mollisianitrile, a New Antibiotic from *Mollisia* sp. A59 96" Retrieved from the Internet: URL:http://www.znaturforsch.com/ac/v62c/s62c8567.pdf.

Fernández-Suárez, M. et al, "Fluorescent probes for super-resolution imaging in living cells" *Molecular Cell Biology*, Dec. 2008, pp. 929-943, vol. 9.

Koniev, O. et al, "MAPN: First-in-Class Reagent for Kinetically Resolved Thiol-to-Thiol Conjugation" *Bioconjugate Chemistry*, 2015, pp. A-E.

\* cited by examiner

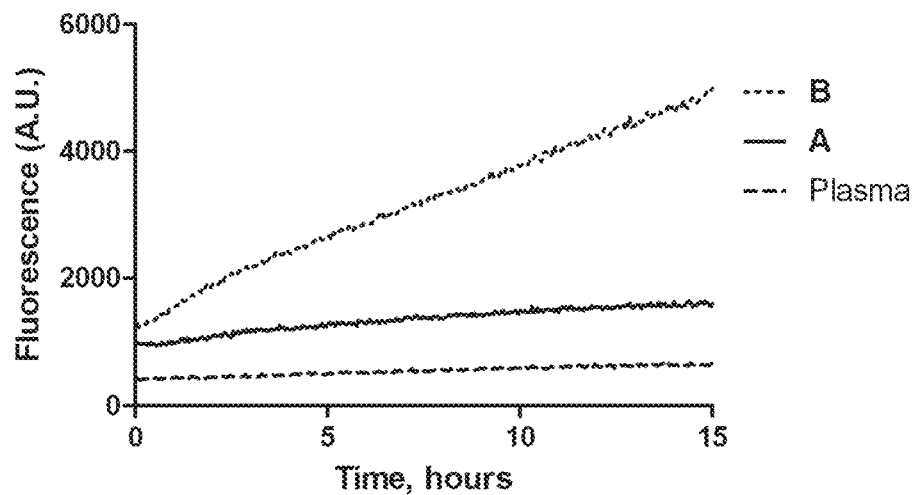
Figure 1
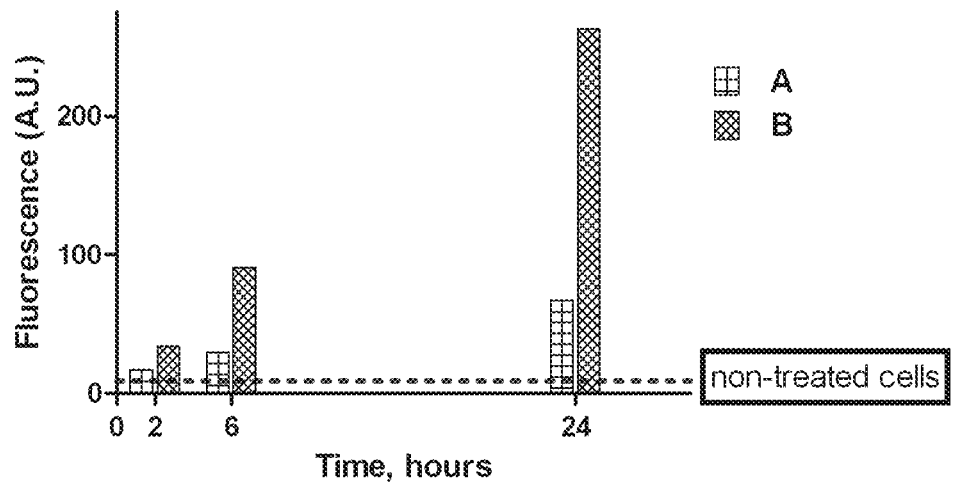
Figure 2a
| Time (hours) | 2 | 6 | 24 |
|---|---|---|---|
| Ratio (B/A) | 2,0 | 3,1 | 3,9 |
Figure 2b Maleimide    Compound of the invention Maleimide    Compound of the invention

3-ARYL PROPIOLONITRILE COMPOUNDS FOR THIOL LABELING

CROSS REFERENCE TO RELATED APPLICATIONS

This application is a divisional of U.S. application Ser. No. 14/899,883, filed Dec. 18, 2015, which is the National Stage of International Application No. PCT/EP2014/064387, filed on Jul. 4, 2014, which claims the benefit of European Application No. 13305950.1, filed Jul. 4, 2013. The contents of which are hereby incorporated by reference in their entirety.

The present invention relates to a process for labeling compounds comprising thiol moieties with 3-arylpropiolonitrile compounds, to 3-arylpropiolonitrile compounds substituted with tag moieties and to specific 3-arylpropiolonitrile linkers.

BACKGROUND OF THE INVENTION

Over 90% of the human proteins contain cysteines, while in silico digest of the human proteome revealed that only about 15% of all human tryptic peptides detectable by mass spectroscopy (MS) contain at least one cysteine in their sequence. This observation combined with the presence of a highly reactive thiol group on its side chain makes cysteine an attractive target for chemical labeling. Cysteine is the only coded amino acid that carries a nucleophilic sulfhydryl (or thiol) group (—SH), which largely exceeds the reactivity of any other nucleophilic function susceptible to be present in proteins. As a result, chemospecific cysteine derivatization is by far the most widely used method for chemical tagging of proteins. Among the vast number of chemical cysteine modification methods reported in literature so far, reagents such as N-substituted maleimides, 4-vinylpyridines and iodoacetamides are most commonly used. All of them possess drawbacks preventing them from being ideal methodology for cysteine labeling, though being suited for this task. These drawbacks are mainly presence of undesired side reactions, in particular for iodoacetamides and maleimides, and instability of addition product in biological environments due to reversible thiol exchange and other side reactions.

The present invention relates to a process for labeling compounds comprising at least one thiol moiety, such as cysteine, with compounds comprising a tag moiety and a 3-arylpropiolonitrile moiety. Said compounds and their addition products with cysteine derivatives show an unexpected stability in a wide range of conditions. The process for labeling compounds comprising thiol moieties of the invention can thus be used for a wide range of applications.

SUMMARY OF THE INVENTION

The first object of the invention is a process for the preparation of a labelled compound comprising a thiol moiety, comprising contacting a compound comprising a thiol moiety with a compound of formula (I)

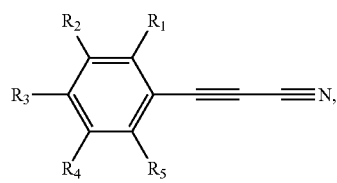

wherein $R_1$ to $R_5$ are as described below, and wherein at least one of $R_1$ to $R_5$ comprises a tag moiety.

Another object of the invention is a compound of formula (I)

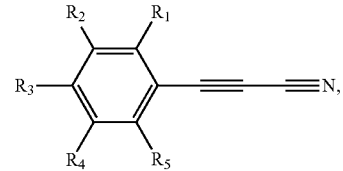

wherein $R_1$ to $R_5$ are as defined below, and wherein at least one of $R_1$ to $R_5$ comprises a tag moiety.

Another object of the invention is a compound of formula (II)

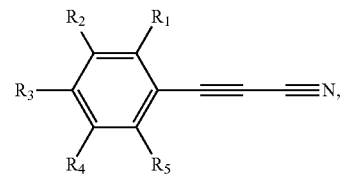

wherein $R_1$ to $R_5$ are as defined below, and wherein at least one of $R_1$ to $R_5$ is different from a hydrogen atom.

Another object of the invention is a compound of formula (III)

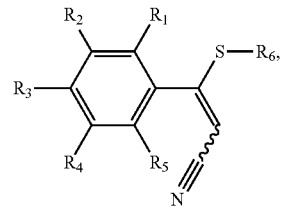

wherein $R_6$—S corresponds to the moiety of the compound comprising at least one thiol moiety as identified above.

BRIEF DESCRIPTION OF THE FIGURES

FIG. 1: Evolution of intensity of fluorescence over time obtained in human plasma for the same concentration of compounds A and B.

FIG. 2a-2c: a) Evolution of intensity of fluorescence over time obtained in cellulo for the same concentration of compounds A and B.
  b) Intensity ratio compound B/compound A at different times in cellulo.
  c) Microscope pictures of cells treated with compounds A and B, superimposition of TAMRA and Hoechst labeling. White spots around nucleus correspond to hydrolyzed probe. A—arylpropiolonitrile probe, B—maleimide probe.

FIG. 3a-3b: HPLC monitoring of the hydrolysis of phenylmaleimide (2) in PBS (1×, pH 7.6) at 1 mM concentration at 25° C.; the peaks correspond, from the earliest to the latest, to

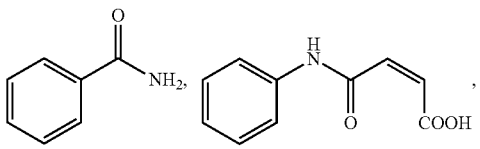

and 2

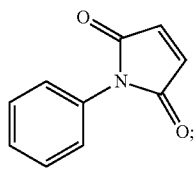 [SMILES: O=C1C=CC(=O)N1c1ccccc1]

conversion was monitored by disappearance of the starting material (a). Pseudo first order rate constant for the reaction was determined by plotting the ln([phenylmaleimide]) versus time and analyzing by linear regression. The constant corresponds to the absolute value of determined slope (b).

Figure 4:
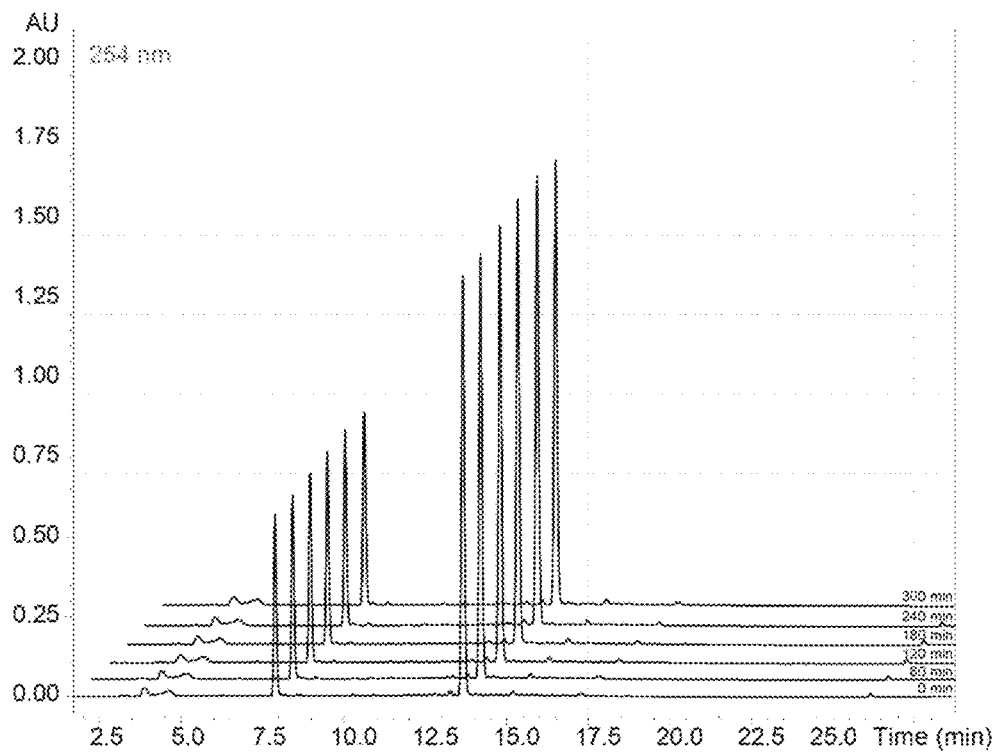

FIG. 4: HPLC monitoring of hydrolytic stability of N-(4-(cyanoethynyl)phenyl)acetamide (pNHAc-APN, 11) in PBS (1×, pH 7.6) at 1 mM concentration at 25° C. Conversion was monitored by disappearance of the starting material; the peaks correspond, from the earliest to the latest, to

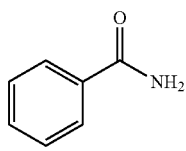

and 11

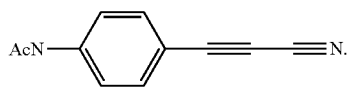

No detectable conversion of arylpropiolonitrile 11 was observed after 5 hours of monitoring.

Figure 5:
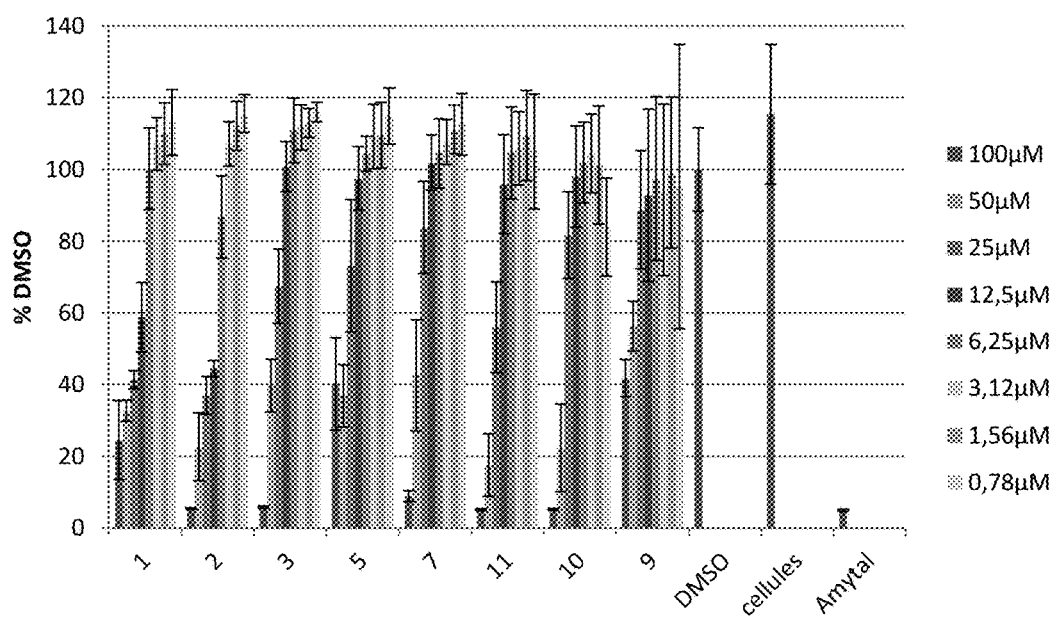

FIG. 5: MTT test results for compounds 1, 2, 3, 5, 7, 11, 10 and 9.

Figure 6A:
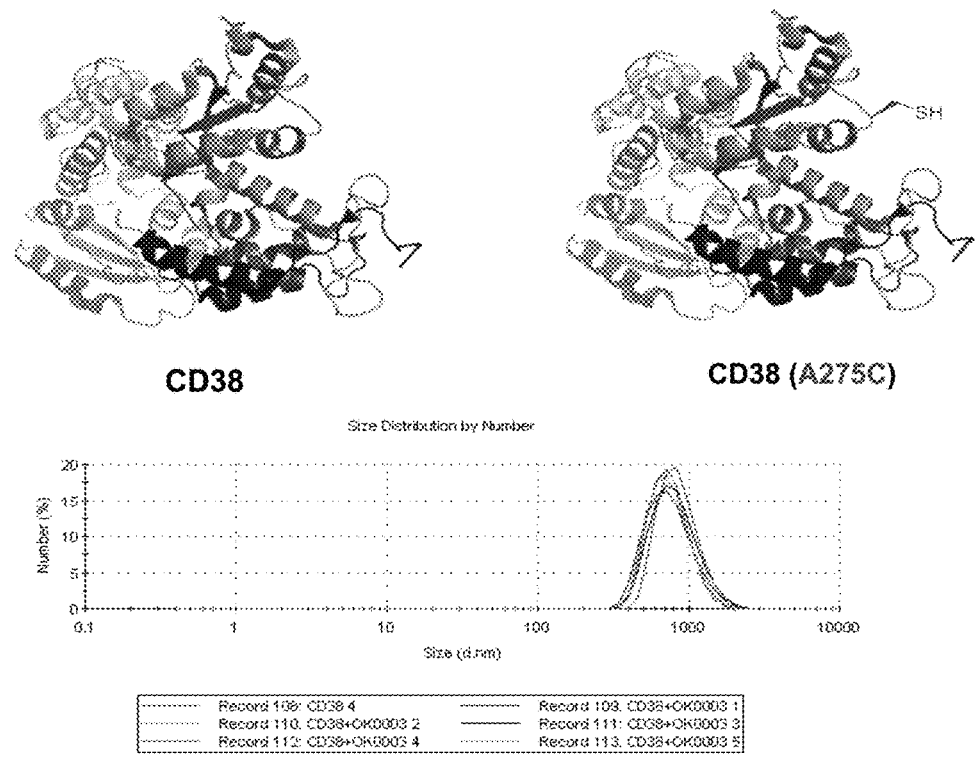
Figure 6B:
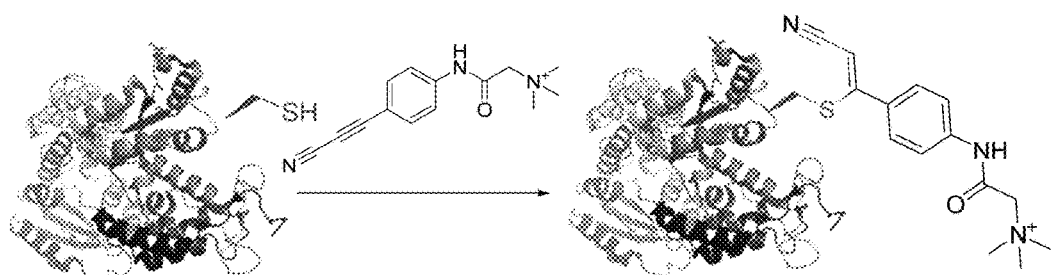
Figure 6C:
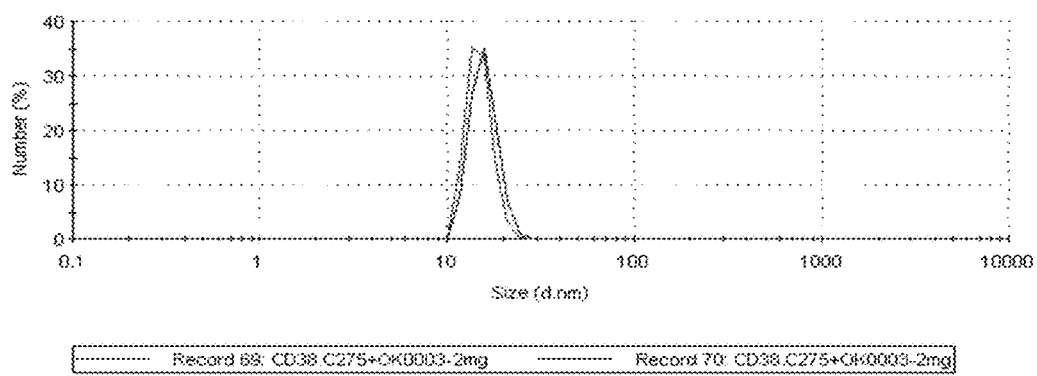

FIG. 6a-6c: a) schematic structure and measured DLS spectra of CD38 and CD38 A275C mutant; b) scheme of CD38 A275C modification with 49; c) DLS (Dynamic Light Scattering) spectrum of the resulting conjugate.

Figure 7A:
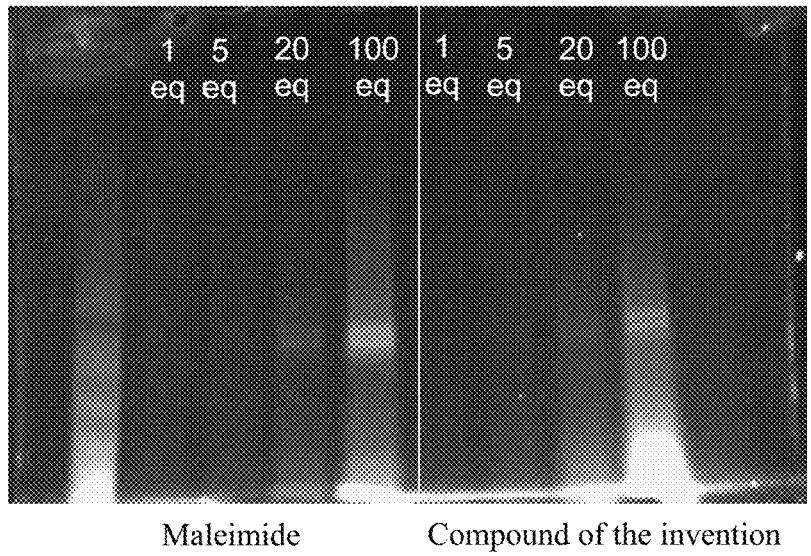
Figure 7B:
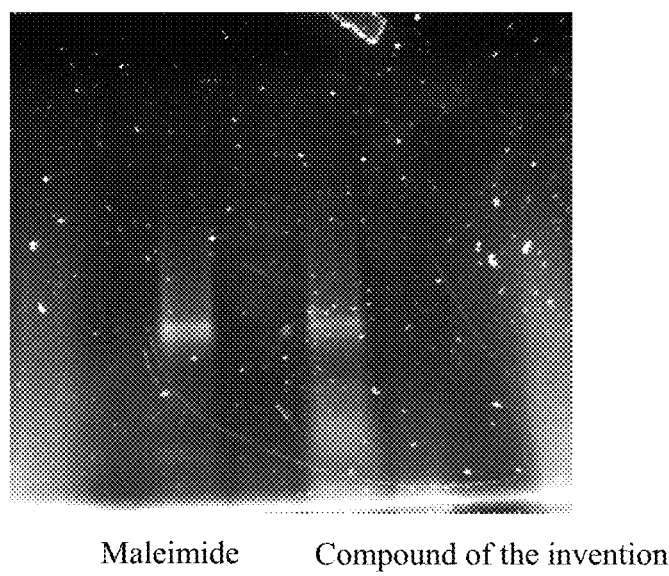

FIG. 7a-7b: Gel electrophoresis of CD38-C375 mutant labeled with a compound according to the invention and with the corresponding maleimide compound, before purification (a) and after purification (b).

Figure 8:
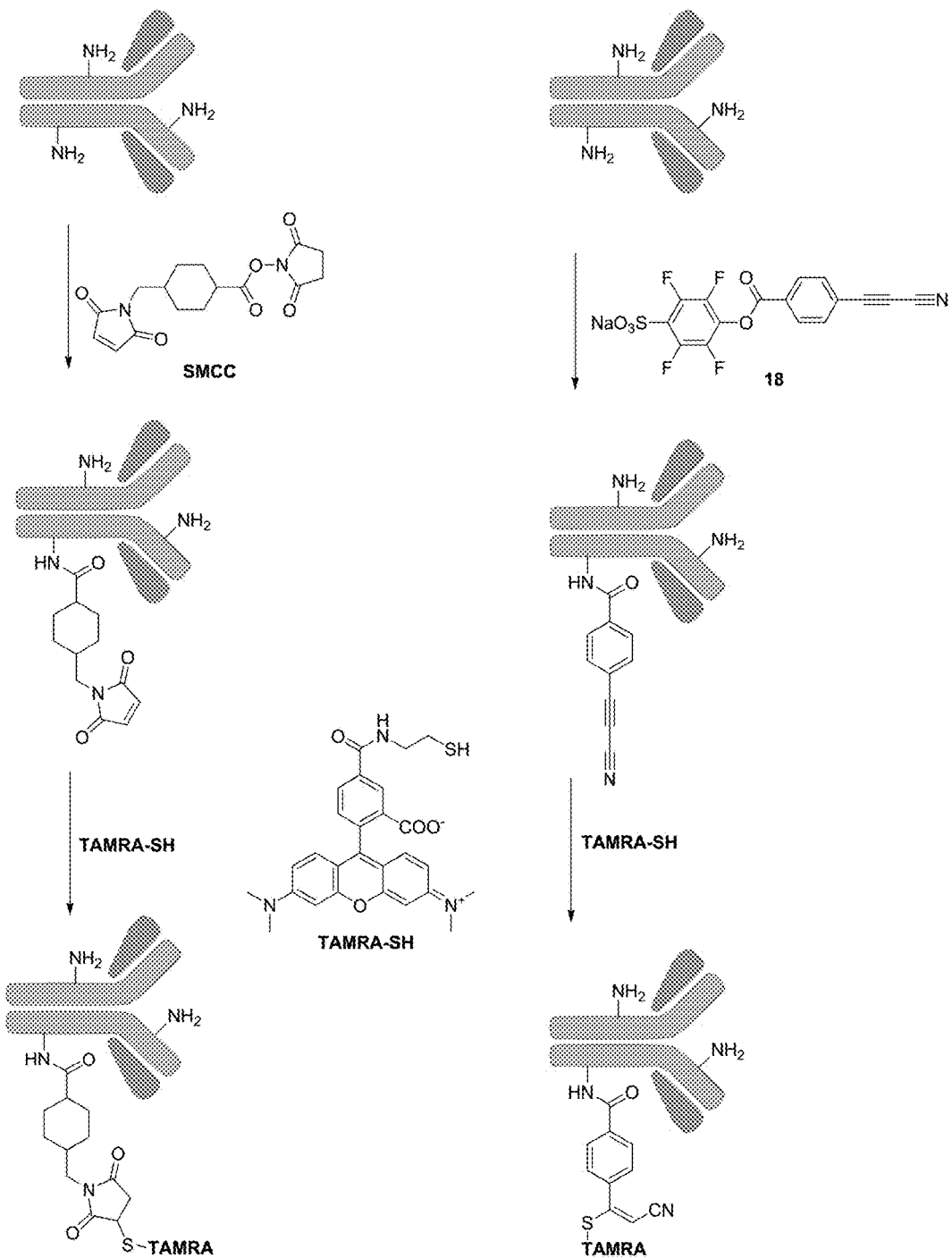

FIG. 8: Strategy of preparation of the antibody-TAMRA conjugate with a compound according to the invention, and the comparison with the corresponding maleimide.

Figure 9:
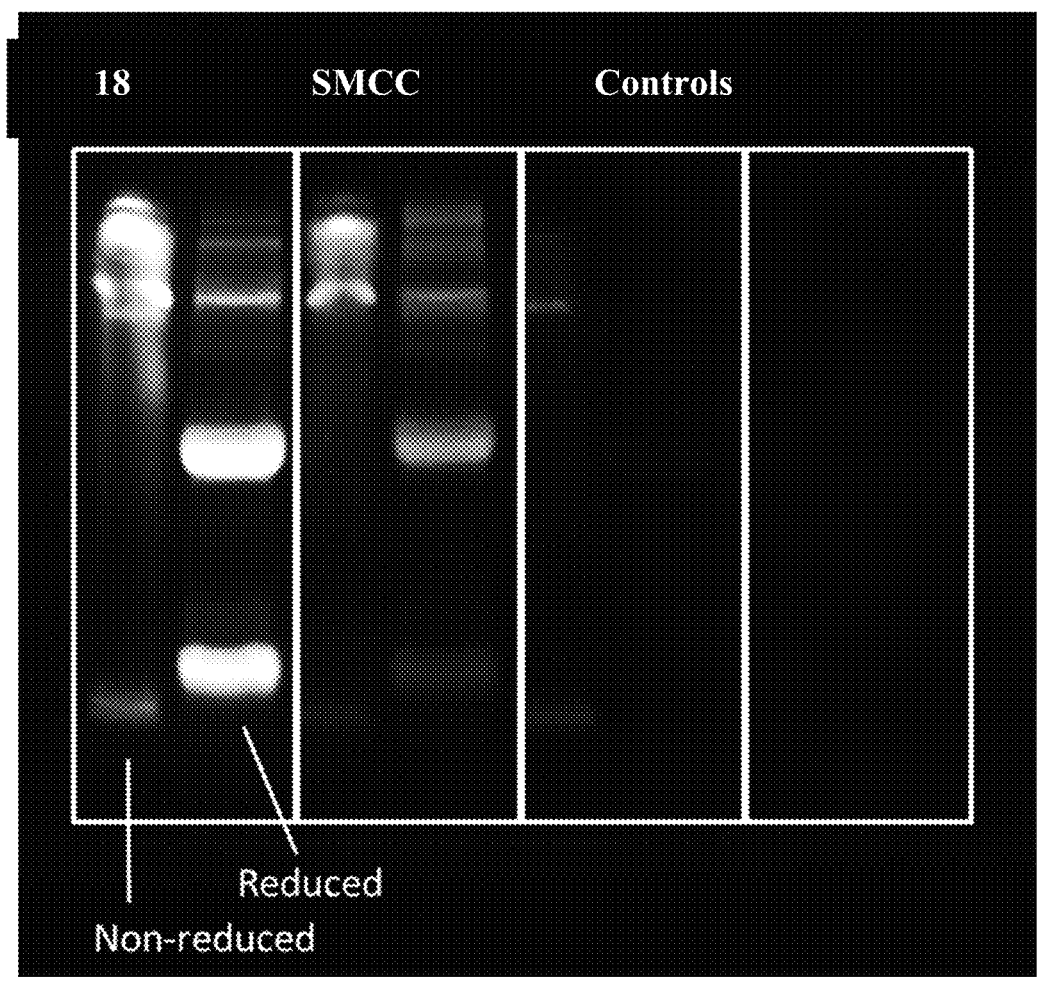

FIG. 9: Gel electrophoresis of the conjugates obtained respectively with the compound according to the invention (CBTF) and with the corresponding maleimide (SMCC).

Figure 10:
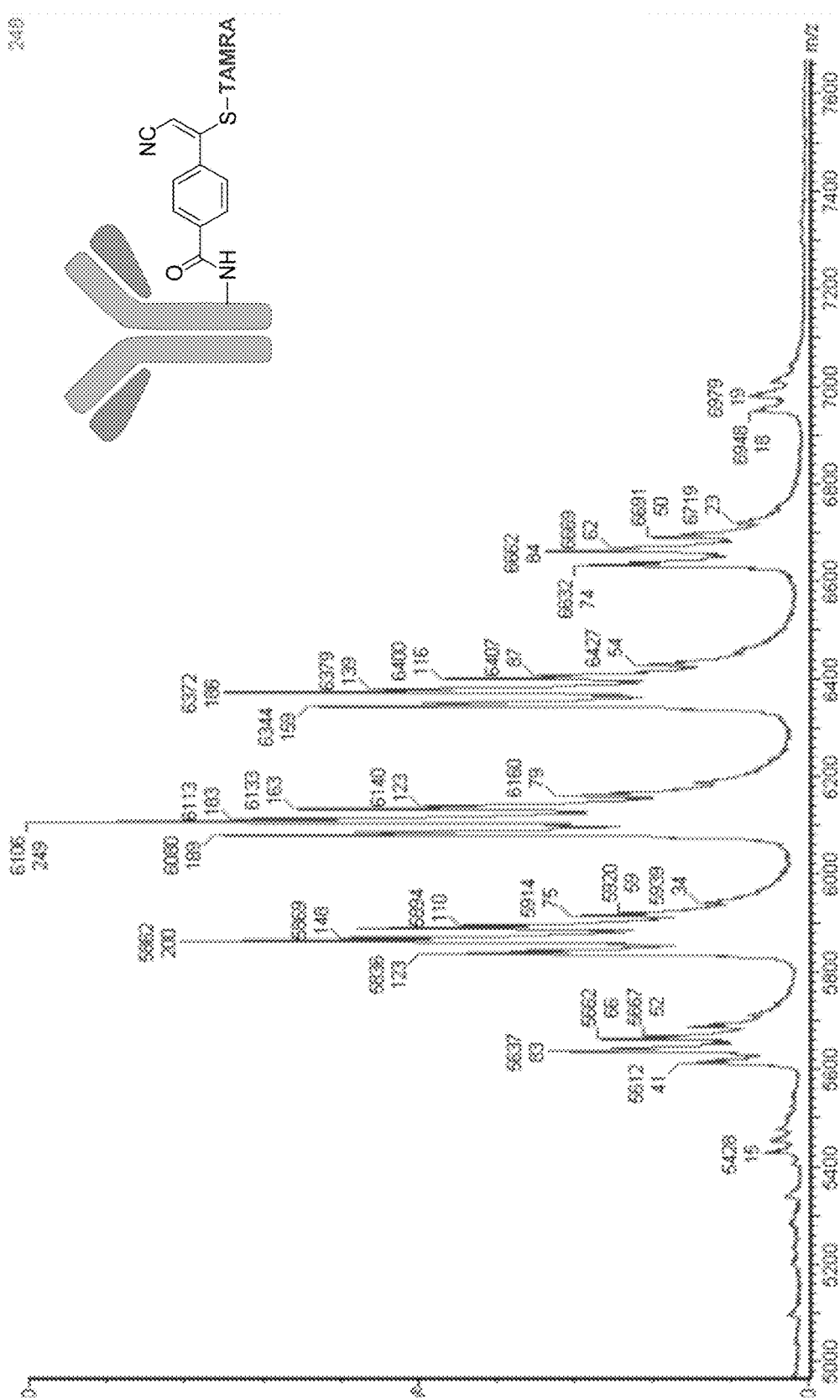

FIG. 10: Mass spectrum for the conjugate obtained with the compound according to the invention.

Figure 11:
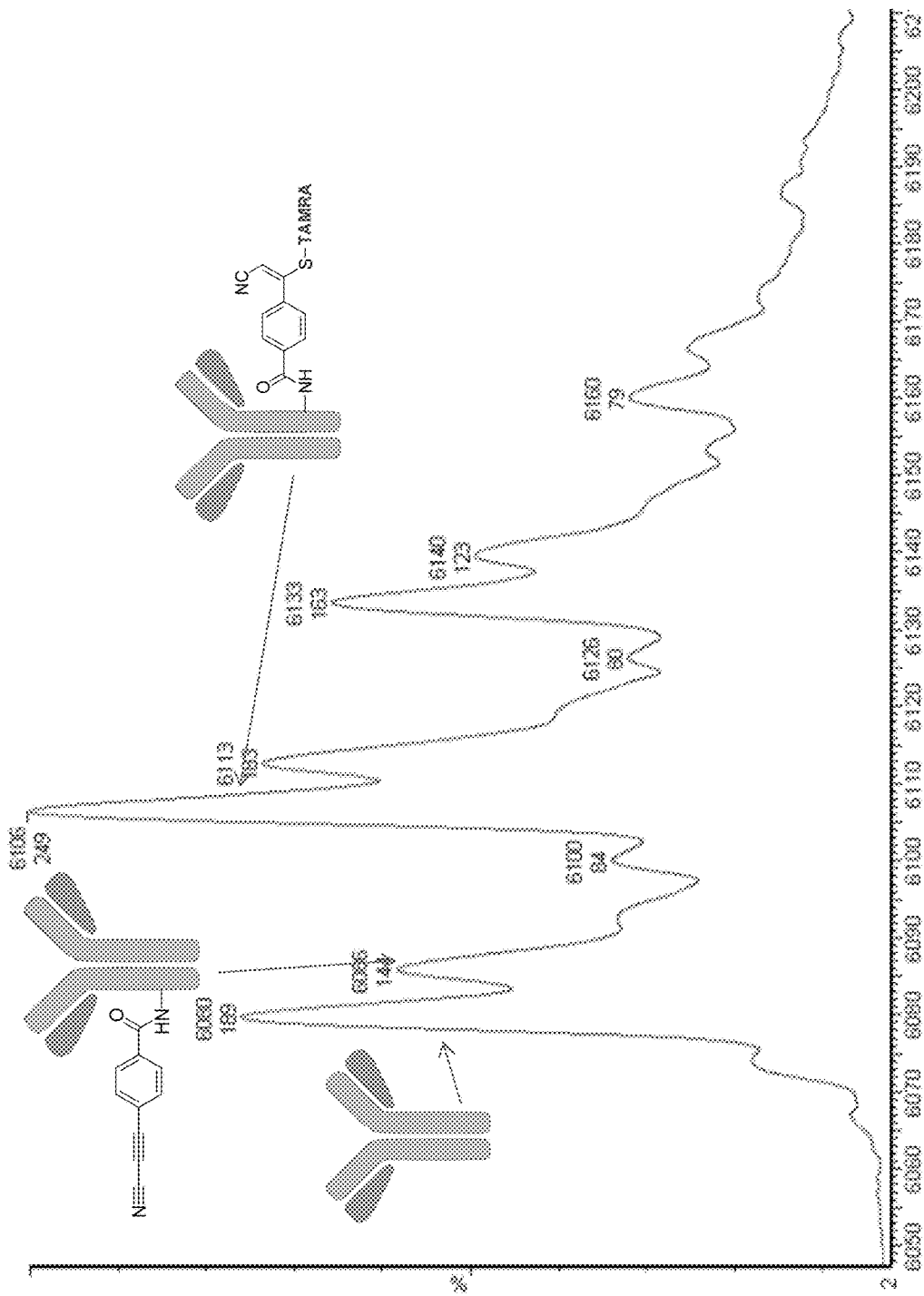

FIG. 11: Zoom on the mass spectrum of FIG. 10.

Figure 12:
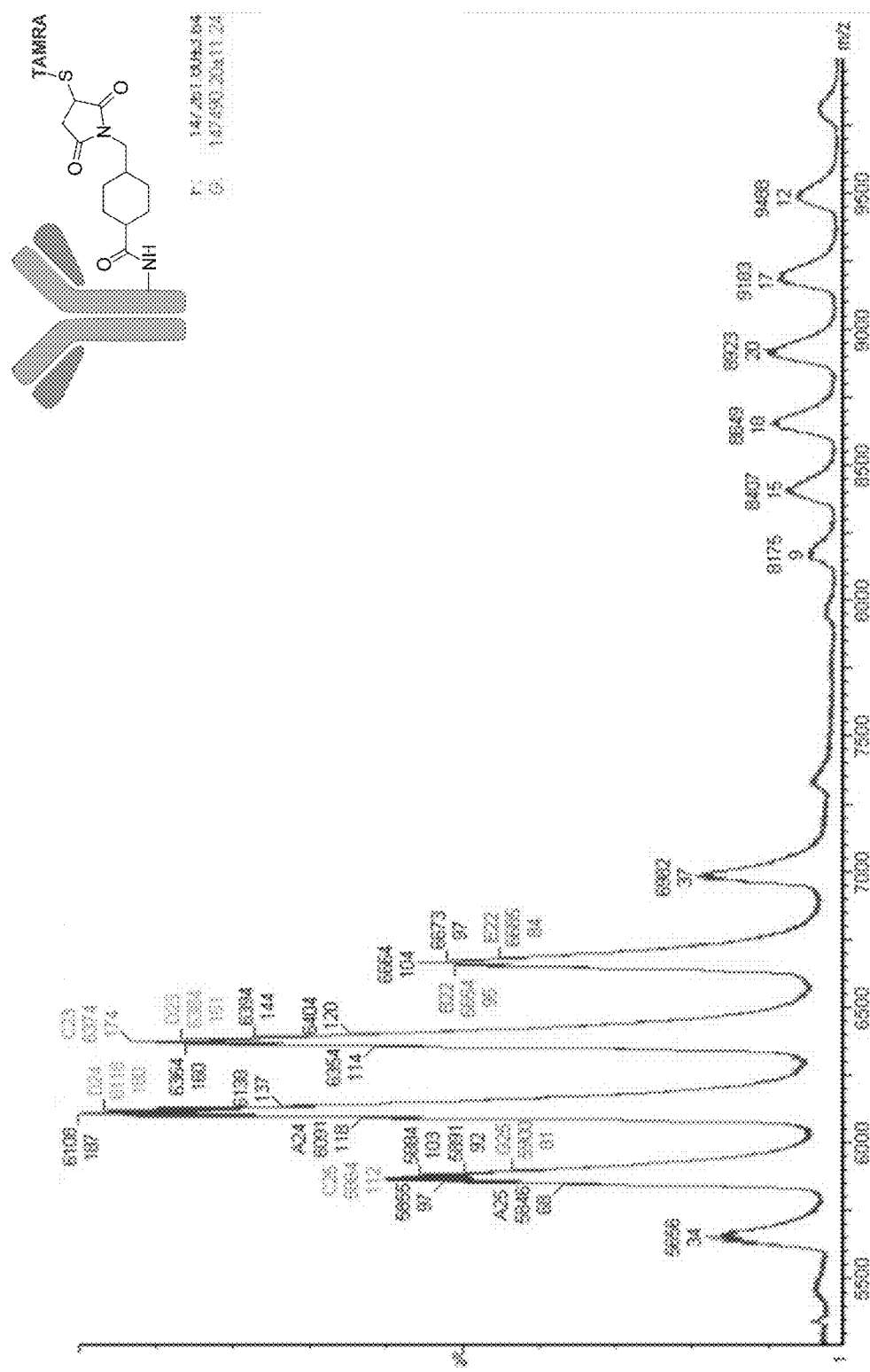

FIG. 12: Mass spectrum obtained with the maleimide.

Figure 13:
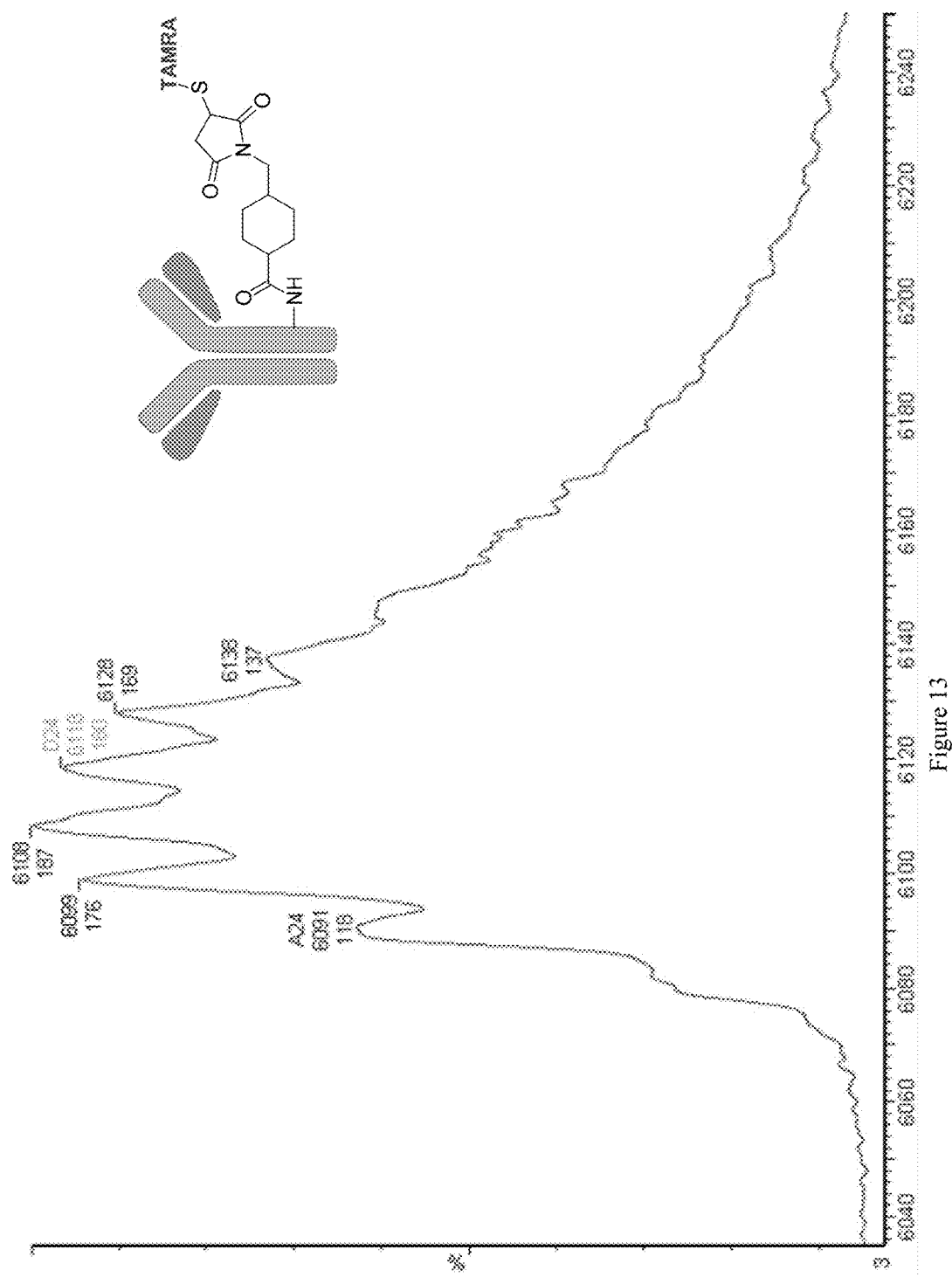

FIG. 13: Zoom on the mass spectrum of FIG. 12.

Figure 14:
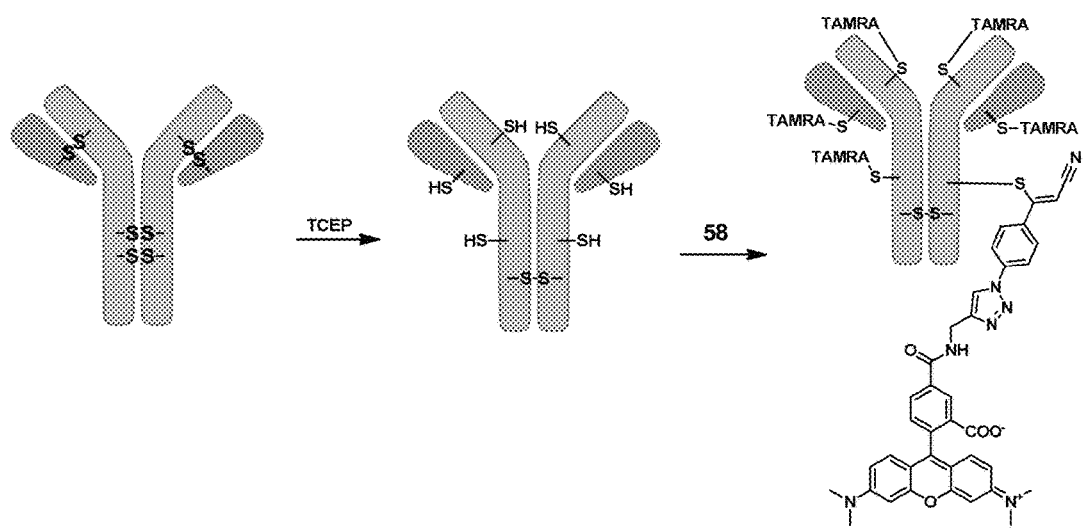

FIG. 14: General scheme of direct conjugation of the compound 58 to partially reduced Trastuzumab.

Figure 15:
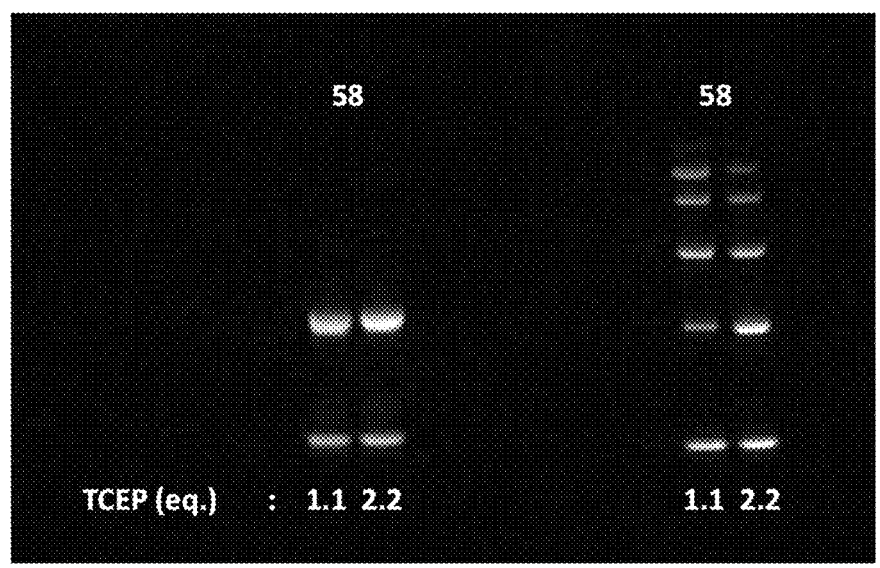

FIG. 15: SDS-PAGE analysis of the obtained conjugates shows that compound 58 is covalently attached to the antibody FIG. 16: General scheme of rebridging of antibody fragments using compounds 33 and 34.

Figure 17:
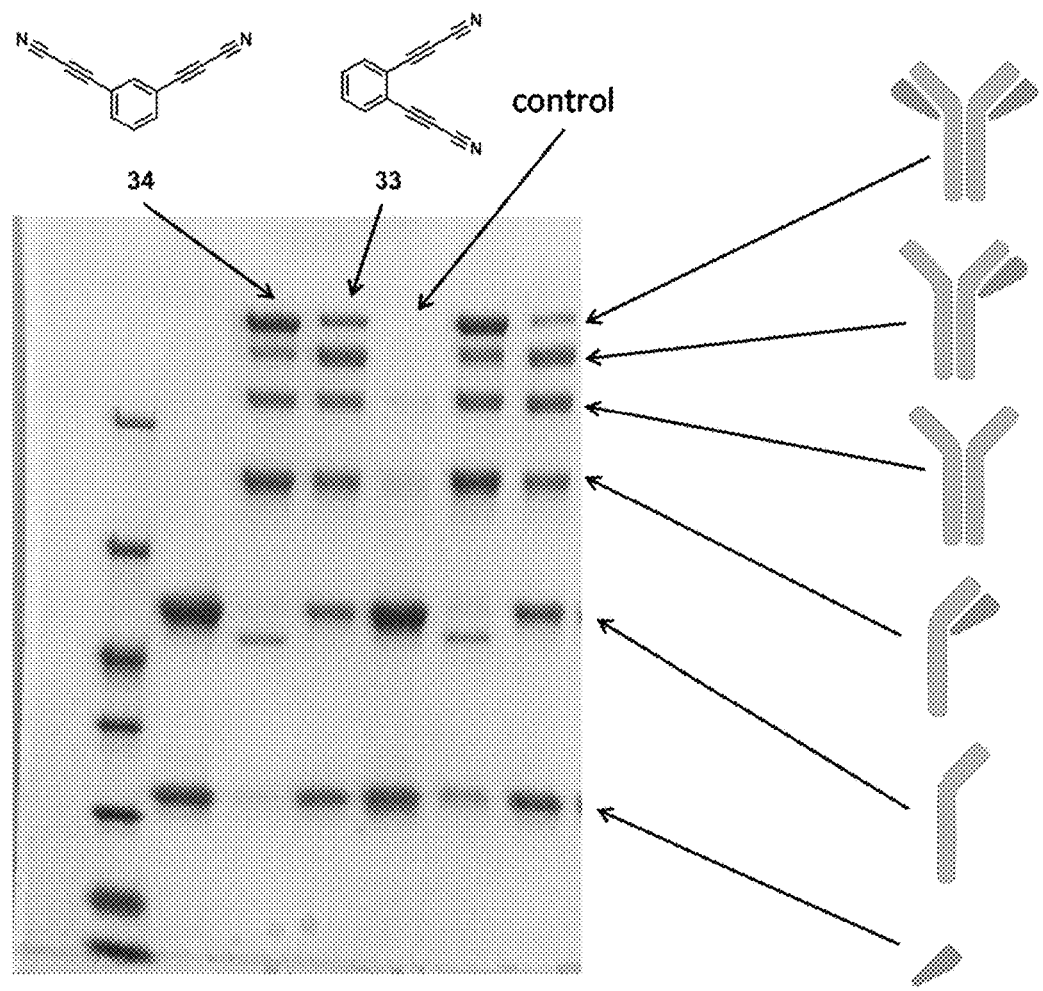

FIG. 17: SDS-PAGE analysis shows that antibody fragments are successfully bridged by compounds 33 and 34.

DETAILED DESCRIPTION OF THE INVENTION

The first object of the invention is a process for the labeling of a compound comprising a thiol moiety, comprising contacting said compound comprising a thiol moiety with a compound of formula (I)

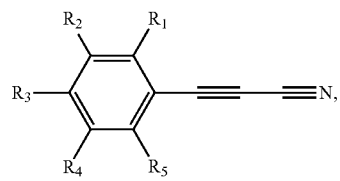

wherein each of $R_1$ to $R_5$ is independently selected in the group consisting of:
hydrogen atoms,
alkyl, alkene or alkyne groups, optionally interrupted by at least one heteroatom selected among O, N and S,
aryl groups,
alkoxy groups,
halogen atoms,
amino (—NRR') groups, wherein R and R' are independently hydrogen atoms, alkyl, alkene, alkyne or aryl groups as defined below,
hydroxylamine (—ONH$_2$) group,
hydrazine (—NH—NH$_2$) group,
nitro (—NO$_2$) group,
azido (—N$_3$) group,
diazonium (—N$_2^+$) group, optionally in presence of a counterion,
maleimide group,
alkyl- or aryl-carboxyl (—C(=O)OR) groups, wherein R is as described above,
alkyl- or aryl-carbonyl (—C(=O)R) groups, wherein R is as described above,
hydroxyl (—OH) group,
boronic acid —B(OR")$_2$ group, wherein R" is a hydrogen atom or an alkyl group,
phosphine or phosphonium groups,
isocyanate (—N=C=O) or isothiocyanate (—N=C=S) group,
chlorosulfonyl (—SO$_2$Cl) group,
a —O—C(=O)—C(N$_2$)—CF$_3$ group or a —C(=O)—C(N$_2$)CF$_3$ group,
activated esters, such as —C(=O)—NHS, wherein NHS stands for N-hydrosuccinimidyl, perfluorinated esters, and acylureas,
a —C≡C—C≡N group,
tags, and
alkyl groups substituted by at least one of the previously listed groups, wherein at least one of $R_1$ to $R_5$ comprises, preferably is, a tag moiety.

Two of $R_1$ to $R_5$ may alternatively form together and with the carbon atoms of the phenyl ring to which they are linked a mono or polycyclic ring, saturated, unsaturated or aromatic, optionally comprising at least one heteroatom such as P, O or S.

The tag moiety that is comprised in the compound of formula (I) may be directly bonded to the phenyl ring. It may also be bonded to the phenyl ring through a "linker" group, such as a COO, a NH—C(=O)—NH, a NH—C(=O)—O, a triazole, or a CONH group. It may also be present as a substituent of one of the $R_1$ to $R_5$ groups as described above.

In a preferred embodiment, $R_3$ comprises, preferably $R_3$ is, a tag moiety.

In the present invention, the term "alkyl" relates to a linear, cyclic or branched hydrocarbon group comprising from 1 to 20 carbon atoms, preferably from 1 to 6 carbon atoms, in particular from 1 to 3 carbon atoms. Among alkyl groups can be cited for instance the methyl, ethyl, n-propyl, isopropyl, n-butyl, sec-butyl, tert-butyl, n-pentyl, n-hexyl and cyclohexyl groups. An alkyl group according to the invention may be interrupted by at least one heteroatom selected from Si, N, O and S. Among alkyl groups interrupted by at least one heteroatom may be cited the polyethyleneglycol groups of formula —(OCH$_2$—CH$_2$)$_n$—OH, wherein n is from 1 to 1000, preferably from 1 to 100, in particular from 1 to 8. An alkyl group according to the invention may be substituted by at least one halogen atom.

The term "alkene" relates to an alkyl group as defined above, further comprising at least one C=C double bond.

The term "alkyne" relates to an alkyl group as defined above, further comprising at least one C≡C triple bond. Among alkyne groups can be cited for instance acetylene and cyclooctyne groups.

The term "alkoxy" relates to an alkyl group as defined above linked to the rest of the molecule via an oxygen atom.

The term "aryl" relates to a group comprising at least one planar ring comprising a conjugated π system made of double bonds and/or non-bonding doublets, wherein each atom of the ring comprises a p orbital, the p orbitals overlay each other, and the delocalization of the π electrons lowers the molecule energy. Preferably, the aryl group is a hydrocarbon aryl group, optionally comprising at least one heteroatom selected from N, O and S. Preferably, an aryl group is selected from the group consisting of phenyl, pyridinyl, pyrimidinyl, pyrazinyl, pyridazinyl, triazinyl, furanyl, thiophenyl, pyrrolyl, imidazolyl, thiazolyl, oxazolyl, isoxazolyl, dihydroisoxasolyl, triazolyl, diazinyl, tetrazinyl, pyrazolyl and naphthyl groups. In particular, an aryl group is selected from the group consisting of isoxazolyl, dihydroisoxasolyl, triazolyl, diazinyl, tetrazinyl and pyrazolyl groups.

The term "halogen" relates to an atom selected from the group consisting of F, Cl, Br and I atoms. Preferably, a halogen is a Cl or Br atom.

The optical and geometrical isomers, racemates, tautomers, salts, hydrates, solvates and mixtures thereof of the compounds are also encompassed by the scope of formulas (I), (II), (III) and (IV) of the present invention.

When the compounds according to the invention are in the forms of salts, they are preferably pharmaceutically acceptable salts. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2. Preferably, the salt does not comprise any thiol moiety.

The "counterion" can be any ion appropriate for compensating the charge of the diazonium group, and may be easily chosen by anyone of ordinary skill in the art. For instance, the counterion may be selected from the group consisting of halogenates, $BF_4^-$, $NO_3^-$, $HSO_4^-$, $PF_6^-$, $CH_3COO^-$, $N(SO_2CF_3)_2^-$, $CF_3SO_3^-$, $CH_3SO_3^-$, $CF_3COO^-$, $(CH_3O)(H)PO_2^-$ and $N(CN)_2^-$.

In the present invention, the hydroxyl (OH), amino ($NH_2$ or NHR) and carboxyl (COOH) groups may be protected with appropriate protecting groups. One can refer to T. W. Green, P. G. M. Wuts, *Protective Groups in Organic Synthesis*, Wiley-Interscience, New York, 1999.

Among protecting groups for hydroxyl groups may be cited acetyl (Ac), benzoyl (Bz), benzyl (Bn), β-Methoxyethoxymethyl ether (MEM), Dimethoxytrityl, [bis-(4-methoxyphenyl)phenylmethyl] (DMT), Methoxymethyl ether (MOM), Methoxytrityl [(4-methoxyphenyl)diphenylmethyl, MMT), p-Methoxybenzyl ether (PMB), Methylthiomethyl ether, Pivaloyl (Piv), Tetrahydropyranyl (THP), Tetrahydrofuran (THF), and Trityl (triphenylmethyl, Tr).

Among protecting groups for amino groups may be cited t-butyl carbamate (Boc), 2-trimethylsilylethyl carbamate (Teoc), 1-(1-Adamantyl)-1-methylethyl carbamate (Adpoc), 1-Methyl-1-(4-biphenyl)ethyl carbamate (Bpoc), 1-(3,5-Di-t-butylphenyl)-1-methylethyl carbamate (t-Bumeoc), 1-Adamantyl Carbamate (Adoc), p-Methoxybenzyl carbamate (Moz), 9-Anthrylmethyl carbamate, Diphenylmethyl Carbamate, 9-Fluorenylmethyl carbamate (Fmoc), 9-(2-Sulfo) Fluoroenylmethyl carbamate, 9-(2,7-dibromo)Fluorenylmethyl carbamate, 2,7-Di-t-butyl-[9-(10,10-dioxo-10,10,10-tetrahydrothioxanthyl)]methylcarbamate (DBD-Tmoc), 2-(N,N-dicyclohexylcarboxamido)ethylCarbamate, 2-Phosphonioethyl carbamate (Peoc), 2-Phenylethyl carbamate, Benzyl carbamate (Cbz), Allyl carbamate (Alloc), 1-Isopropylallyl carbamate (Ipaoc), 4-Nitrocinnamyl Carbamate (Noc), 8-Quinolyl carbamate and N-Phtalimide.

Among protecting groups for carboxyl groups may be cited methyl esters, benzyl esters, tert-butyl esters, silyl esters, 2,6-dimethylphenol, 2,6-diisopropylphenol, and 2,6-di-tert-butylphenol.

The term "tag" or "tag moiety" relates to a chemical group appropriate for allowing one or several of the following:
  detection of the compound,
  vectorization of an agent of interest by the compound,
  solubilization of the compound,
  stabilization of the compound,
  improvement of the extraction and/or purification of the compound,
  modification of at least one of the ADME (Administration Distribution Metabolisation Excretion) parameters of the compound;

addition of bioactivity to the compound;

addition of an appropriate functionality for click-chemistry.

The compounds comprising such tags and according to the invention can therefore be used as a tool for detection, vectorization of an agent of interest, solubilization, stabilization, improvement of the extraction and/or purification, modification of at least one of the ADME (Administration Distribution Metabolisation Excretion) parameters; addition of bioactivity; and/or addition of an appropriate functionality for click-chemistry.

A chemical group appropriate for allowing detection of the compound of the invention may be any chemical group that can be identified and/or quantified by any technique of analysis known in the art. Among tags for detection can be cited fluorescent, such as fluorescent probes, such as fluorescein, quantum dots, cyanine dyes Cy3® and Cy5®, Alexa Fluor® dyes, Dylight Fluor® dyes, IRIS® Dyes, Seta® dyes, SeTau® dyes, SRfluor® dyes, Square® dyes, Nile red, FL or carboxytetramethylrhodamine (TAMRA); Nuclear Magnetic Resonance (NMR) tags, such as xenon or lanthanides (in particular terbium Tb or europium Eu); magnetic resonance imaging (MRI) contrast agents such as Gd chelates; mass spectrometry tags such as tris(2,4,6-trimethoxyphenyl)phosphonium (TMPP) or isotope-coded tags; infrared (IR) tags; positron emission tomography (PET) tags; single-photon emission computed tomography (SPECT) tags; tritium or deuterium atoms; microscopy tags such as gold nanoparticles; quenchers such as dabsyl (dimethylaminoazobenzene sulfonic acid).

A chemical group appropriate for allowing vectorization of an agent of interest with the compound of the invention may be any chemical group or biological moiety appropriate for helping the compound and/or the agent of interest to reach the appropriate tissue or organ, such as liver or bladder. For instance, the vectorization tag may be a chemical group able to form micelles, reverse-micelles or liposomes, such as an amphiphilic chemical group, a nano or microparticle, a viral vector, a polymer, a folate, an ammonium group, a peptide, an EGFR (Epidermal Growth Factor Receptor) ligand or an antibody.

A chemical group appropriate for allowing stabilization of the compound is a chemical group that affords increasing the half-life of the compound, preferably in vivo. For instance, the stabilization tag may be albumin, such as Human Serum Albumin HSA or Bovine Serum Albumin BSA.

A chemical group appropriate for allowing modification of the ADME parameters of the compound can be for instance a therapeutic agent, a drug, a prodrug, a polyethylene glycol of formula —(OCH$_2$—CH$_2$)$_n$—OR", wherein R" is a hydrogen atom or an alkyl group, wherein n is from 1 to 1000, preferably from 1 to 100, in particular from 1 to 8, a peptide, such as Proline-Alanine-Serine (Pro-Ala-Ser) or poly-Glu, a polypeptide, such as XTEN recombinant polypeptide, a lipid, such as palmitic acid, a carbohydrate, hydroxyethyl starch, a nucleic acid, such as DNA or RNA, in particular siRNA. The term "prodrug" relates to a variant of a drug that can be transformed in vivo into a drug. The term "peptide" relates to a peptide comprising from 1 to 20, preferably from 1 to 10, aminoacids.

The selection of the appropriate tag, such as the determination of the number of ethylene glycol moieties, can be easily adjusted by one of ordinary skill in the art depending of the desired ADME modification.

A chemical group appropriate for allowing extraction and/or purification of the compound may be any chemical group that favors and/or facilitates the extraction and/or purification of the compound of the invention. Among extraction and/or purification-tags can be cited biotin, chelating tags such as DTPA (diethylenetriaminepentaacetic acid), EDTA (ethylenediamine-N,N,N',N'-tetraacetic acid), NTA (nitrilotriacetic acid) and D4 (octamethylcyclotetrasiloxane), protein tags such as polyarginine or polyhistidine tags, preferably His6 or His10 tags, FLAG-tag, Strep-tag, c-myc-tag, S-tag, calmodulin-binding peptide, cellulose-binding domain, SBP-tag, chitin-binding domain, glutathione S-transferase tag, maltose-binding protein, NusA, TrxA and DsbA tags, boronic tags such as [(3-oxospiro[isobenzofuran-1(3H),9'-[9H]xanthene]-3',6'-diyl)bis(iminomethylene-2,1-phenylene)]bis-(9Cl), perfluoroalkyl groups, ionic (cationic or anionic) groups, such as ammonium groups, and solid surfaces such as polymeric materials, in particular polyethylene beads, nanoparticles, in particular magnetic nanoparticles, chips, silica beads or silica wafers.

A chemical group appropriate for addition of bioactivity may be for instance a chemical group comprising at least one radioisotope, such as $^{131}$I, $^{90}$Y, $^{89}$Sr, or $^{153}$Sm, or a derivative thereof.

A chemical group appropriate for reacting in click-chemistry may be for instance a chemical group selected from the group consisting of azides (such as N$_3$) and strained alkynes, in particular cyclic alkynes. Among cyclic alkynes may be cited for instance the bicyclononyne (BCN) and tetramethylthiepinium (TMTI) moieties.

In an embodiment, each of $R_1$ to $R_5$ is independently selected in the group consisting of:

alkyne groups, amino groups, hydroxylamine (—ONH$_2$) groups, hydrazine (—NH—NH$_2$) groups, azido (N$_3$) groups, diazonium (N2$^+$) groups, preferably in presence of a counterion, maleimide groups, carboxylic acid groups, aldehyde (—CHO) groups, boronic —B(OR")$_2$ groups, wherein R" is as described above, and activated esters.

In a preferred embodiment, none of $R_1$ to $R_5$ comprises a free SH group. In a preferred embodiment, $R_1$ and/or $R_5$ do not comprise any nucleophilic group, such as amino groups, hydroxylamine groups, hydrazine groups or hydroxyl groups.

In specific embodiments, 1, 2, 3, 4 or 5 of $R_1$ to $R_5$ are different from hydrogen atoms.

In specific embodiments, at least one of $R_1$ to $R_5$ comprises at least one moiety that is appropriate for further forming a covalent bond with a chemical group selected in the group consisting of thiol (SH) moieties, amine (NH$_2$) moieties and carboxylic acid (COOH) moieties. Among moieties appropriate for forming a covalent bond with thiol moieties, one can cite maleimide moieties. Among moieties appropriate for forming a covalent bond with amine moieties, one can cite NHS-ester moieties.

Among compounds of formula (I) according to the present invention may be cited the following compounds:

36
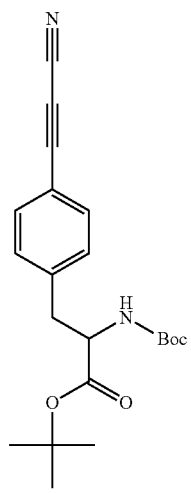
68
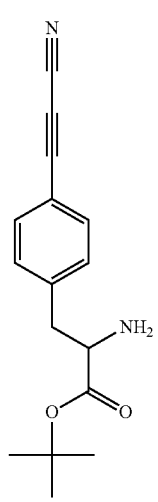
69
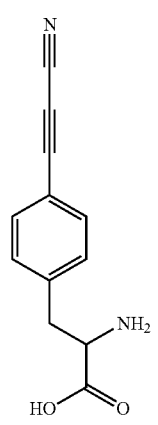
70
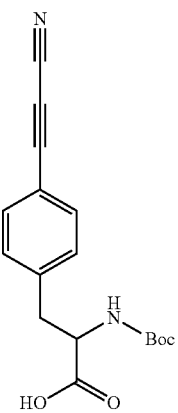
27
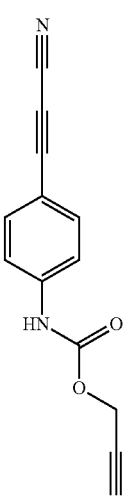
28

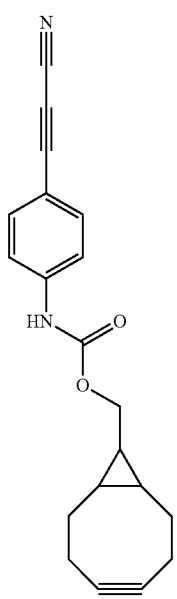
29
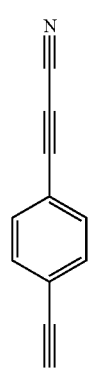
71
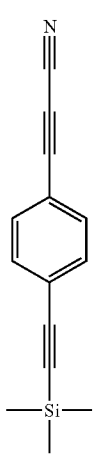
30
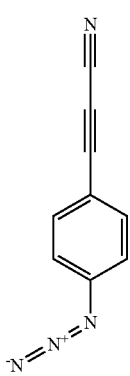
19
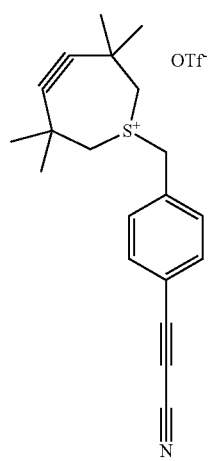
45
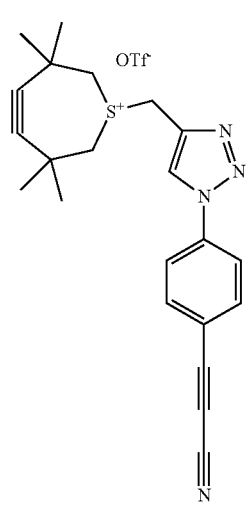
57

49
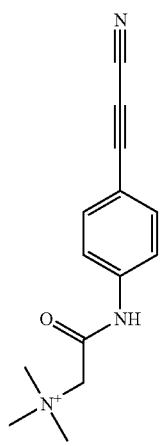
54
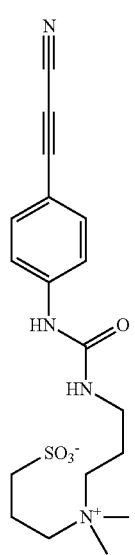
72
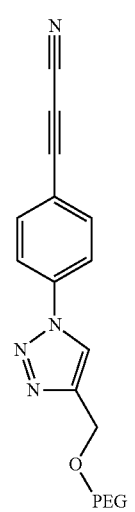
73
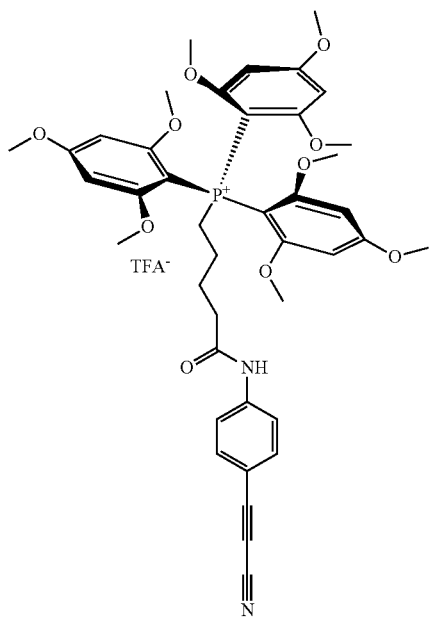
40
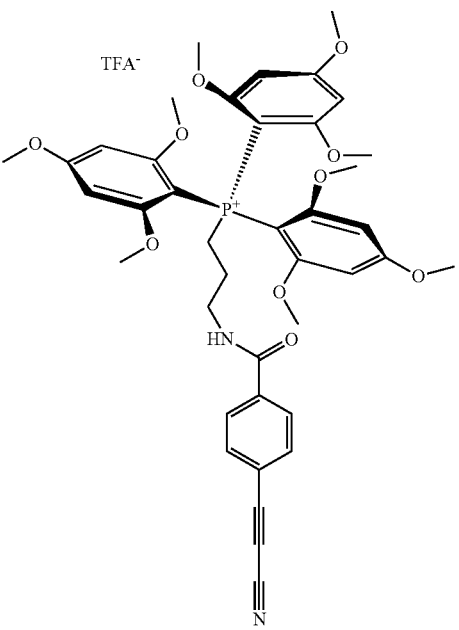

74
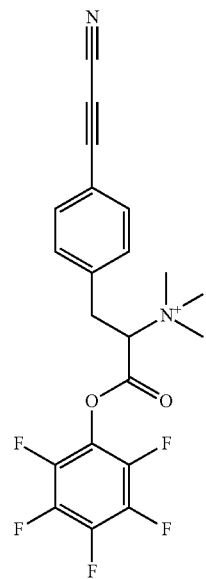
75
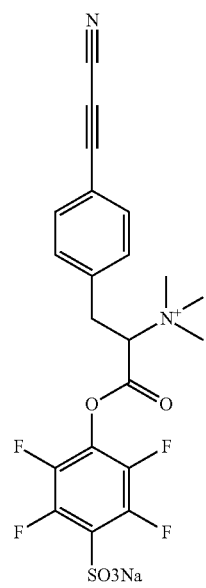
76
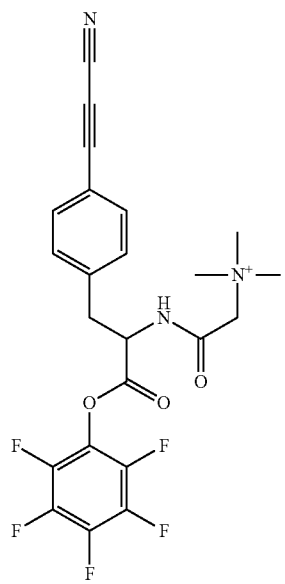
77
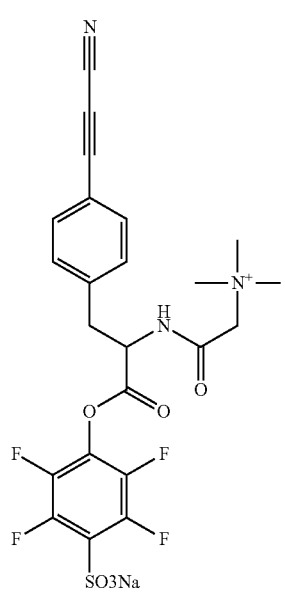
78
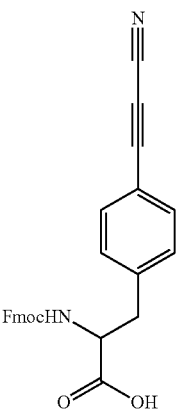

79
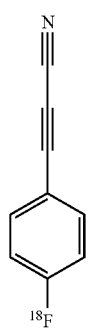
80
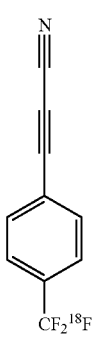
81
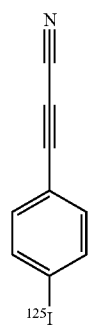
82
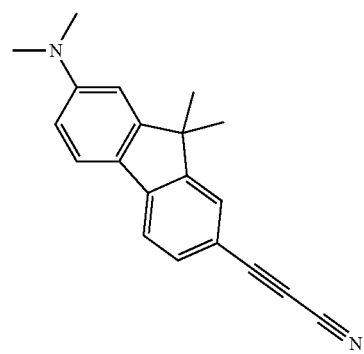
58
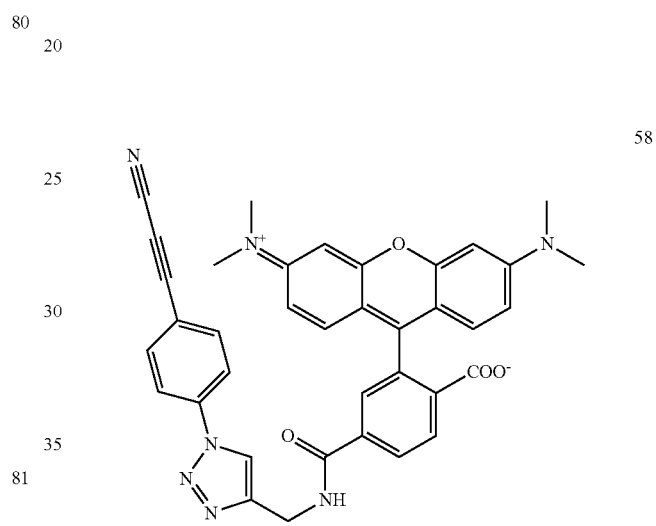
60
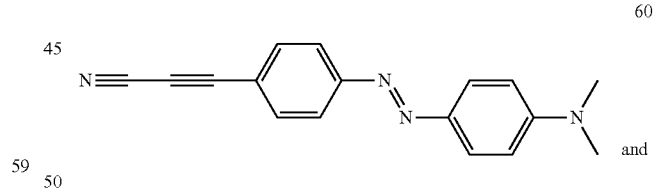
59
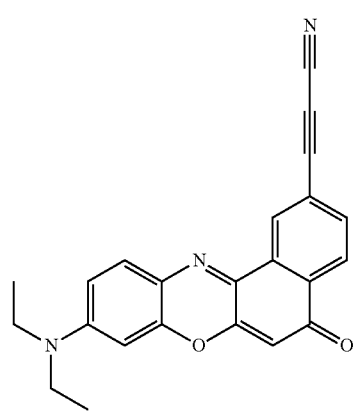
83
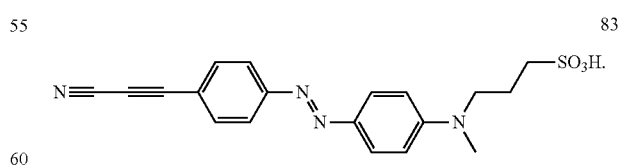
Among compounds of formula (I) may also be cited the following compounds:

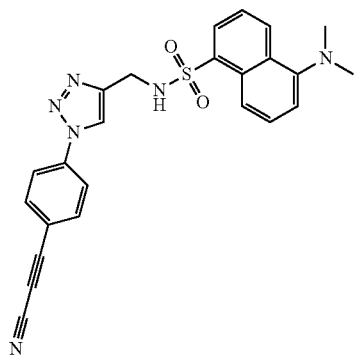
19
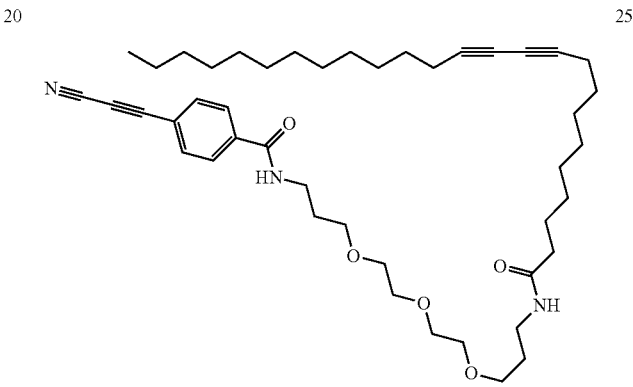
20
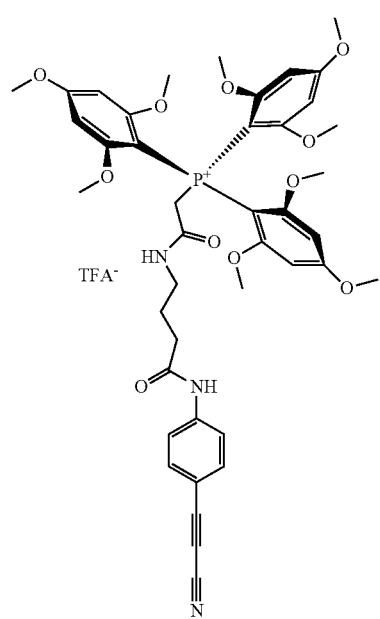
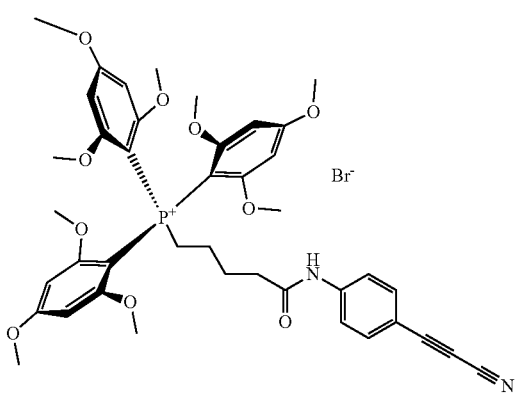
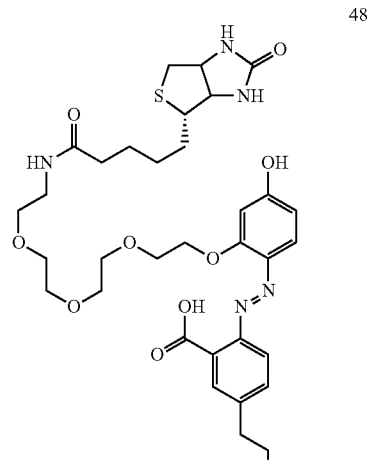

21
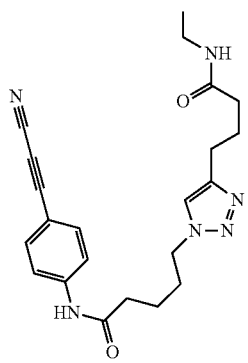
22
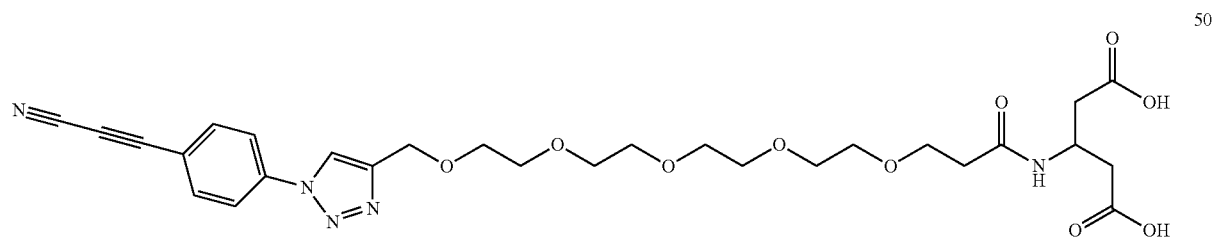
50
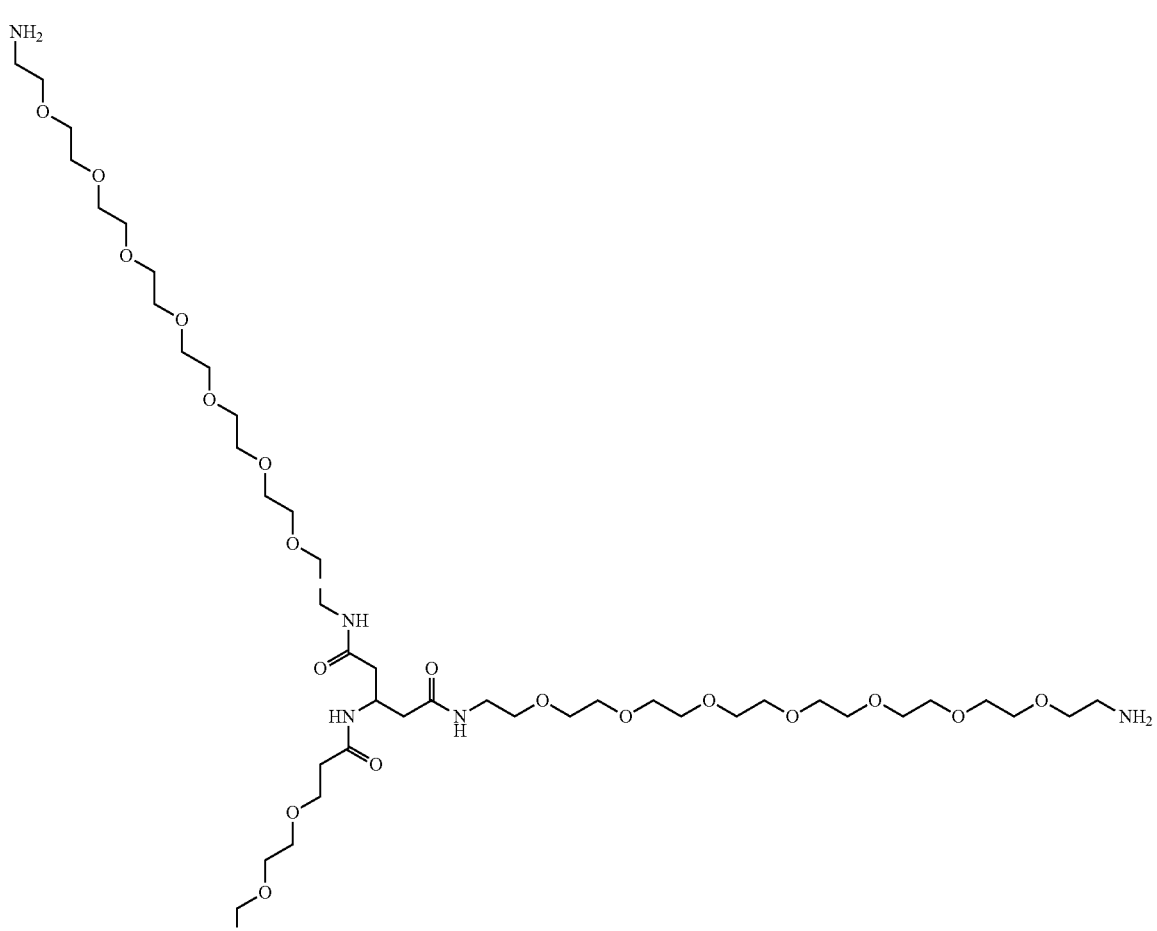
51

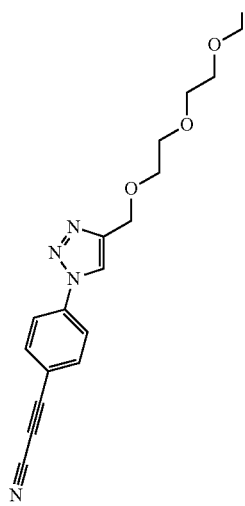

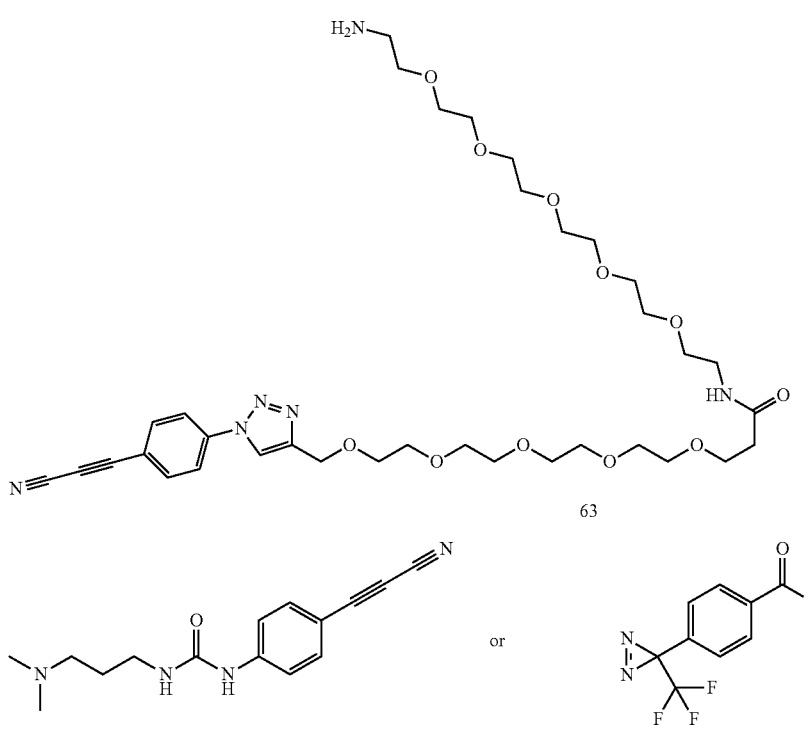

Synthesis of Compounds of the Invention

Compounds of formula (I) or (II) according to the invention can be synthesized for instance in two steps from the corresponding iodoarene, by coupling with propargyl alcohol, for instance via a Sonogashira coupling. The coupling is preferably followed by oxidation; for instance, the oxidation may be a tandem oxidation performed with $MnO_2$ in the presence of an ammonia solution. Alternatively, the compounds of the invention can be synthesized by cyanation of arylalkynes. Cyanation may be performed for instance with CuCN, arylisocyanates, cyanobenzotriazoles or cyanoimidazoles.

Labeling of Compounds Comprising at Least One Thiol Moiety

The compounds of formula (I) may be used in a process for labeling compounds comprising at least one thiol SH moiety. Preferably, the process of the invention comprises contacting at least one compound of formula (I) with a compound comprising at least one thiol SH moiety, or a sample susceptible to comprise such a compound.

Preferably, the sample is a biological sample, in particular an aqueous sample.

The term "labeling" in the present invention refers to the formation of a covalent bond between the sulfur atom of the thiol moiety and the propiolonitrile moiety of the compounds of formula (I).

The compound comprising a thiol moiety ($R_6$—SH compound) can be for instance a fluorophore, a quencher, an amino acid, a peptide, a protein, an enzyme, a drug, a prodrug and/or a drug metabolite.

$R_6$ may be any chemical group that is bonded to a thiol (SH) group to form a "compound comprising a thiol moiety". $R_6$ preferably comprises carbon, hydrogen, oxygen, nitrogen, phosphorus, and/or sulphur atoms.

In particular, the compound comprising a thiol moiety can be cystein, or a derivative, such as an ester, thereof, or a peptide or a protein comprising at least one cystein residue. Alternatively, the compound comprising a thiol moiety may be a surface presenting at least one free SH group.

Labeling of the compounds comprising a thiol moiety with compounds of formula (I) may be used for a great number of applications.

In a first embodiment, labeling of the compounds comprising a thiol moiety with compounds of formula (I) may be used in the detection and/or quantification of the compound comprising the thiol moiety in a sample. The detection means in the present invention identifying the presence or absence of the desired compound(s) in the sample.

The sample can be any sample susceptible to comprise the compound comprising at least one thiol moiety. For instance, the sample may be a biological sample, for instance a biological fluid, such as blood, plasma, serum, saliva, urine, etc., an extract of natural products, a biological tissue, or a part thereof, or a medium comprising cells.

In a second embodiment, labeling of the compounds comprising a thiol moiety with compounds of formula (I) may be used for conjugation of the compound comprising a thiol moiety with a moiety that improves its physico-chemical properties. For instance, the conjugated moiety may improve the solubility of the compound comprising a thiol moiety, or improve its synthesis and/or purification.

In a third embodiment, labeling of the compounds comprising a thiol moiety with compounds of formula (I) may be used for bio-conjugation of the compound comprising a thiol moiety with a compound of interest, such as a drug, a prodrug, a carbohydrate or a protein.

For instance, a compound of formula (I) comprising a compound of interest as tag may allow selective vectorization and/or binding of the compound of interest to the compound comprising at least one thiol moiety.

Another object of the invention is a compound of formula (I)

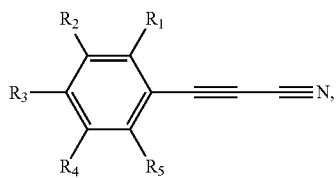

as defined above, including the described specific embodiments.

The invention also discloses a compound of formula (II)

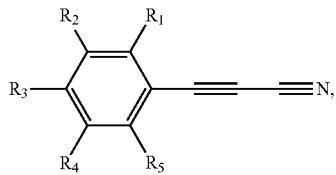

wherein each of $R_1$ to $R_5$ is selected independently in the group consisting of:
hydrogen atoms,
alkyl, alkene or alkyne groups, optionally interrupted by at least one heteroatom selected among O, N and S,
aryl groups,
alkoxy groups,
halogen atoms,
amino (—NRR') groups, wherein R and R' are independently hydrogen atoms or alkyl, alkene, alkyne or aryl groups as defined above,
hydroxylamine (—ONH$_2$) group,
hydrazine (—NH—NH$_2$) group,
nitro (—NO$_2$) group,
azido (—N$_3$) group,
diazonium (—N$_2^+$) group, preferably in presence of a counterion,
maleimide group,
alkyl- or aryl-carboxyl (—C(=O)OR) groups,
alkyl- or aryl-carbonyl (—C(=O)R) groups,
hydroxyl (—OH) group,
boronic —B(OR")$_2$ group, wherein R" is a hydrogen atom or an alkyl group,
phosphine or phosphonium groups,
isocyanate (—N=C=O) or isothiocyanate (—N=C=S) group,
chlorosulfonyl (—SO$_2$Cl) group,
a O—C(=O)—C(N$_2$)—CF$_3$ group or a —C(=O)—C(N$_2$)CF$_3$ group,
activated esters, such as —C(=O)—NHS, perfluorinated esters and acylureas,
tags, and
alkyl groups substituted by at least one of the previously listed groups.

The compounds of formula (II) are linkers to which at least one tag may be added to form the compounds of formula (I) as described above.

Among the compounds of formula (II) according to the present invention may be cited the following compounds:

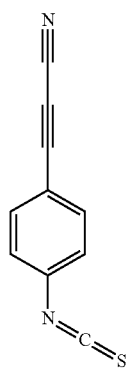

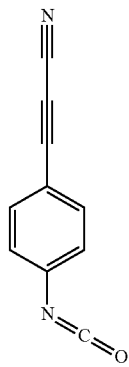

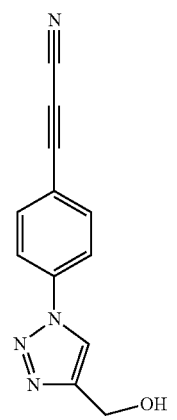
85
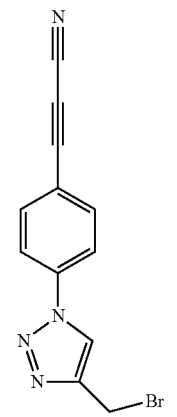
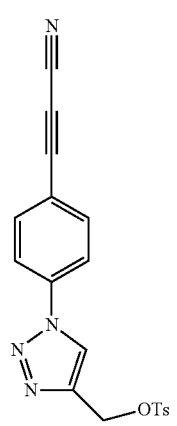
86
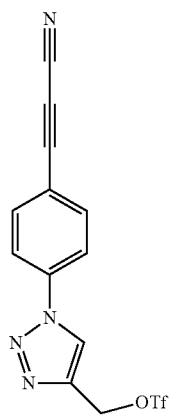
87
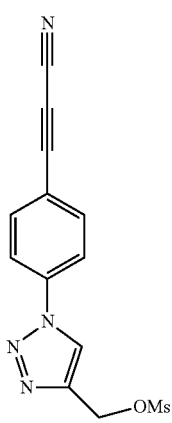
88
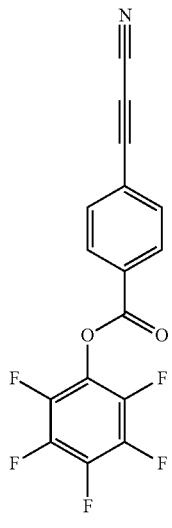
17

-continued
18
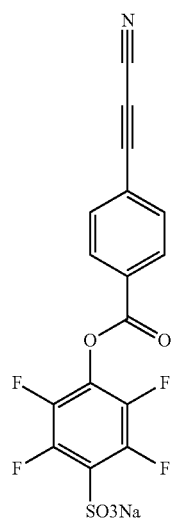
89
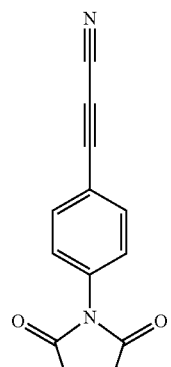
90
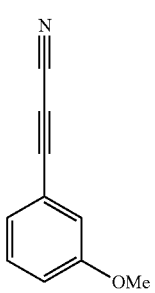
-continued
41
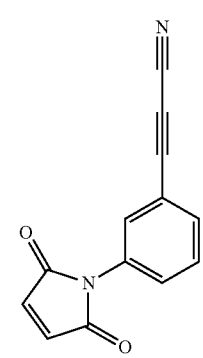
91
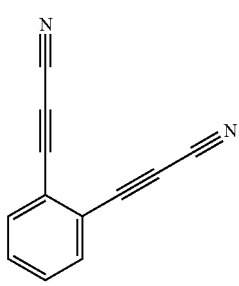
33
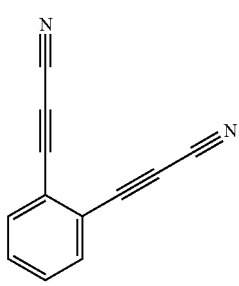
2
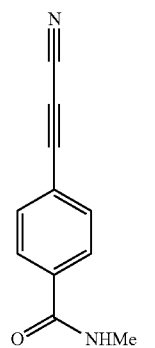
12
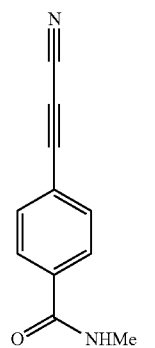

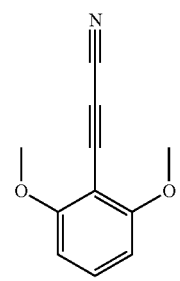
4
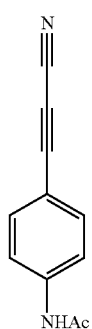
11
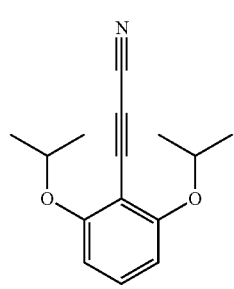
92
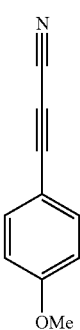
3
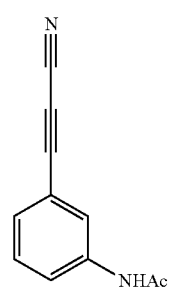
93
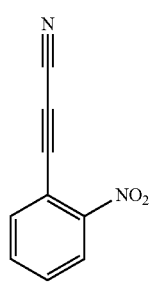
10
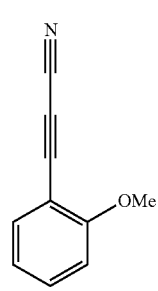
1
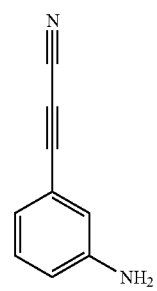
6
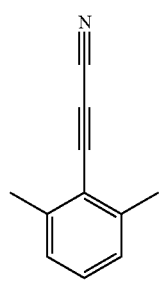
9
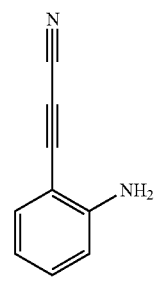
5

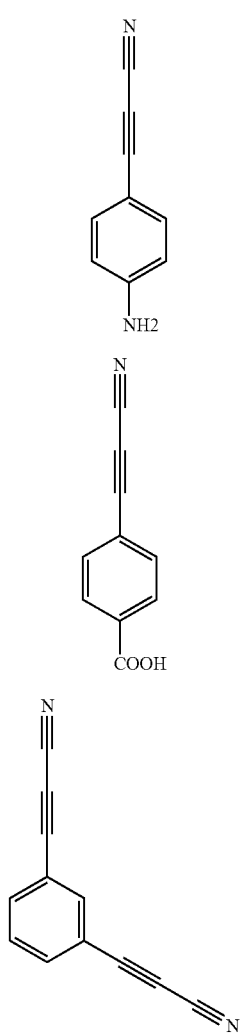
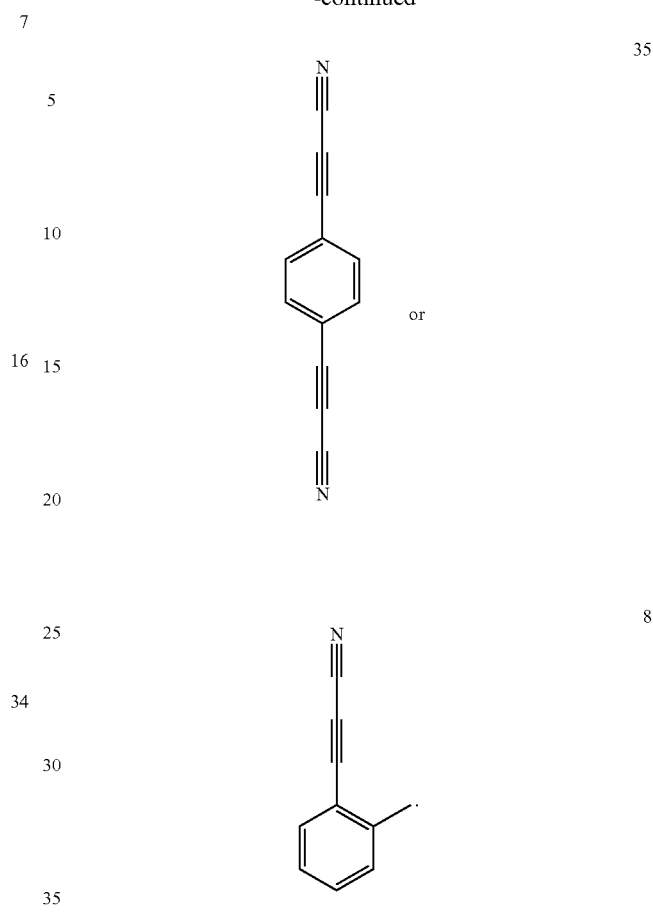
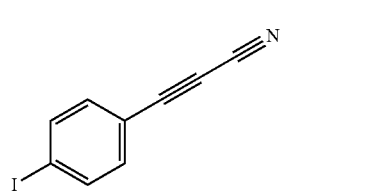
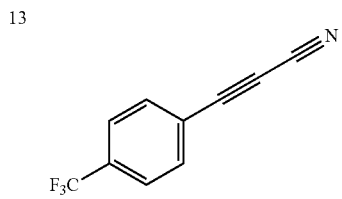
Among the compounds of formula (II) according to the present invention may also be cited the following compounds:
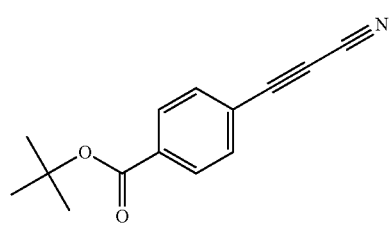

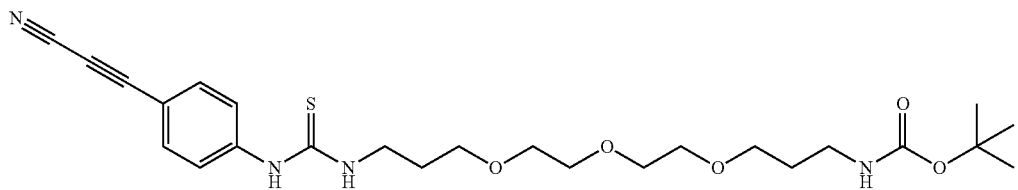
22
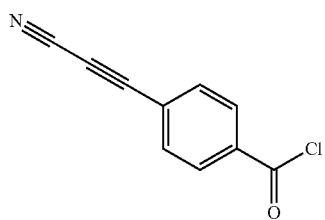
23
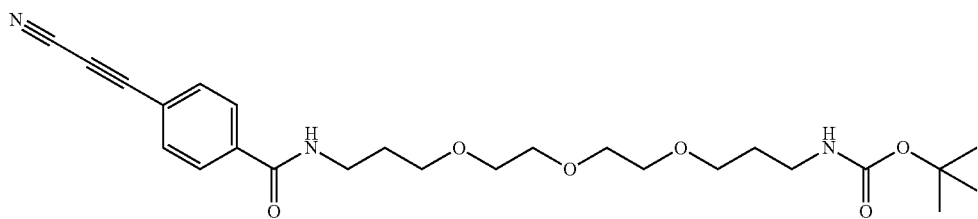
24
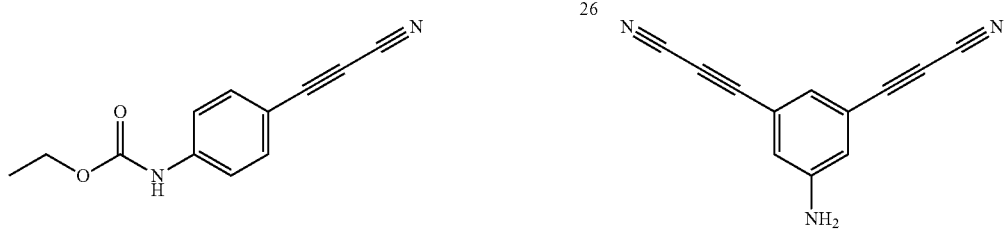
26    31
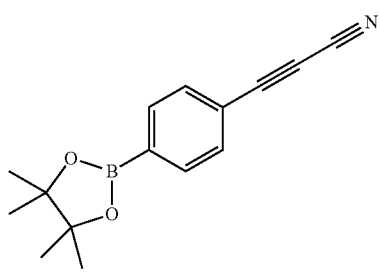
32
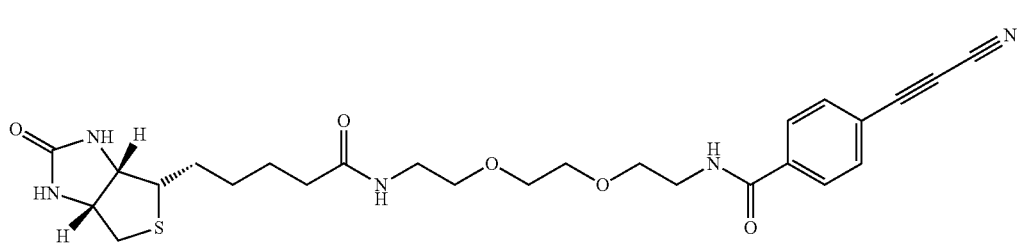
37

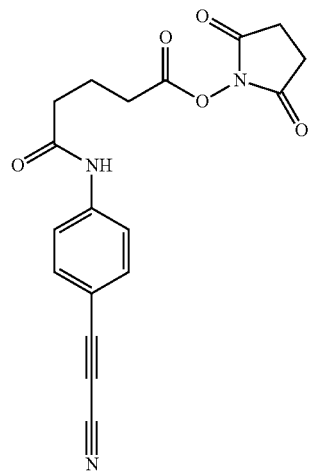
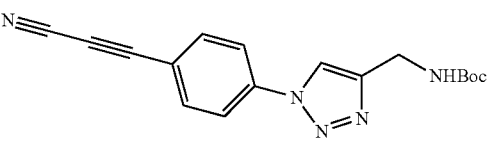
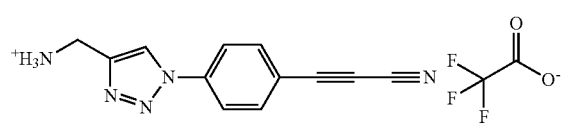
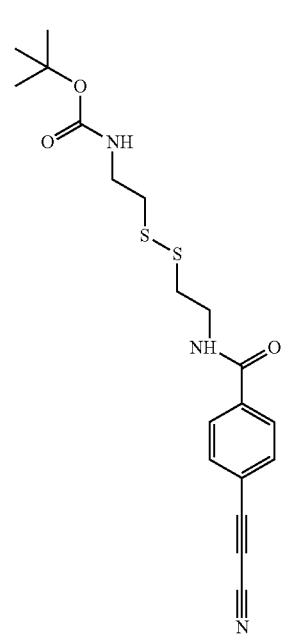
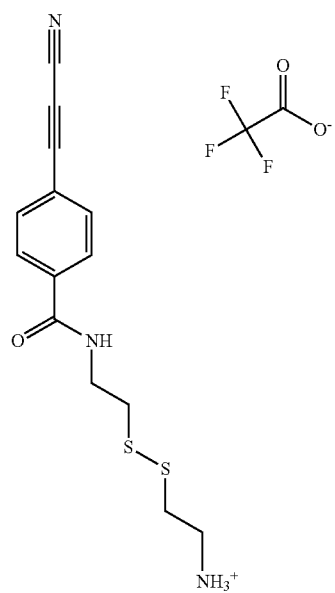

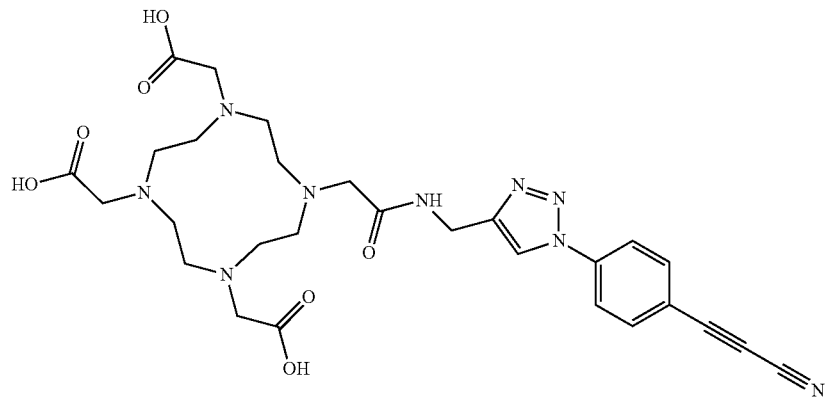

66

The process for labeling a compound comprising a thiol moiety according to the invention may further comprise, before the step of contacting the compound comprising a thiol moiety with a compound of formula (I), a preliminary step of preparation of the compound of formula (I), comprising contacting a compound of formula (II) with a compound comprising a tag moiety, or a precursor thereof.

The term "precursor" relates in the present case to a chemical group that is able to form, after contacting with the compound of formula (II), the tag moiety.

Preferably, at least one of $R_1$ to $R_5$ is different from a hydrogen atom.

An object of the invention is a compound of formula (II), wherein at least one of $R_1$ to $R_5$ comprises, preferably is, a maleimide, an azide ($N_3$) group, an alkyne or a NHS-ester moiety.

The maleimide and NHS-ester moieties respectively allow further linking of the compound to another thiol or an amine group; the $N_3$ group allows further linking of the compound to another alkyne-group and the alkyne group allows further linking of the compound to another $N_3$ group.

In an embodiment, the compound of formula (II) according to the invention is selected from the following compounds:

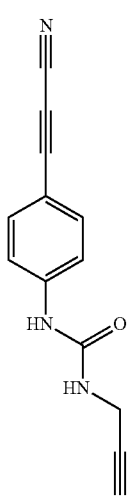

27

-continued

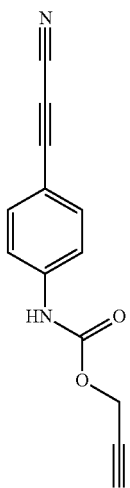

28

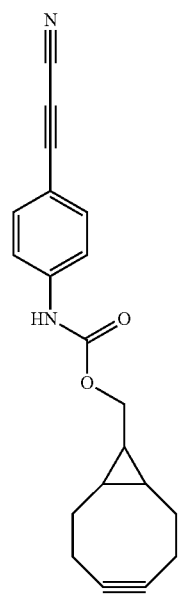

29

71

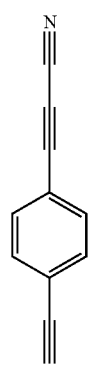

30

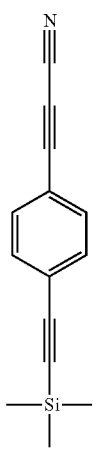

19

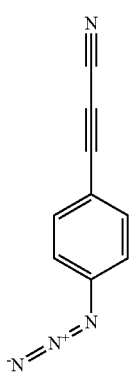

41

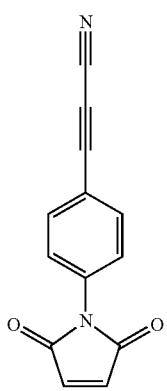

91

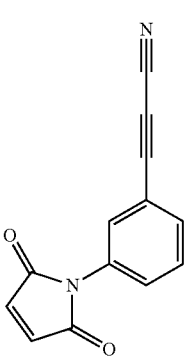

25

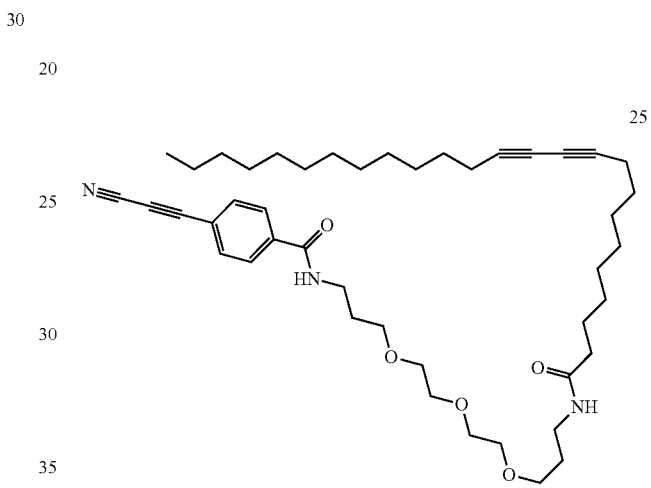

44

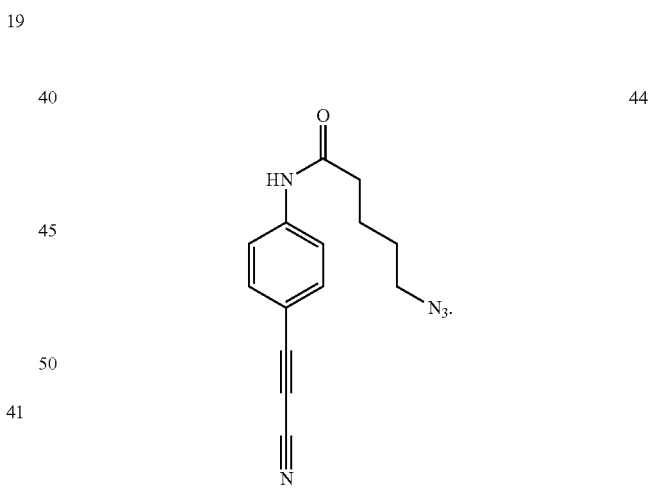

The invention also relates to compounds of formula (I) or (II), wherein at least one of $R_1$ to $R_5$ is further bonded to a compound of interest.

A compound of interest may be for instance a molecule, such as a fluorophore, for instance rhodamine, a group of atoms comprising at least one radioactive atom ($^{14}$C, $^{3}$H, or $^{131}$I for instance), a group of atoms of known mass (a mass tag), a ligand, a drug, a therapeutic agent, a biomolecule, such as an antibody, a protein, such as BSA (bovine serum albumin), a DNA fragment, a nanoobject, such as a nanoparticle (ie an object or a particle of 0.1 to 1000 nm), or a support, such as a polymer.

When the process of labeling according to the invention is performed with such a compound of formula (I) or (II) wherein at least one of $R_1$ to $R_5$ is further bonded to a compound of interest, the process affords the formation of a conjugate between the compound of interest and the compound comprising a thiol moiety.

In an embodiment, the compound of interest is a biomolecule such as a protein or an antibody, and the compound comprising a thiol moiety is a fluorophore such as a compound comprising a TAMRA moiety and a thiol moiety (TAMRA-SH).

In an embodiment, the compound of interest is a biomolecule such as a protein or an antibody, and the compound comprising a thiol moiety is a drug or a therapeutic agent. The conjugate obtained by the process of labeling according to the invention is a therapeutic antibody.

Another object of the invention is a compound of formula (III):

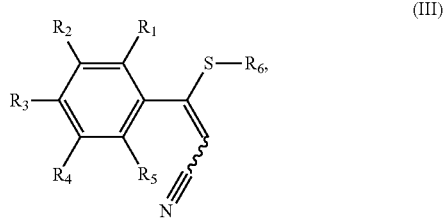

wherein $R_6$—S corresponds to the moiety of the compound comprising at least one thiol moiety as defined above. In particular, the compound of formula (III) is of formula (IV):

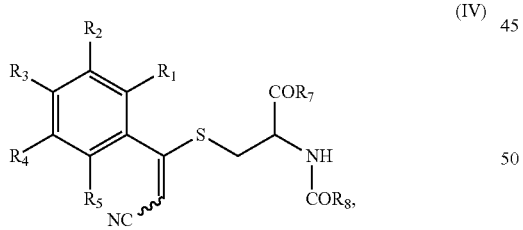

wherein $R_7$ and $R_8$ are selected in the group consisting of OH, tag, alkyl, O-alkyl, and peptidic moieties, wherein the alkyl groups may be substituted by at least one tag moiety. A peptidic moiety is a moiety comprising at least one aminoacid, when the moiety presents more than one aminoacid (2, 3, 4, 5, . . . ), the aminoacids are linked between each other by peptidic bonds. Preferably, the double bond of the compound of formula (III) or (IV) is of (Z) configuration. The tag and alkyl groups are as defined above.

Among compounds of formula (III) according to the present invention may be cited the following compounds:

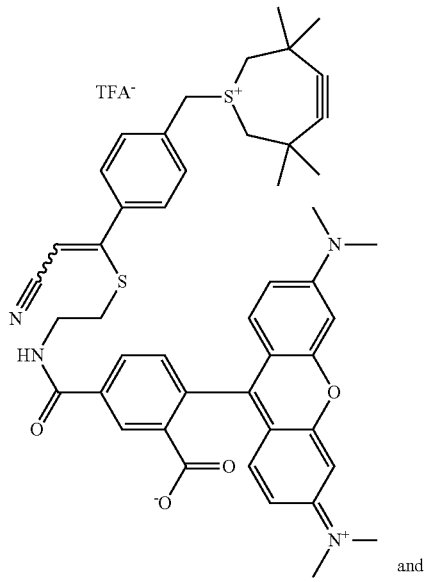

and

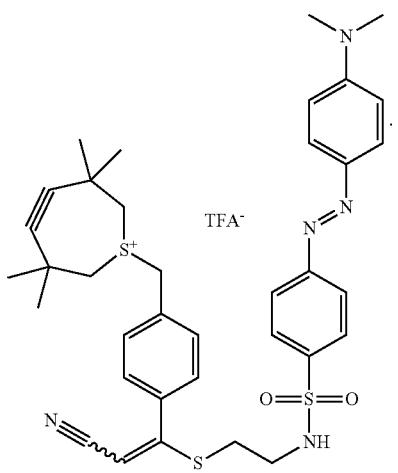

The compounds of formula (I) have surprisingly been found to be more stable in aqueous medium than the corresponding compounds wherein the 3-arylpropiolonitrile moiety is replaced with a maleimide moiety, which is classically used for labeling thiol moieties. For instance, compound 1

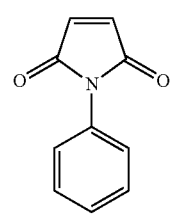 [SMILES: O=C1C=CC(=O)N1c1ccccc1]

was approximately 25% hydrolyzed after 1 h in buffer solution ($k_{obs}$=7×10$^{-5}$s$^{-1}$), while no hydrolysis could be detected for compound 11

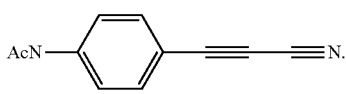

Interestingly, even after a week at room temperature, no trace of hydrolyzed product could be detected for compound 11.

In addition, the compounds of formula (II) according to the invention showed a marked selectivity towards cysteine compared to other amino-acids which do not comprise free thiol moieties. Comparatively, the chemoselectivity obtained for the corresponding compounds wherein the 3-arylpropiolonitrile moiety is replaced with a maleimide moiety is lower.

Finally, the compounds of formula (III) as described above have shown to be highly more stable in biological conditions than the corresponding compounds wherein the 3-arylpropiolonitrile moiety is replaced with a maleimide moiety. For instance, the addition product

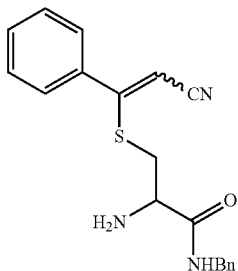

between compound

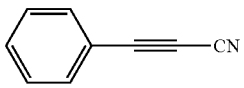

and cysteine derivative 3

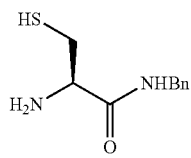

was particularly stable in a wide range of conditions, such as physiological conditions. In particular, said addition product was stable in a wide range of pH (from 0 to 14), and no exchange product could be observed after one hour of reaction with an excess of phenylthiol and glutathione.

The invention will be illustrated in more detail with reference to the following examples, but it should be understood that the present invention is not deemed to be limited thereto.

EXAMPLES

Example 1

Synthesis of Compounds of the Invention

Synthesis of Compounds of Formula (II)

A series of compounds of formula (I) or (II) were synthesized and characterized according to the following procedures.

General Protocols:
Sonogashira Coupling

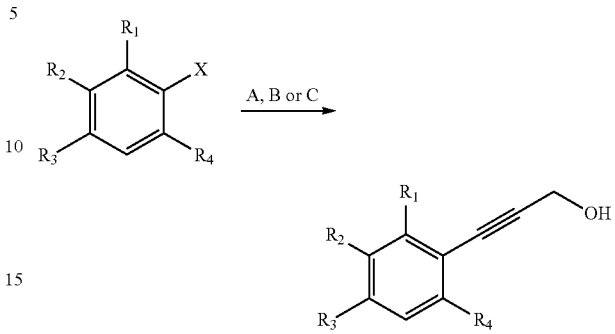

Standard Reaction Protocols:

A. To a degased solution of the proper aryl halide (1 eq., 1 mmol) in DMF (5 mL) and DIPEA (10 eq., 10 mmol), premixed $PdCl_2(PPh_3)_2$ (0.03 eq., 30 µmol) and CuI (0.06 eq., 60 µmol) were added. Obtained reaction mass was degased, stirred for another 5 minutes, followed by the addition of propargyl alcohol (1.2 eq., 1.2 mmol). The reaction mass was stirred for 1-24 hours (monitored by TLC). 1M HCl (50 mL) was added (if contains free amino groups, 50 mL of water were added instead) and the reaction mixture was extracted with ethyl acetate (3×20 mL). United ethyl acetate fractions were washed with water (1×10 mL) dried over $MgSO_4$ and evaporated to give crude product. Products were purified by flash chromatography (gradient of 20 minutes from 100% of cyclohexane to 100% of ethyl acetate).

B. To a degased solution of the proper aryl halide (1 eq., 1 mmol) in THF (5 mL) and TEA (5 mL), premixed $PdCl_2(PPh_3)_2$ (0.03 eq., 30 µmol) and CuI (0.06 eq., 60 µmol) were added, followed by the addition of propargyl alcohol (2 eq., 1.2 mmol). The reaction mass was stirred for 1-24 hours (monitored by TLC). THF and TEA were evaporated and the crude product was purified by flash chromatography (gradient of 20 minutes from 100% of cyclohexane to 100% of ethyl acetate).

C. To a degased solution of the proper aryl halide (1 eq., 1 mmol) in propylamine or pyrrolidine (3 mL), $Pd(PPh_3)_4$ (0.05 eq., 50 µmol) was added. The reaction mass was heated overnight (30-50° C.), evaporated and the crude product was purified by flash chromatography (gradient of 20 minutes from 100% of cyclohexane to 100% of ethyl acetate).

Preparation of Highly Active $MnO_2$

A solution of $MnCl_2.4H_2O$ (1 eq., 1 mole, 200 g) in water (2 L) at 70° C. was gradually added during 10 minutes, with stirring, to a solution of $KMnO_4$ (1 eq., 1 mole, 160 g) in water (2 L) at 60° C. in a hood. A vigorous reaction ensued with evolution of chlorine; the suspension was stirred for 2 hours and kept overnight at room temperature. The precipitate was filtered off, washed thoroughly with water (4 L) until pH 6.5-7 and the washing gave a negligible chloride test. The filter cake was then dried at 120-130° C. for 18 h; this gave a chocolate-brown, highly disperse amorphous powder.

MnO₂ Oxidation

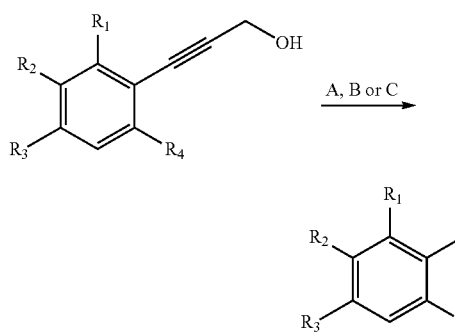

Slightly modified procedure described by McAllister et al.[824] To a solution of the proper propargylic alcohol (1 eq., 1 mmol) in THF (4.5 mL), MgSO₄ (15 eq., 15 mmol), highly active MnO₂ (25 eq., 25 mmol) and 2M NH₃ solution in IPA (4 eq., 4 mmol, 2 mL) were added. Obtained reaction mass was vigorously stirred at room temperature for 0.5-12 hours (monitored by TLC). DCM (20 mL) were added and the obtained reaction mass was filtered through Celite, evaporated to give crude product and purified by flash chromatography if required.

Substituted 3-(aryl)prop-2-yn-1-ols (1a-12a)

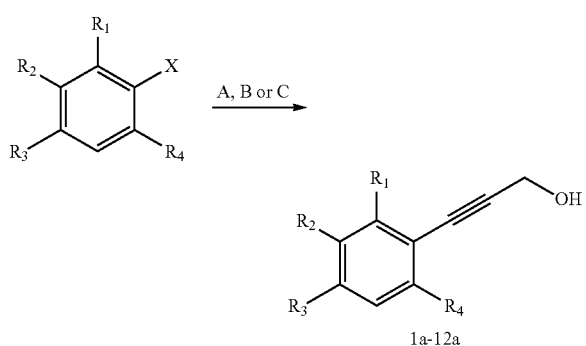

|  | $R_1$ | $R_2$ | $R_3$ | $R_4$ | X | Protocol |
|---|---|---|---|---|---|---|
| 1a | OMe | H | H | H | I | B |
| 2a | H | OMe | H | H | Br | C |
| 3a | H | H | OMe | H | I | B |
| 4a | OMe | H | H | OMe | I | C |
| 5a | NH₂ | H | H | H | I | B |
| 6a | H | NH₂ | H | H | I | A |
| 7a | H | H | NH₂ | H | I | A |
| 8a | Me | H | H | H | I | B |
| 9a | Me | H | H | Me | I | A |
| 10a | NO₂ | H | H | H | Br | B |
| 11a | H | H | NHAc | H | I | A |
| 12a | H | H | CONHMe | H | I | A |

3-(2-Methoxyphenyl)prop-2-yn-1-ol (1a)

Reaction time: 18 hours; yield: 72%.
¹H NMR (400 MHz, METHANOL-d₄) δ 7.36 (dd, J=1.5, 7.5 Hz, 1H), 7.26-7.33 (m, 1H), 6.97 (d, J=8.3 Hz, 1H), 6.86-6.93 (m, 1H), 4.43 (s, 2H), 3.84 (s, 3H); ¹³C NMR (101 MHz, METHANOL-d₄) δ161.6, 134.5, 131.0, 121.5, 113.4, 112.0, 92.7, 82.0, 56.2, 51.5.

3-(3-Methoxyphenyl)prop-2-yn-1-ol (2a)

Reaction time: 16 hours; yield: 87%.
¹H NMR (400 MHz, METHANOL-d₄) δ 7.15-7.24 (pseudo-t, J=7.5 Hz, 1H), 7.00 (d, J=7.5 Hz, 1H), 6.93-6.98 (m, 1H), 6.87 (dd, J=2.13, 7.5 Hz, 1H), 4.41 (s, 2H), 3.73 (s, 3H); ¹³C NMR (101 MHz, METHANOL-d₄) δ 160.9, 130.6, 125.4, 125.1, 117.8, 115.7, 88.8, 85.6, 55.9, 51.4.

3-(4-Methoxyphenyl)prop-2-yn-1-ol (3a)

Reaction time: 16 hours; yield: 92%.
¹H NMR (400 MHz, CHLOROFORM-d) δ 7.40 (d, J=8.78 Hz, 2H), 6.86 (d, J=8.78 Hz, 2H), 4.51 (d, J=4.9 Hz, 2H), 3.83 (s, 3H), 1.78 (t, J=4.9 Hz, 1H); ¹³C NMR (101 MHz, CHLOROFORM-d) δ 159.8, 133.2, 114.6, 114.0, 85.9, 85.7, 55.3, 51.7.

3-(2-Aminophenyl)prop-2-yn-1-ol (4a)

Reaction time: 24 hours; yield: 62%.
1H NMR (400 MHz, METHANOL-d₄) δ 7.19 (dd, J=1.25, 7.9 Hz, 1H), 7.03-7.12 (m, 1H), 6.75 (d, J=7.9 Hz, 1H), 6.56-6.65 (m, 1H), 4.47 (s, 2H), 4.26 (s, 2H); ¹³C NMR (101 MHz, METHANOL-d₄) δ 150.3, 133.0, 130.6, 118.2, 115.6, 93.8, 78.9, 69.5, 51.0.

3-(3-Aminophenyl)prop-2-yn-1-ol (5a)

Reaction time: 18 hours; yield: 77%.
¹H NMR (400 MHz, CHLOROFORM-d) δ 7.08 (t, J=7.8 Hz, 1H), 6.83 (d, J=7.8 Hz, 1H), 6.76 (s, 1H), 6.64 (dd, J=1.5, 7.8 Hz, 1H), 4.46 (s, 2H), 2.17 (s, 1H); ¹³C NMR (101 MHz, CHLOROFORM-d) δ 146.3, 129.2, 123.4, 122.0, 118.0, 115.5, 87.0, 85.6, 51.4.

3-(4-Aminophenyl)prop-2-yn-1-ol (6a)

Reaction time: 18 hours; yield: 42%.
¹H NMR (400 MHz, METHANOL-d₄) δ 7.11-7.21 (d, J=8.5 Hz, 2H), 6.53-6.68 (d, J=8.5 Hz, 2H), 4.37 (s, 2H); ¹³C NMR (101 MHz, METHANOL-d₄) δ 149.7, 133.8, 115.7, 112.5, 86.7, 85.9, 51.4.

3-(2-Nitrophenyl)prop-2-yn-1-ol (7a)

Reaction time: 15 hours; yield: 35%.
¹H NMR (400 MHz, CHLOROFORM-d) δ 7.97 (d, J=8.0 Hz, 1H), 7.54-7.60 (d, J=8.0 Hz, 1H), 7.46-7.54 (t, J=8.0 Hz, 1H), 7.36-7.44 (t, J=8.0 Hz, 1H), 4.49 (s, 2H), 1.68 (br. s., 1H); ¹³C NMR (101 MHz, CHLOROFORM-d) δ 149.9, 134.8, 132.8, 128.9, 124.6, 118.0, 95.2, 80.9, 51.7.

4-(3-Hydroxyprop-1-yn-1-yl)-N-methylbenzamide (8a)

Reaction time: 12 hours; yield: 91%.
¹H NMR (400 MHz, METHANOL-d₄) δ 7.72-7.82 (m, J=8.28 Hz, 2H), 7.41-7.53 (m, J=8.28 Hz, 2H), 4.43 (s, 2H), 2.92 (s, 3H); ¹³C NMR (101 MHz, METHANOL-d₄) δ 169.9, 135.2, 132.7, 128.3, 127.6, 91.5, 84.7, 51.3, 27.1.

N-(4-(3-Hydroxyprop-1-yn-1-yl)phenyl)acetamide (9a)

Reaction time: 18 hours; yield: 85%.
$^1$H NMR (400 MHz, METHANOL-$d_4$) δ 7.56-7.64 (d, J=8.8 Hz, 2H), 7.47-7.56 (d, J=8.8 Hz, 2H), 4.74 (s, 2H), 2.04 (s, 3H); $^{13}$C NMR (101 MHz, METHANOL-$d_4$) δ 171.9, 143.8, 135.7, 120.7, 112.8, 106.2, 84.5, 62.7, 24.1.

3-(o-Tolyl)prop-2-yn-1-ol (10a)

Reaction time: 5 hours; yield: 70%.
$^1$H NMR (400 MHz, CHLOROFORM-d) δ 7.40 (d, J=7.5 Hz, 1H), 7.11-7.24 (m, 3H), 4.54 (s, 2H), 2.43 (s., 3H); $^{13}$C NMR (101 MHz, CHLOROFORM-d) δ 138.2, 131.2, 128.4, 128.0, 119.3, 115.3, 86.5, 85.2, 51.2, 21.2.

3-(2,6-Dimethylphenyl)prop-2-yn-1-ol (11a)

Reaction time: 24 hours; yield: 25%.
$^1$H NMR (400 MHz, CHLOROFORM-d) δ 7.03 (t, J=7.5 Hz, 1H), 6.95 (d, J=7.5 Hz, 2H), 4.50 (s, 2H), 2.34 (s, 7H); $^{13}$C NMR (101 MHz, CHLOROFORM-d) δ 140.5, 127.9, 126.7, 122.3, 95.6, 83.3, 51.9, 21.1.

3-(2,6-Dimethoxyphenyl)prop-2-yn-1-ol (12a)

Reaction conditions: 30° C., propylamine, 16 hours; yield: 38%.
$^1$H NMR (400 MHz, METHANOL-$d_4$) δ 7.25 (t, J=8.4 Hz, 1H), 6.62 (d, J=8.4 Hz, 2H), 4.46 (s, 2H), 3.84 (s, 6H); $^{13}$C NMR (101 MHz, METHANOL-$d_4$) δ 163.0, 131.0, 104.7, 102.5, 97.0, 78.1, 56.4, 51.7.

Substituted 3-aryl-propiolonitriles (1-12)

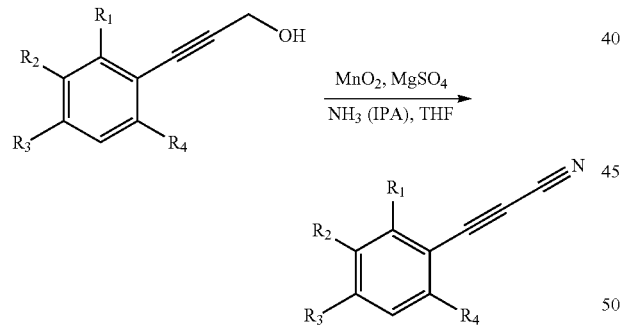

|    | $R_1$  | $R_2$  | $R_3$  | $R_4$ | Time, h | Yield, % |
|----|--------|--------|--------|-------|---------|----------|
| 1  | OMe    | H      | H      | H     | 3       | 45       |
| 2  | H      | OMe    | H      | H     | 2       | 85       |
| 3  | H      | H      | OMe    | H     | 3       | 95       |
| 4  | OMe    | H      | H      | OMe   | 4       | 60       |
| 5  | $NH_2$ | H      | H      | H     | 1       | 47       |
| 6  | H      | $NH_2$ | H      | H     | 2       | 71       |
| 7  | H      | H      | $NH_2$ | H     | 9       | 94       |
| 8  | Me     | H      | H      | H     | 1.5     | 70       |
| 9  | Me     | H      | H      | Me    | 2       | 55       |
| 10 | $NO_2$ | H      | H      | H     | 4       | 21       |
| 11 | H      | H      | NHAc   | H     | 2       | 92       |
| 12 | H      | H      | CONHMe | H     | 2       | 61       |

3-(2-Methoxyphenyl)propiolonitrile (1, APN-o-OMe)

$^1$H NMR (400 MHz, METHANOL-$d_4$) δ 7.51-7.65 (m, 2H), 7.12 (d, J=8.3 Hz, 1H), 7.01 (t, J=7.7 Hz, 1H), 3.94 (s, 4H); $^{13}$C NMR (101 MHz, METHANOL-$d_4$) δ 164.7, 136.4, 135.3, 122.0, 112.6, 107.7, 106.4, 81.8, 66.7, 56.7; IR (neat film, cm$^{-1}$): 2946, 2264, 2142 1596, 1490, 1245, 1164, 1122, 1047, 1021, 752, 498; GC-ESI-HRMS: 157.05276. found 157.05044.

3-(3-Methoxyphenyl)propiolonitrile (2, APN-m-OMe)

$^1$H NMR (400 MHz, METHANOL-$d_4$) δ 7.38 (t, J=7.8 Hz, 1H), 7.27 (d, J=7.8 Hz, 1H), 7.20-7.24 (m, 1H), 7.12-7.20 (m, 1H), 3.83 (s, 3H); $^{13}$C NMR (101 MHz, METHANOL-$d_4$) δ 161.2, 131.4, 127.1, 120.0, 119.4, 119.2, 106.0, 84.1, 62.7, 56.1; IR (neat film, cm$^{-1}$): 2491, 2264, 2144, 1595, 1573, 1488, 1464, 1420, 1324, 1294, 1207, 1178, 1045, 783, 681, 494; GC-ESI-HRMS: 157.05276. found 157.05298.

3-(4-Methoxyphenyl)propiolonitrile (3, APN-p-OMe)

$^1$H NMR (400 MHz, CHLOROFORM-d) δ 7.46-7.70 (m, J=8.8 Hz, 2H), 6.86-6.96 (m, J=8.8 Hz, 2H), 3.86 (s, 3H); $^{13}$C NMR (101 MHz, CHLOROFORM-d) δ 161.4, 134.4, 113.7, 108.2, 104.8, 82.7, 61.5, 54.5; IR (neat film, cm$^{-1}$): 2985, 2358, 2342, 2263, 2178, 2149, 1603, 1514, 1307, 1270, 1180, 1028, 835, 808, 669, 424; GC-ESI-HRMS: 157.05276. found 157.05337.

3-(2,6-Dimethoxyphenyl)propiolonitrile (4, APN-o,o'-diOMe)

$^1$H NMR (400 MHz, CHLOROFORM-d) δ 7.38 (t, J=8.5 Hz, 1H), 6.53 (d, J=8.5 Hz, 2H), 3.88 (s, 6H); $^{13}$C NMR (101 MHz, CHLOROFORM-d) δ 164.4, 133.8, 106.2, 103.4, 96.5, 77.7, 70.5, 56.2; IR (neat film, cm$^{-1}$): 2847, 2359, 2259, 2201, 2139, 1926, 1586, 1574, 1478, 1432, 1302, 1255, 1188, 1109, 1025, 778, 727, 648, 632, 545, 506, 488, 420; GC-ESI-HRMS: 187.06333. found 184.06465.

3-(2-Aminophenyl)propiolonitrile (5, APN-o-NH2)

$^1$H NMR (500 MHz, METHANOL-$d_4$) δ 6.81 (d, J=7.88 Hz, 1H), 6.65-6.76 (m, 1H), 6.08-6.19 (m, 2H), 3.85 (br. s., 1H); $^{13}$C NMR (126 MHz, CHLOROFORM-d) δ 151.4, 134.0, 133.4, 118.2, 115.0, 105.8, 101.0, 81.6, 68.5; IR (neat film, cm$^{-1}$): 3413, 3332, 3211, 2925, 2853, 2250, 2136, 1632, 1600, 1563, 1486, 1452, 1312, 1273, 1252, 1161, 740, 673, 493; GC-ESI-HRMS: 142.05310. found 142.05458.

3-(3-Aminophenyl)propiolonitrile (6, APN-m-NH$_2$)

$^1$H NMR (400 MHz, CHLOROFORM-d) δ 7.17 (t, J=7.6 Hz, 1H), 6.99 (d, J=7.6 Hz, 1H), 6.74-6.89 (m, 2H), 3.85 (br. s., 2H); $^{13}$C NMR (101 MHz, CHLOROFORM-d) δ 146.8, 129.8, 123.6, 118.7, 118.7, 118.0, 105.7, 83.7, 62.3; IR (neat film, cm$^{-1}$): 3426, 3340, 2923, 2852, 2265, 2142, 1630, 1594, 1579, 1513, 1448, 1326, 1313, 1300, 1220, 1164, 993, 882, 862, 784, 680, 534, 456; GC-ESI-HRMS: 142.05310. found 142.05197.

3-(4-Aminophenyl)propiolonitrile (7, APN-p-NH$_2$)

$^1$H NMR (400 MHz, METHANOL-$d_4$) δ 7.26 (d, J=8.6 Hz, 2H), 6.51 (d, J=8.6 Hz, 2H); $^{13}$C NMR (101 MHz,

METHANOL-d₄) δ 152.5, 135.1, 113.6, 105.6, 102.3, 86.3, 60.2; IR (neat film, cm⁻¹): 3431, 3333, 3211, 2250, 2132, 1632, 1599, 1513, 1438, 1303, 1178, 1043, 949, 826, 814, 526, 495, 452; GC-ESI-HRMS: 142.05310. found 142.05464.

3-(o-Tolyl)propiolonitrile (8, APN-o-Me)

¹H NMR (400 MHz, CHLOROFORM-d) δ 7.47 (d, J=7.78 Hz, 1H), 7.28-7.36 (m, 1H), 7.18 (d, J=8.03 Hz, 1H), 7.08-7.16 (m, 1H), 2.39 (s, 3H); ¹³C NMR (101 MHz, CHLOROFORM-d) δ 143.4, 134.1, 131.8, 130.1, 126.1, 117.4, 105.6, 82.4, 66.4, 20.5; IR (neat film, cm⁻¹): 2295, 2257, 2141, 1599, 1484, 1456, 1383, 1291, 1199, 1162, 1116, 1039, 757, 711, 672, 548, 490, 452; GC-ESI-HRMS: 141.05785. found 141.05926.

3-(2,6-Dimethylphenyl)propiolonitrile (9, APN-o,o'-diMe)

¹H NMR (400 MHz, CHLOROFORM-d) δ 7.12-7.27 (t, J=7.5 Hz, 1H), 7.01 (d, J=7.5 Hz, 2H), 2.38 (s, 6H); ¹³C NMR (101 MHz, CHLOROFORM-d) δ 143.8, 131.2, 127.3, 117.6, 105.6, 81.5, 70.2, 20.8; IR (neat film, cm⁻¹): 2923, 2856, 2261, 2138, 1732, 1595, 1468, 1381, 1265, 1168, 1033, 774, 728, 490; GC-ESI-HRMS: 155.07350. found 155.07507.

3-(2-Nitrophenyl)propiolonitrile (10, APN-o-NO₂)

¹H NMR (400 MHz, METHANOL-d₄) δ 8.28-8.35 (m, 1H), 7.96-8.06 (m, 1H), 7.81-7.90 (m, 2H); ¹³C NMR (101 MHz, METHANOL-d₄) δ 151.9, 138.3, 135.2, 134.1, 126.6, 114.2, 105.7, 79.0, 68.6; IR (neat film, cm⁻¹): 2268, 1604, 1567, 1528, 1502, 1480, 1345, 851, 787, 744, 709, 687, 537, 491; GC-ESI-HRMS: 172.02728. found 172.02869.

N-(4-(Cyanoethynyl)phenyl)acetamide (11, APN-p-NHAc)

¹H NMR (400 MHz, METHANOL-d₄) δ 7.56-7.63 (m, J=8.8 Hz, 2H), 7.49-7.56 (m, J=8.8 Hz, 2H), 2.04 (s, 3H); ¹³C NMR (101 MHz, METHANOL-d₄) δ 171.9, 143.8, 135.7, 120.7, 112.8, 106.2, 84.5, 62.7, 24.1; IR (neat film, cm⁻¹): 3303, 3174, 3098, 2278, 2262, 2139, 1670, 1594, 1535, 1407, 1364, 1321, 1263, 1177, 834, 534; GC-ESI-HRMS: 184.06366. found 184.06212.

4-(Cyanoethynyl)-N-methylbenzamide (12, APN-p-CONHMe)

¹H NMR (400 MHz, METHANOL-d₄) δ 7.96-8.05 (m, J=7.78 Hz, 2H), 7.85-7.93 (m, J=7.78 Hz, 2H), 3.03 (s, 3H); ¹³C NMR (101 MHz, METHANOL-d₄) δ 169.1, 138.3, 134.9, 129.0, 121.6, 105.9, 83.0, 64.6, 28.8; IR (neat film, cm⁻¹): 3348, 2270, 1641, 1549, 1502, 1408, 1392, 1327, 1303, 1283, 1162, 854, 760, 617, 488; GC-ESI-HRMS: 184.06366. found 184.06465.

3-(4-Iodophenyl)propiolonitrile (13)

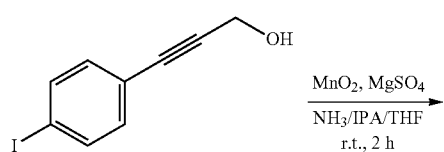

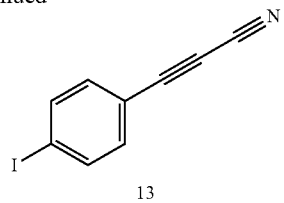

Product was synthesized according to general procedure of MnO₂-oxidation. Reaction time: 30 minutes; yield: 61%.

¹H NMR (400 MHz, CHLOROFORM-d) δ=7.78 (d, J=8.5 Hz, 2H), 7.32 (d, J=8.5 Hz, 3H); ¹³C NMR (101 MHz, chloroform-d) δ 138.1, 134.4, 116.8, 105.2, 99.2, 81.9, 64.2.

Compound 13 can be used for the labeling method according to the invention (with radioisotope 125I).

3-(4-(Trifluoromethyl)phenyl)propiolonitrile (14)

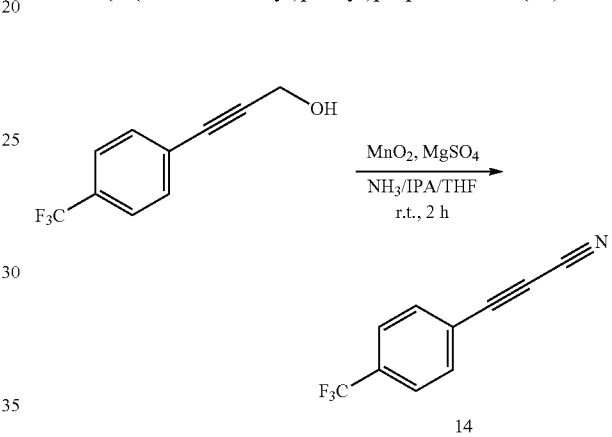

Product was synthesized according to general procedure of MnO₂-oxidation. Reaction time: 1 hour; yield: 45%.

¹H NMR (400 MHz, CHLOROFORM-d) δ=7.76 (d, J=8.3 Hz, 2H), 7.70 (d, J=8.3 Hz, 2H).

Compound 14 can be used for the labeling method according to the invention (with radioisotope 18F).

tert-Butyl 4-(3-hydroxyprop-1-yn-1-yl)benzoate (15a)

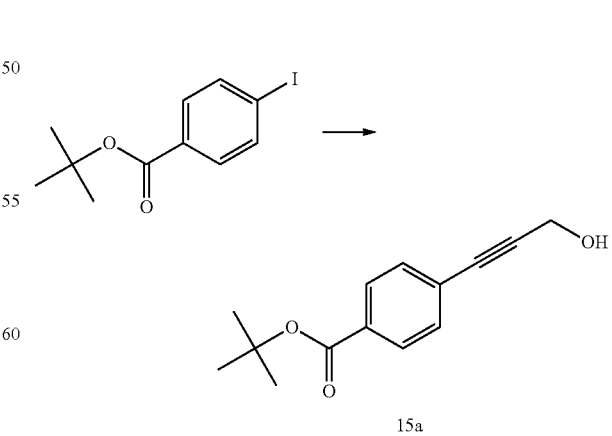

Product was synthesized according to general procedure B for coupling. Yield: 98%.

¹H NMR (400 MHz, CHLOROFORM-d) δ=7.93 (d, J=8.1 Hz, 2H), 7.47 (d, J=8.1 Hz, 2H), 4.53 (s, 2H), 1.60 (s, 9H); ¹³C NMR (101 MHz, CHLOROFORM-d) δ=165.1, 131.7, 131.4, 129.3, 126.6, 89.8, 85.1, 81.4, 51.6, 28.1.

tert-Butyl 4-(cyanoethynyl)benzoate (15)

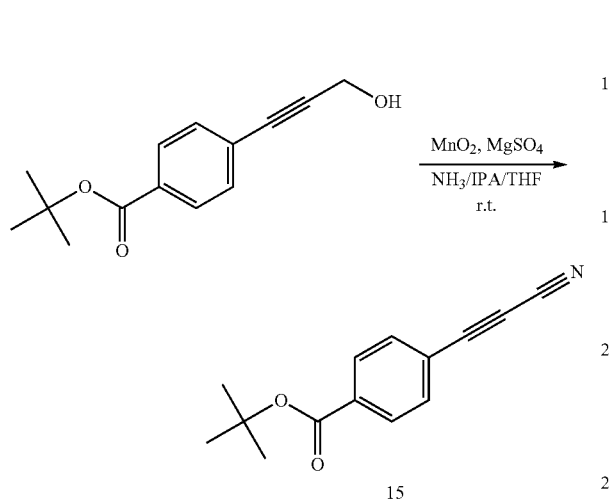

Product was synthesized according to general procedure of MnO₂-oxidation. Reaction time: 15 minutes; yield: 48%.

¹H NMR (400 MHz, DMSO-d₆) δ=8.00 (d, J=8.3 Hz, 2H), 7.94 (d, J=8.3 Hz, 2H), 1.56 (s, 9H); ¹³C NMR (101 MHz, CHLOROFORM-d) δ=164.3, 134.8, 133.3, 129.7, 121.3, 105.2, 82.2, 81.9, 64.8, 28.1.

4-(Cyanoethynyl)benzoic acid (16)

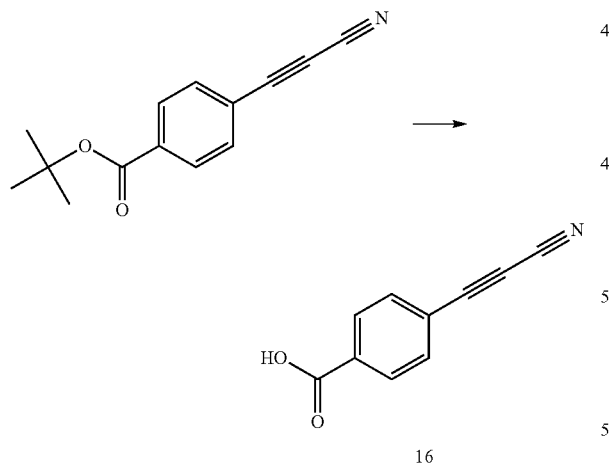

To the solution of tert-butyl 4-(2-cyanoeth-1-yn-1-yl)benzoate (1 eq., 350 mg, 1.54 mmol) in MeCN (14 mL) was added TFA (30.6 eq., 5.372 g, 3.5 mL, 47.1 mmol). The mixture was stirred for 36 h at r.t. and then filtered and washed with 3×2 mL of Et₂O. The precipitate consisted of pure 4-(2-cyanoeth-1-yn-1-yl)benzoic acid (140 mg, 0.823 mmol, 53% yield).

¹H NMR (400 MHz, METHANOL-d₄) δ=8.12 (d, J=8.3 Hz, 3H), 7.83 (d, J=8.3 Hz, 2H).

Perfluorophenyl 4-(cyanoethynyl)benzoate (17)

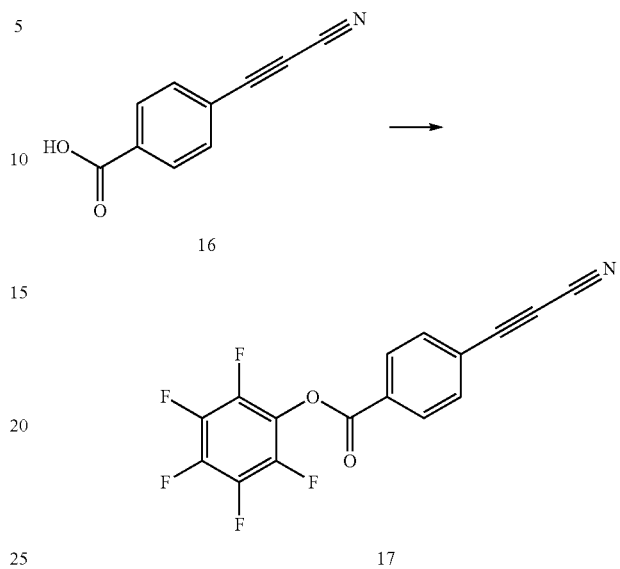

The solution of pentafluorophenol (1 eq., 89.2 mg, 0.484 mmol) and 4-(2-cyanoeth-1-yn-1-yl)benzoic acid (1 eq., 82.9 mg, 0.484 mmol) in THF (4.84 mL) was cooled to 0° C. and DCC (1 eq., 99.9 mg, 0.484 mmol) was added to the mixture. The resulting solution was stirred at r.t. for 14 h, then filtered and washed with Et₂O. The filtrate was evaporated to give pentafluorophenyl 4-(2-cyanoeth-1-yn-1-yl)benzoate (120 mg, 0.358 mmol, 74% yield) as a white solid.

¹H NMR (400 MHz, DMSO-d₆) δ=8.29 (d, J=8.3 Hz, 2H), 8.08 (d, J=8.3 Hz, 2H). Compound 17 can be used for a bio-conjugation method according to the invention.

Sodium 4-((4-(cyanoethynyl)benzoyl)oxy)-2,3,5,6-tetrafluorobenzenesulfonate (18)

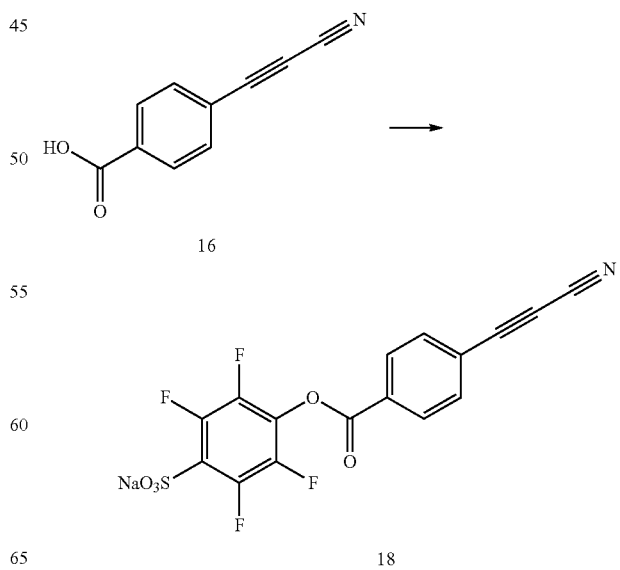

To the solution of 4-(2-cyanoeth-1-yn-1-yl)benzoic acid (1 eq., 54.2 mg, 0.317 mmol) and sodium 2,3,5,6-tetrafluoro-4-hydroxybenzene-1-sulfonate (1 eq., 84.9 mg, 0.317 mmol) in dry DMF (0.792 mL) was added DCC (1 eq., 65.3 mg, 0.317 mmol). The resulting mixture was stirred at r.t. for 36 h, then cooled to 0° C., stirred for 1 h, filtered and washed with 0.8 mL of dry DMF. The filtrate was diluted with 16 mL of Et$_2$O, stirred for 15 min for complete crystallization and the precipitate was filtered to give sodium 4-((4-(cyanoethynyl)benzoyl)oxy)-2,3,5,6-tetrafluorobenzenesulfonate (72.5 mg, 0.172 mmol, 54% yield) as a white solid.

$^1$H NMR (400 MHz, DMSO-d$_6$) δ=8.31 (d, J=6.3 Hz, 2H), 8.09 (d, J=6.3 Hz, 2H). Compound 18 can be used for a bio-conjugation method according to the invention.

N-((1-(4-(cyanoethynyl)phenyl)-1H-1,2,3-triazol-4-yl)methyl)-5-(dimethylamino)naphthalene-1-sulfonamide (20)

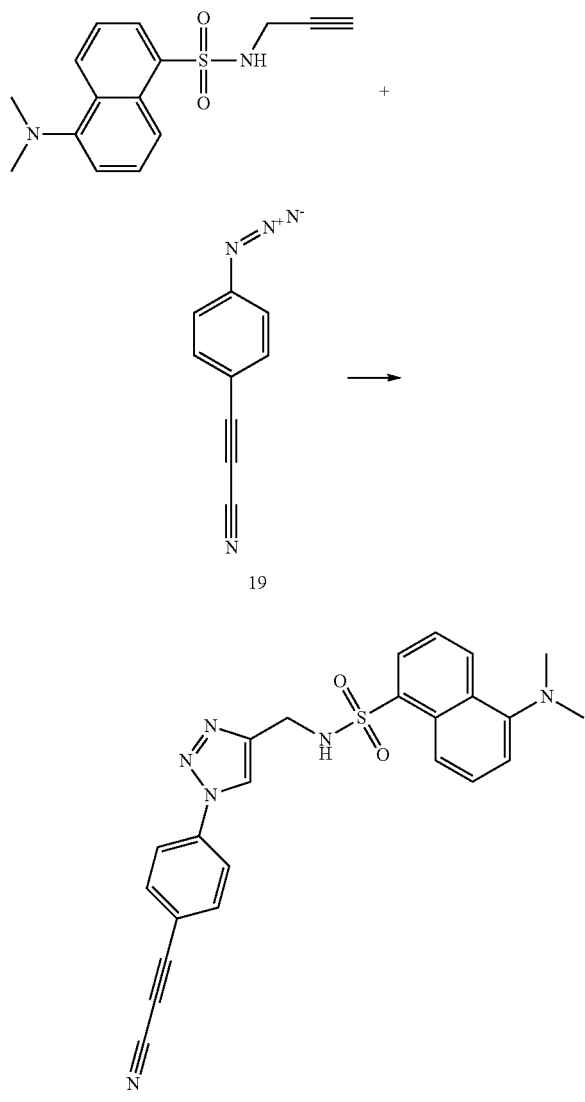

5-(dimethylamino)-N-(prop-2-yn-1-yl)naphthalene-1-sulfonamide (1 eq., 395 mg, 1.37 mmol) and 3-(4-azidophenyl)prop-2-ynenitrile (1 eq., 230 mg, 1.37 mmol) were solubilized in tBuOH (6.91 mL). To this mixture was added a solution of copper sulfate pentahydrate (10%, 34.2 mg, 0.137 mmol) in 0.5 mL of water followed by the solution of sodium ascorbate (0.5 eq., 135 mg, 0.685 mmol) in 0.5 mL of water. The resulting solution was stirred for 2 h and then concentrated on rotary evaporator. The residue was extracted with DCM. The organic layer was washed with saturated aqueous solution of NH$_4$Cl and with water, dried over MgSO$_4$ and evaporated to give 20 (544 mg, 1.19 mmol, 87% yield) as a green solid.

$^1$H NMR (400 MHz, DMSO-d$_6$) δ=8.59 (br. s., 1H), 8.34 (d, J=7.3 Hz, 1H), 8.33 (s, 1H) 8.26 (d, J=8.8 Hz, 1H), 8.13 (d, J=7.3 Hz, 1H), 8.00 (d, J=8.8 Hz, 2H), 7.83 (d, J=8.8 Hz, 2H), 7.61-7.51 (m, 2H), 7.18 (d, J=7.5 Hz, 1H), 4.21 (s, 2H), 2.71 (s, 6H).

$^{13}$C NMR (101 MHz, DMSO-d$_6$) δ=151.2, 144.8, 138.4, 135.7, 135.6, 129.4, 128.9, 128.8, 128.6, 127.8, 123.4, 121.3, 119.9, 119.0, 116.0, 114.9, 105.3, 82.5, 63.1, 44.9, 37.6.

Compound 20 can be used for a detection method (with dyes, for instance) according to the invention.

3-(4-isothiocyanatophenyl)propiolonitrile (21)

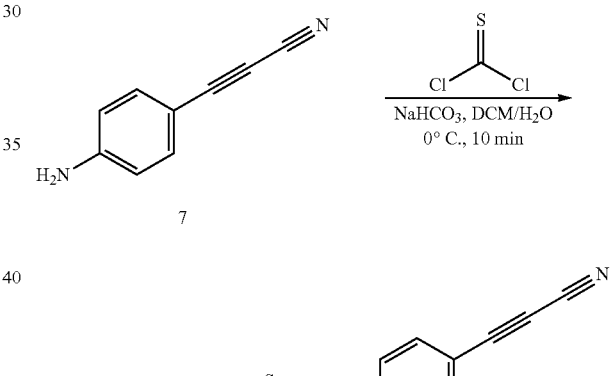

In a 50 mL RB flask, a solution of sodium hydrogen carbonate (886 mg, 10.55 mmol) in 10 mL water was stirred for 10 min and to it dichloromethane (10 mL) was added followed by 3-(4-aminophenyl)prop-2-ynenitrile (500 mg, 3.52 mmol). The reaction mixture was cooled to 0° C., thiophosgene (402 μL, 5.28 mmol) was introduced dropwise over a period of 30 min and continuously stirred at room temperature for 1 h. The organic phase was separated and dried over anhydrous MgSO$_4$. Concentration of the solution afforded pure 21 (609 mg, 3.31 mmol, 94% yield) in form of yellow solid.

$^1$H NMR (400 MHz, ACETONITRILE-d$_3$) δ=7.71 (d, J=8.5 Hz, 2H), 7.37 (d, J=8.5 Hz, 2H).

Compound 21 can be used for a bio-conjugation method according to the invention.

tert-butyl (1-((4-(cyanoethynyl)phenyl)amino)-1-thioxo-6,9,12-trioxa-2-azapentadecan-15-yl)carbamate (22)

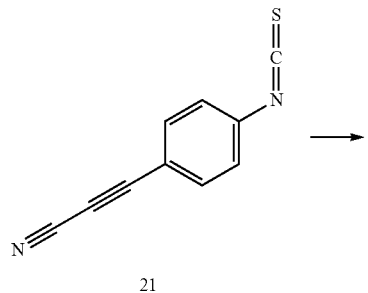

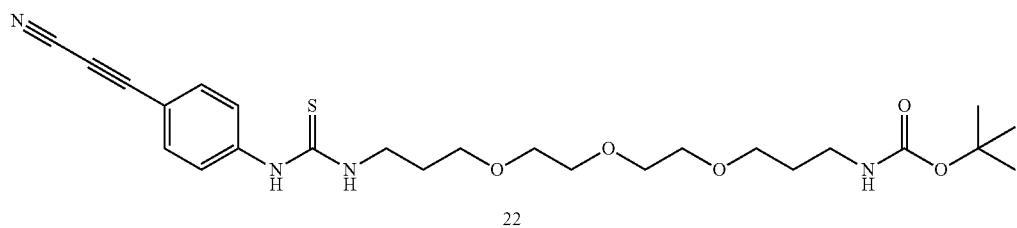

tert-Butyl (3-(2-(2-(3-aminopropoxy)ethoxy)ethoxy)propyl)carbamate (1 eq., 91.5 mg, 0.271 mmol) was dissolved in of DCM (2 mL) and cooled to 0° C. To this solution 3-(4-isothiocyanatophenyl)prop-2-ynenitrile (1 eq., 50 mg, 0.271 mmol) in 1 mL of DCM was slowly added and the mixture was stirred for 30 min. The reaction mix was concentrated to 1 mL and the residue was purified by flash chromatography (DCM/MeOH gradient, 100/0 to 90/10) to give tert-butyl (1-((4-(cyanoethynyl)phenyl)amino)-1-thioxo-6,9,12-trioxa-2-azapentadecan-15-yl)carbamate (126 mg, 0.25 mmol, 92% yield) as a yellow oil.

$^1$H NMR (400 MHz, METHANOL-$d_4$) δ=7.66 (s, 4H), 3.65-3.54 (m, 12H), 3.50 (t, J=6.1 Hz, 2H), 3.12 (t, J=6.8 Hz, 2H), 1.91 (quin, J=6.1 Hz, 2H), 1.72 (quin, J=6.4 Hz, 2H), 1.45 (s, 9H).

$^{13}$C NMR (101 MHz, METHANOL-$d_4$) δ=182.0, 158.5, 144.6, 135.6, 106.4, 84.8, 80.0, 71.6, 71.5, 71.3, 71.3, 70.0, 68.2, 63.0, 38.8, 31.0, 29.8, 29.0

4-(cyanoethynyl)benzoyl chloride (23)

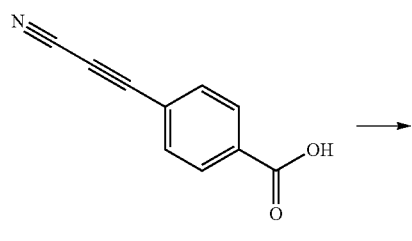

-continued

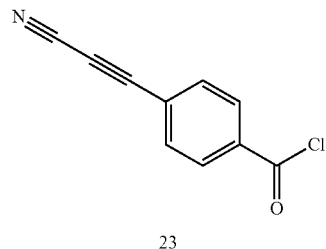

4-(2-cyanoeth-1-yn-1-yl)benzoic acid (1 eq., 30 mg, 0.175 mmol) was dissolved in DCM (2 mL) and SOCl$_2$ (31.5 eq., 400 μL, 5.51 mmol) was added. The mixture was stirred at reflux until the solid completely dissolved and then evaporated to give pure 23 (29.6 mg, 0.156 mmol, 89% yield) as a white solid.

$^1$H NMR (400 MHz, CHLOROFORM-d) δ=8.08 (d, J=8.3 Hz, 2H), 7.67 (d, J=8.3 Hz, 2H).

Compound 23 can be used for a bio-conjugation method according to the invention.

tert-butyl (1-(4-(cyanoethynyl)phenyl)-1-oxo-6,9,12-trioxa-2-azapentadecan-15-yl)carbamate (24)

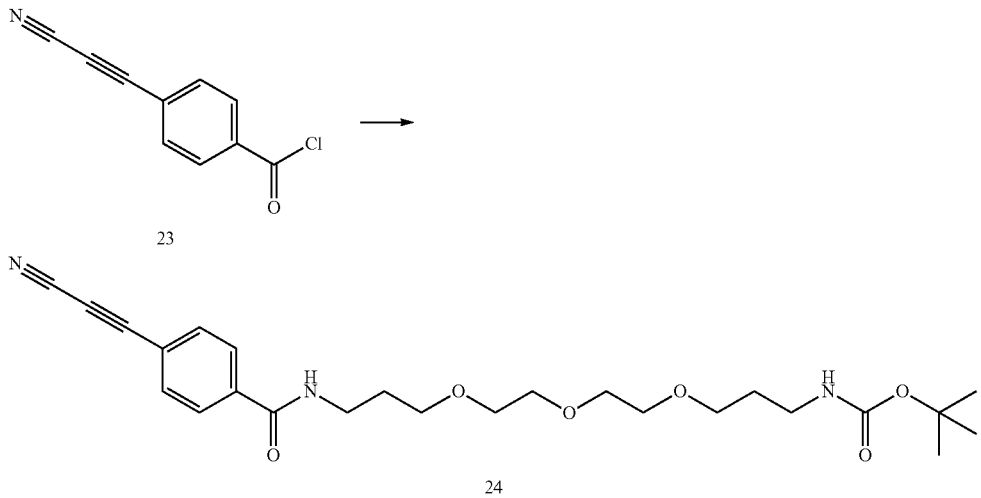

tert-Butyl (3-(2-(2-(3-aminopropoxy)ethoxy)ethoxy)propyl)carbamate (1 eq., 50 mg, 0.156 mmol) and NEt$_3$ (5 eq., 78.9 mg, 0.108 mL, 0.78 mmol) were dissolved in 1 mL of DCM and cooled to −78° C. To this solution was slowly added 23 (1 eq., 29.6 mg, 0.156 mmol) in 1 mL of DCM. The mixture was gradually warmed to r.t. and stirred for 2 h. The reaction mix was then injected into flash chromatography column and eluted with DCM/MeOH (gradient 100/0 to 90/10) to give pure 24 (40.6 mg, 0.086 mmol, 55%) as a yellow oil.

$^1$H NMR (400 MHz, METHANOL-d$_4$) δ=7.92 (d, J=8.3 Hz, 2H), 7.82 (d, J=8.3 Hz, 2H), 3.72-3.45 (m, 14H), 3.12 (t, J=6.8 Hz, 2H), 1.90 (quin, J=6.3 Hz, 2H), 1.72 (quin, J=6.4 Hz, 2H), 1.44 (s, 9H).

4-(cyanoethynyl)-N-(15-oxo-4,7,10-trioxa-14-azanonatriaconta-24,26-diyn-1-yl)benzamide (25)

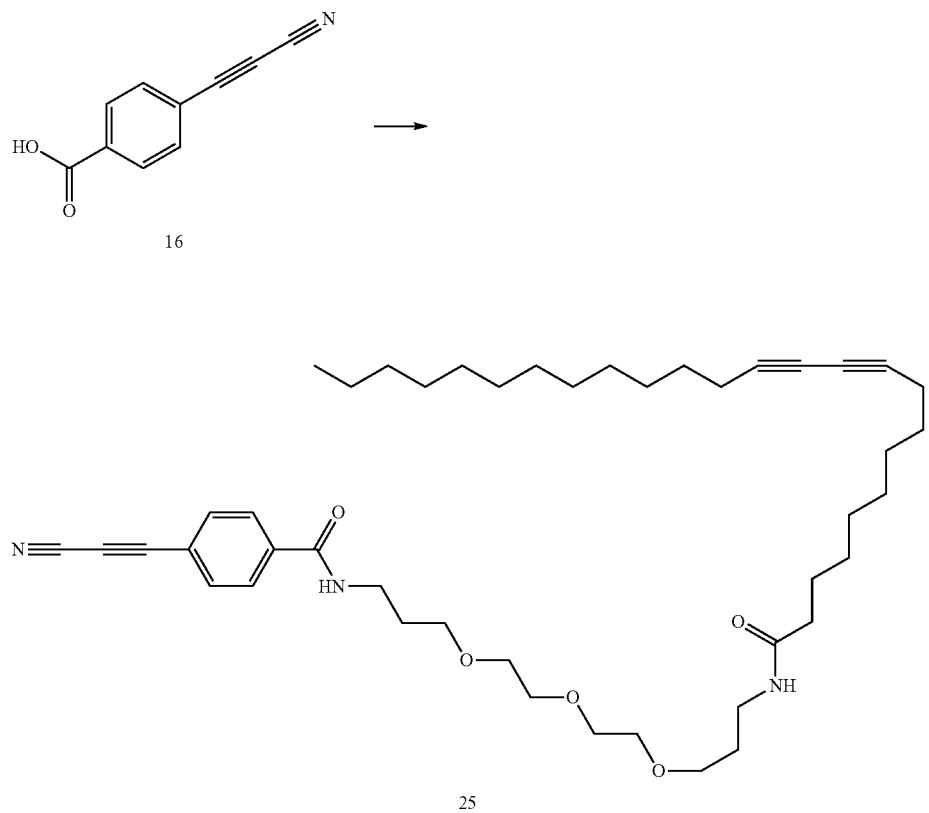

4-(2-cyanoeth-1-yn-1-yl)benzoic acid (1 eq., 29.7 mg, 0.173 mmol) was suspended in DCM and SOCl$_2$ (39.8 eq., 820 mg, 0.5 mL, 6.89 mmol) was added. The mixture was stirred at reflux for 1.5 h, evaporated, dissolved in DCM, and added to the solution of N-(3-{2-[2-(3-aminopropoxy)ethoxy]ethoxy}propyl)pentacosa-10,12-diynamide (1 eq., 100 mg, 0.173 mmol) and TEA (4 eq., 70.2 mg, 0.0964 mL, 0.693 mmol) in DCM at −78° C. The resulting mixture was stirred at r.t. for 1 h and evaporated. The residue was purified by flash chromatography (DCM/MeOH: 10/0 to 9/1) to give the desired product (35.4 mg, 0.0485 mmol, 28% yield) as a yellow oil.

$^1$H NMR (400 MHz, CHLOROFORM-d) δ=7.90 (d, J=8.3 Hz, 2H), 7.67 (d, J=8.3 Hz, 2H), 7.48 (br. s, 1H), 6.18 (br. s, 1H), 3.71-3.45 (m, 14H), 3.32 (t, J=6.0 Hz, 2H), 2.23 (t, J=6.8 Hz, 4H), 2.15 (t, J=7.5 Hz, 2H), 1.90 (td, J=6.0, 11.7 Hz, 2H), 1.73 (quin, J=6.1 Hz, 2H), 1.65-1.42 (m, 6H), 1.41-1.32 (m, 4H), 1.32-1.19 (m, 22H), 0.88 (t, J=6.8 Hz, 3H).

Compound 25 can be used for the labeling (such as photolabeling) method according to the invention or for binding and/or immobilizing compounds.

Ethyl (4-(cyanoethynyl)phenyl)carbamate (26)

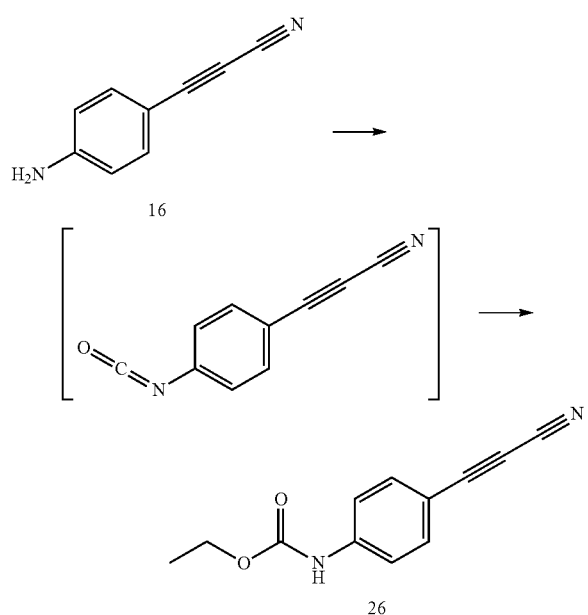

To a solution of triphosgene (1 eq., 49.5 mg, 27.8 μL, 0.167 mmol) in DCM (4 mL) was added a solution of 3-(4-aminophenyl)prop-2-ynenitrile (3 eq., 71.1 mg, 0.5 mmol) in DCM (1 mL). Then triethylamine (6 eq., 101 mg, 138 μL, 1 mmol) in 1 mL of DCM was added dropwise. The mixture was stirred for 15 min allowing the formation of isocyanate intermediate and then ethanol (0.1 mL) was added dropwise. The reaction mixture was stirred for 1 h then washed with 2×5 mL of water and evaporated. The residue was purified by flash chromatography to give ethyl (4-(cyanoethynyl)phenyl)carbamate (102 mg, 0.48 mmol, 96% yield) as a white solid.

$^1$H NMR (400 MHz, CHLOROFORM-d) δ=7.56 (d, J=8.5 Hz, 2H), 7.46 (d, J=8.5 Hz, 2H), 6.79 (br. s, 1H), 4.26 (q, J=7.0 Hz, 2H), 1.33 (t, J=7.0 Hz, 3H).

1-(4-(cyanoethynyl)phenyl)-3-(prop-2-yn-1-yl)urea (27)

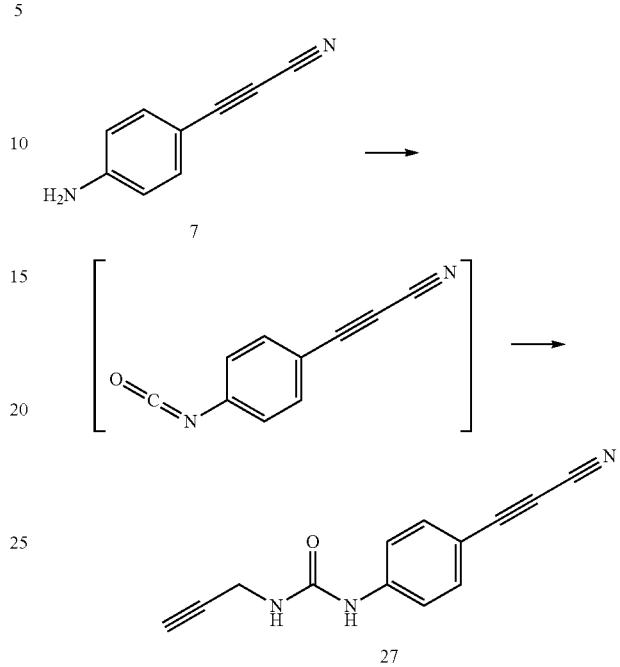

To a solution of triphosgene (1 eq., 49.5 mg, 27.8 μL, 0.167 mmol) in DCM (2 mL) was added a solution of 3-(4-aminophenyl)prop-2-ynenitrile (3 eq., 71.1 mg, 0.5 mmol) in DCM (3 mL). Then triethylamine (6 eq., 101 mg, 138 μL, 1 mmol) was added, the mixture was stirred for 5 min and then were added propargylamine (4.69 eq., 43 mg, 50.1 μL, 0.782 mmol) and triethylamine (2 eq., 33.7 mg, 46.3 μL, 0.333 mmol) in 1 mL of DCM. The reaction mixture was stirred for 1 h then washed with 5 mL of water, dried over MgSO$_4$ and concentrated. The residue was purified by flash chromatography (DCM/MeOH gradient) to give 1-(4-(cyanoethynyl)phenyl)-3-(prop-2-yn-1-yl)urea (94.9 mg, 0.425 mmol, 85% yield) as a white solid.

$^1$H NMR (400 MHz, METHANOL-d$_4$) δ=7.60 (d, J=8.8 Hz, 2H), 7.52 (d, J=8.8 Hz, 2H), 4.00 (d, J=2.4 Hz, 2H), 2.61 (t, J=2.4 Hz, 1H).

Compound 27 can be used for click chemistry according to the invention.

prop-2-yn-1-yl (4-(cyanoethynyl)phenyl)carbamate (28)

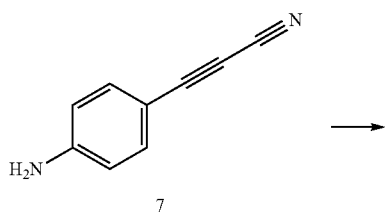

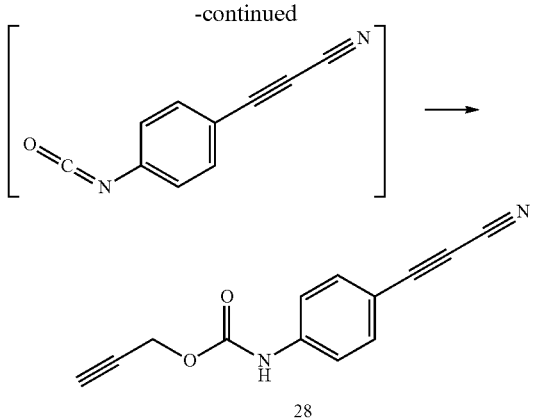

28

To a solution of triphosgene (1 eq., 49.5 mg, 27.8 μL, 0.167 mmol) in DCM (2 mL) was added a solution of 3-(4-aminophenyl)prop-2-ynenitrile (3 eq., 71.1 mg, 0.5 mmol) in DCM (3 mL). Then triethylamine (6 eq., 101 mg, 138 μL, 1 mmol) was added. The mixture was stirred for 5 min and then were added 2-propyn-1-ol (6 eq., 56.1 mg, 59.1 μL, 1 mmol) and triethylamine (2 eq., 33.7 mg, 46.3 μL, 0.333 mmol) in 1 mL of DCM. The reaction mixture was stirred for 1 h then washed with 5 mL of water, dried over MgSO$_4$ and concentrated. The residue was purified by flash chromatography (Cyclohexane/EtOAc gradient) to give prop-2-yn-1-yl (4-(cyanoethynyl)phenyl)carbamate (104 mg, 0.465 mmol, 93% yield) as a white solid.

$^1$H NMR (400 MHz, CHLOROFORM-d) δ=7.57 (d, J=8.6 Hz, 2H), 7.48 (d, J=8.6 Hz, 2H), 4.80 (d, J=2.3 Hz, 2H), 2.54 (t, J=2.3 Hz, 1H).

Compound 28 can be used for click chemistry according to the invention.

bicyclo[6.1.0]non-4-yn-9-ylmethyl (4-(cyanoethynyl)phenyl)carbamate (29)

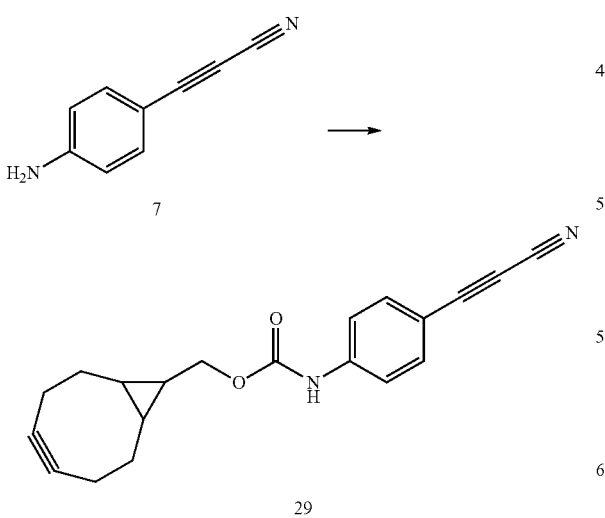

29

To a solution of triphosgene (1 eq., 34.8 mg, 19.5 μL, 0.117 mmol) in DCM (4 mL) was added a solution of 3-(4-aminophenyl)prop-2-ynenitrile (3 eq., 50 mg, 0.352 mmol) in DCM (1 mL). Then triethylamine (6 eq., 71.2 mg, 97.8 μL, 0.703 mmol) was added dropwise. The mixture was stirred for 5 min at r.t. and then bicyclo[6.1.0]non-4-yn-9-ylmethanol (3 eq., 52.8 mg, 0.352 mmol) and triethylamine (2 eq., 23.7 mg, 32.6 μL, 0.234 mmol) were added in 1 mL of DCM. The reaction mixture was stirred at r.t. for 2 hours. After full conversion was confirmed by HPLC the mixture was concentrated to 1 mL volume and purified by flash chromatography (cyclohexane/EtOAc gradient) to give bicyclo[6.1.0]non-4-yn-9-ylmethyl (4-(cyanoethynyl)phenyl)carbamate (68.3 mg, 0.215 mmol, 183%) as a white solid.

$^1$H NMR (400 MHz, CHLOROFORM-d) δ=7.55 (d, J=8.8 Hz, 2H), 7.47 (d, J=8.8 Hz, 2H), 7.09 (br. s, 1H), 2.38-2.14 (m, 6H), 1.67-1.51 (m, 2H), 1.42 (quin, J=8.7 Hz, 1H), 1.04-0.91 (m, 2H).

Compound 29 can be used for click chemistry (such as strain-promoted click) according to the invention.

3-(4-((trimethylsilyl)ethynyl)phenyl)prop-2-yn-1-ol (30a)

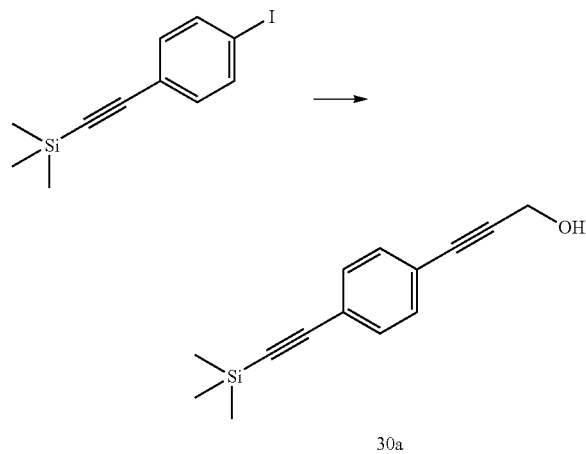

30a

Product was synthesized according to general procedure B for coupling. Yield: 99%.

$^1$H NMR (400 MHz, CHLOROFORM-d) δ=7.41 (d, J=8.4 Hz, 2H), 7.36 (d, J=8.4 Hz, 2H), 4.50 (d, J=5.5 Hz, 2H), 1.89 (t, J=5.5 Hz, 1H), 0.25 (s, 9H).

3-(4-((trimethylsilyl)ethynyl)phenyl)propiolonitrile (30)

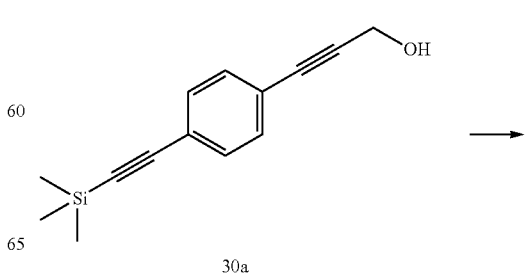

30a

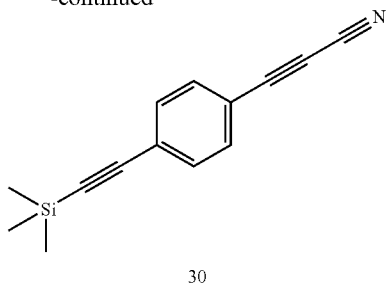

30

Product was synthesized according to general procedure of MnO$_2$-oxidation. Reaction time: 3 hours; yield: 29%.

$^1$H NMR (400 MHz, CHLOROFORM-d) δ=7.55 (d, J=8.4 Hz, 2H), 7.48 (d, J=8.4 Hz, 2H), 0.27 (s, 9H).

$^{13}$C NMR (101 MHz, CHLOROFORM-d) δ=133.2, 132.2, 126.9, 117.1, 105.3, 103.4, 99.4, 82.3, 64.5, −0.3.

3,3'-(5-amino-,3-phenylene)dipropiolonitrile (31)

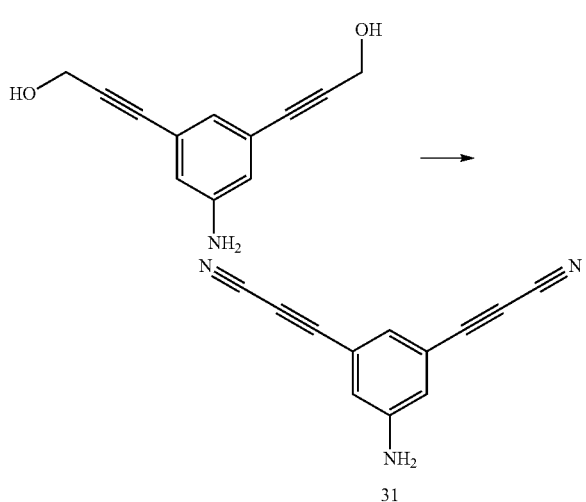

31

Product was synthesized according to general procedure of MnO$_2$-oxidation. Reaction time: 3 hours; yield: 11%.

$^1$H NMR (400 MHz, CHLOROFORM-d) δ=7.20 (t, J=1.3 Hz, 1H), 6.98 (d, J=1.3 Hz, 2H), 4.02 (br. s., 2H).

$^{13}$C NMR (101 MHz, CHLOROFORM-d) δ=147.1, 127.5, 121.6, 119.5, 105.0, 81.0, 63.6.

Compound 31 can be used for rebridging (diAPN) according to the invention.

3-(4-(4,4,5,5-tetramethyl-1,3,2-dioxaborolan-2-yl)phenyl)propiolonitrile (32)

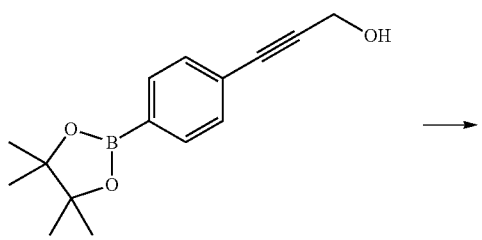

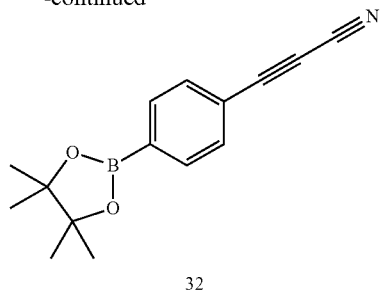

32

Product was synthesized according to general procedure of MnO$_2$-oxidation. Reaction time: 4 hours; yield: 63%.

$^1$H NMR (400 MHz, CHLOROFORM-d) δ=7.84 (d, J=8.2 Hz, 2H), 7.60 (d, J=8.2 Hz, 2H), 1.36 (s, 12H).

3,3'-(1,2-Phenylene)dipropiolonitrile (33)

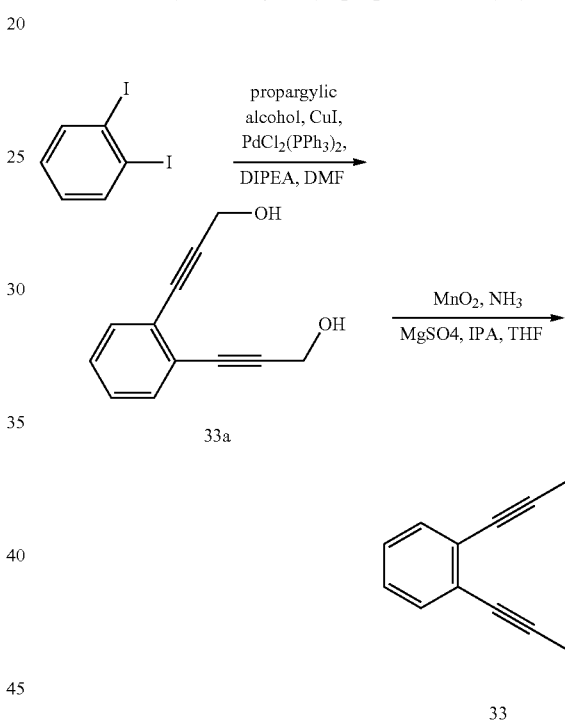

33a: 3,3'-(1,2-Phenylene)bis(prop-2-yn-1-ol)

To the degased solution of 1,2-diiodobenzene (1 eq., 661 mg, 0.262 mL, 2 mmol) and propargylic alcohol (2.3 eq., 272 μL, 4.61 mmol) in butyl amine (15.8 mL), Pd(PPh$_3$)$_4$ (4%, 92.6 mg, 0.0801 mmol) was added and the obtained reaction mass was refluxed overnight. Solvents were evaporated and the obtained crude product was purified by flash chromatography (20 minutes gradient EtOAc/Cyclohexane) to yield 33a (150 mg, 0.8 mmol, 40%) as a brownish solid.

$^1$H NMR (400 MHz, METHANOL-d$_4$) δ 7.38-7.53 (m, 2H), 7.25-7.38 (m, 2H), 4.48 (s, 4H); $^{13}$C NMR (101 MHz, METHANOL-d$_4$) δ 135.6, 131.9, 129.2, 95.6, 86.6, 53.9; ESI-MS: C$_{12}$H$_{11}$O$_2^+$[M+H]$^+$, 187.1. found 187.1.

33: 3,3'-(1,2-Phenylene)dipropiolonitrile

The compound was obtained as the only product of the standard MnO$_2$ oxidation protocol. Reaction time: 75 minutes. Brown solid, yield: 42%.

$^1$H NMR (400 MHz, METHANOL-d$_4$) δ 7.89 (dd, J=3.30, 5.80 Hz, 2H), 7.73 (dd, J=3.30, 5.80 Hz, 2H); $^{13}$C NMR (101 MHz, METHANOL-d$_4$) δ 136.0, 133.5, 126.5, 105.5, 80.2, 67.2; GC-ESI-MS: C$_{12}$H$_5$N$_2$$^+$[M+H]+, 177.0. found 177.0.

3,3'-(1,3-Phenylene)dipropiolonitrile (34)

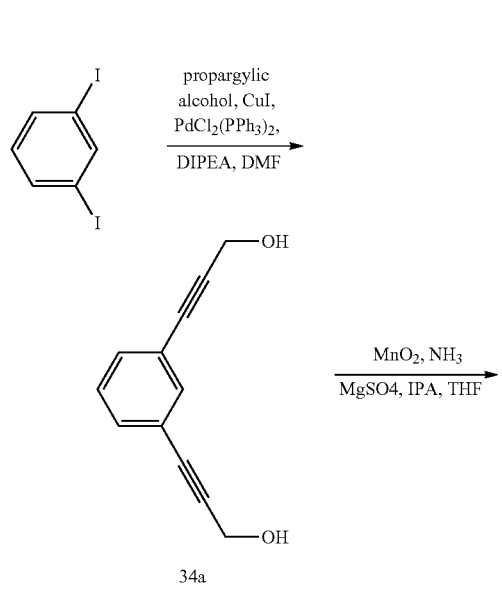

34a: 3,3'-(1,3-Phenylene)bis(prop-2-yn-1-ol)

Same procedure as for the synthesis of 33a. Brownish solid, yield: 55%.

$^1$H NMR (400 MHz, METHANOL-d$_4$) δ 7.47 (s, 1H), 7.36-7.43 (m, 2H), 7.29-7.36 (m, 1H), 4.41 (s, 4H); $^{13}$C NMR (101 MHz, METHANOL-d$_4$) δ 135.3, 132.5, 129.8, 124.8, 89.7, 84.5, 51.2; ESI-MS: C$_{12}$H$_{11}$O$_2$$^+$[M+H]$^+$, 187.1. found 187.0.

34: 3,3'-(1,3-Phenylene)dipropiolonitrile

The compound was obtained as the only product of the standard MnO$_2$ oxidation protocol. Reaction time: 2 hours. Brown solid, yield: 35%.

$^1$H NMR (400 MHz, METHANOL-d$_4$) δ 8.10 (d, J=1.50 Hz, 1H), 7.93 (dd, J=1.50, 8.00 Hz, 1H), 7.63 (t, J=8.00 Hz, 2H); $^{13}$C NMR (101 MHz, METHANOL-d$_4$) δ 139.3, 137.8, 131.2, 120.0, 105.7, 81.7, 64.2; GC-ESI-MS: C$_{12}$H$_5$N$_2$+[M+H]$^+$, 177.0. found 177.1.

3,3'-(1,4-Phenylene)dipropiolonitrile (35)

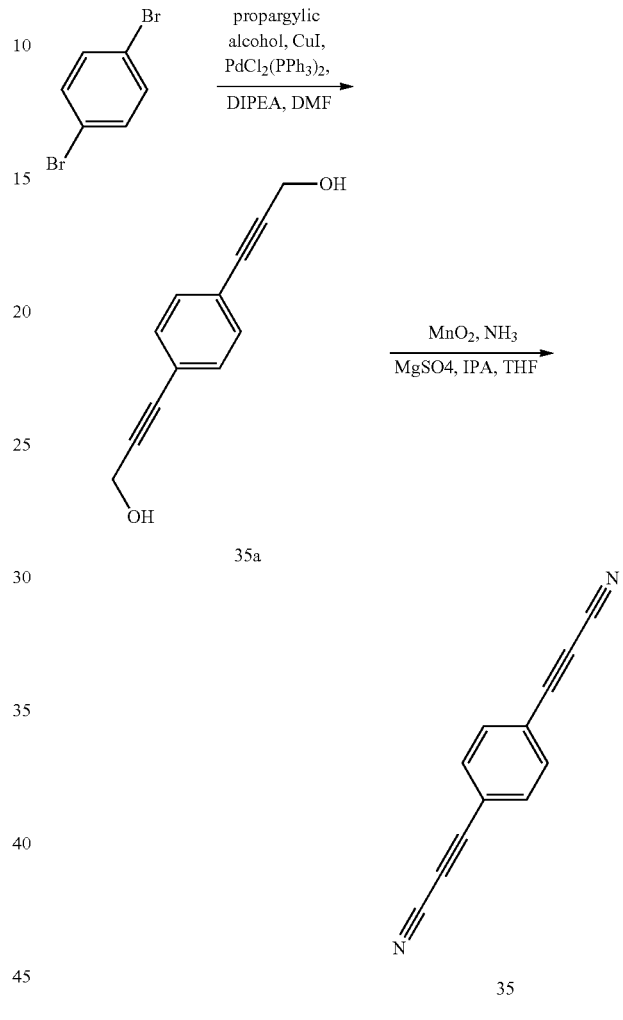

35a: 3,3'-(1,4-Phenylene)bis(prop-2-yn-1-ol)

Same procedure as for the synthesis of 33a, but refluxed for 72 hours. Brownish solid, yield: 35%.

$^1$H NMR (400 MHz, METHANOL-d$_4$) δ 7.39 (s, 4H), 4.41 (s, 4H); $^{13}$C NMR (101 MHz, METHANOL-d$_4$) δ 132.6, 124.3, 101.4, 90.8, 84.9, 51.2; ESI-MS: C$_{12}$H$_{11}$O$_2$$^+$ [M+H]$^+$, 187.1. found 187.1.

35: 3,3'-(1,4-Phenylene)dipropiolonitrile

The compound was obtained as the only product of the standard MnO$_2$ oxidation protocol. Reaction time: 2 hours. Brown solid, yield: 19%.

$^1$H NMR (400 MHz, METHANOL-d$_4$) δ 7.94 (s, 4H); $^{13}$C NMR (101 MHz, METHANOL-d$_4$) δ 135.0, 121.6, 105.5, 82.0, 65.9; GC-ESI-MS: C$_{12}$H$_5$N$_2$$^+$[M+H]$^+$, 177.0. found 177.0.

Compounds 33-35 can be used for rebridging (diAPN) according to the invention.

tert-butyl (S)-2-((tert-butoxycarbonyl)amino)-3-(4-(((trifluoromethyl)sulfonyl)oxy)phenyl)propanoate (36b)

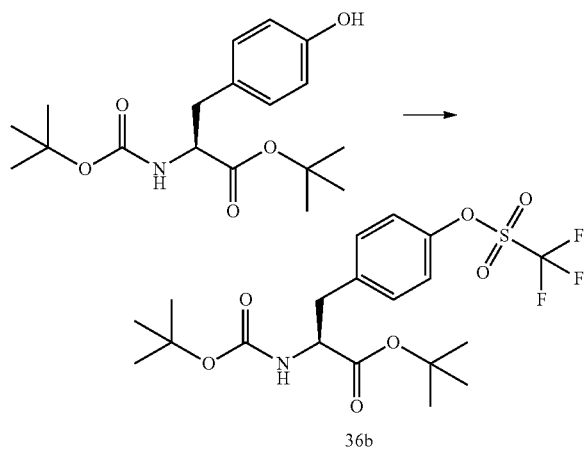

To a cooled to 0° C. solution of tert-butyl 2-{[(tert-butoxy)carbonyl]amino}-3-(4-hydroxyphenyl)propanoate (1 eq., 518 mg, 1.54 mmol) in pyridine (2.5 mL), triflic anhydride 5 (1.1 eq., 476 mg, 0.28 mL, 1.69 mmol) was added dropwise over 20 minutes (using syringe presser). The resulting dark solution was let to warm up to room temperature, poured into water (10 mL), and extracted with ethyl ester (15 mL). The ether extract was washed sequentially with water (5 mL), 1N HCl (2×5 mL), water (5 mL), brine (5 mL), dried over MgSO4, and evaporated to give the targeted product (614 mg, 1.31 mmol, 85%) as a dark-red oil. The product was used in the next step without further purification.

$^1$H NMR (400 MHz, CHLOROFORM-d) δ 7.03-7.18 (m, 3H), 6.82-7.03 (m, 2H), 4.87 (d, J=7.28 Hz, 1H), 4.24 (d, J=7.03 Hz, 1H), 2.65-2.95 (m, 2H), 1.17 (s, 9H), 1.21 (s, 9H).

$^{13}$C NMR (101 MHz, CHLOROFORM-d) δ 170.5, 148.5, 137.3, 131.3, 121.1, 120.3, 117.1, 82.5, 80.0, 54.7, 38.1, 28.3, 27.9.

tert-butyl (S)-2-((tert-butoxycarbonyl)amino)-3-(4-(3-hydroxyprop-1-yn-1-yl)phenyl)propanoate (36a)

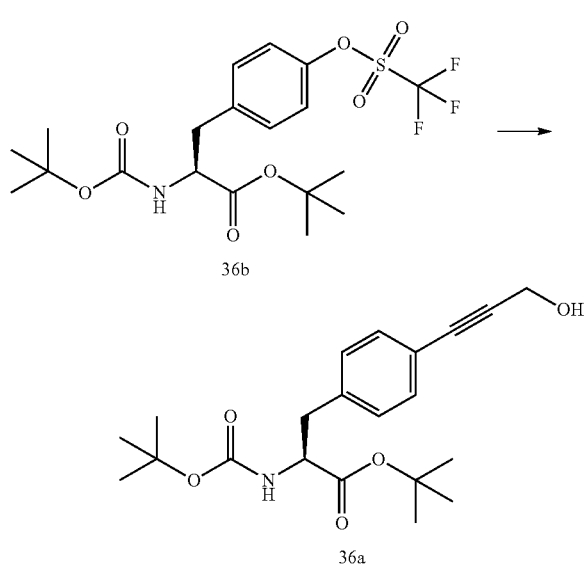

To a solution of phenoltryphlate (1 eq., 136 mg, 0.291 mmol) in morpholine (1 mL) were consequently added PdCl$_2$(PPh$_3$)$_2$(5%, 10.2 mg, 0.0145 mmol), CuI (10%, 5.53 mg, 0.0291 mmol), and propargylic alcohol (2 eq., 32.6 mg, 0.0343 mL, 0.581 mmol). The obtained reaction mixture was degassed and heated at 60° C. for 24 hours. The resulting black solution was poured into water (10 mL), extracted with EtOAc (3×10 mL). The united organic layers were washed with 1N HCl (2×10 mL), water (1×10 mL), dried over MgSO$_4$ and evaporated to give crude product, which after purification by flash chromatography gave the targeted product (8.73 mg, 0.0232 mmol, 8%) as a yellowish solid.

$^1$H NMR (400 MHz, METHANOL-d$_4$) δ 7.30-7.45 (m, J=7.78 Hz, 2H), 7.14-7.30 (m, J=8.03 Hz, 2H), 4.40 (s, 2H), 4.18-4.32 (m, 1H), 3.06 (dd, J=6.27, 13.80 Hz, 1H), 2.91 (dd, J=8.66, 13.68 Hz, 1H), 1.45-1.53 (m, 1H), 1.42 (d, J=3.26 Hz, 19H).

tert-Butyl 2-((tert-butoxycarbonyl)amino)-3-(4-(cyanoethynyl)phenyl)propanoate (36)

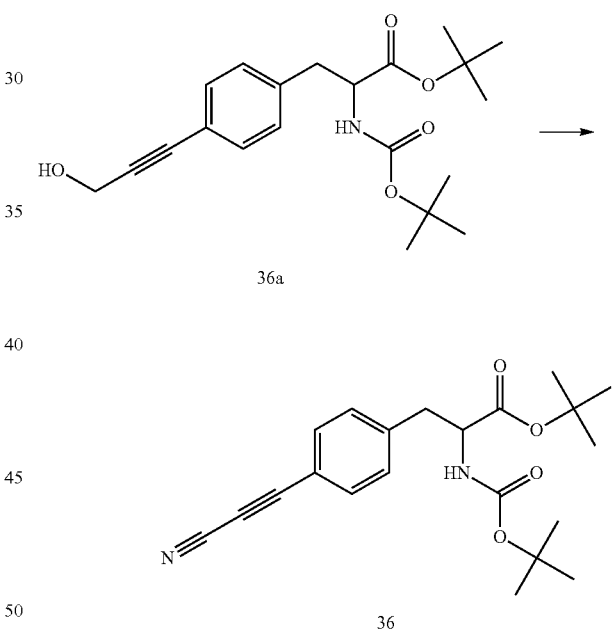

Product was synthesized according to general procedure of MnO$_2$-oxidation. Reaction time: 2 hours; yield: 56%.

$^1$H NMR (400 MHz, CHLOROFORM-d) δ=7.54 (d, J=8.2 Hz, 2H), 7.24 (d, J=8.2 Hz, 2H), 5.05 (d, J=7.3 Hz, 1H), 4.46 (td, J=6.1, 7.3 Hz, 1H), 3.14 (dd, J=6.1, 13.7 Hz, 1H), 3.05 (dd, J=6.1, 13.7 Hz, 1H), 1.42 (s, 9H), 1.41 (s, 9H).

$^{13}$C NMR (101 MHz, CHLOROFORM-d) δ=170.3, 154.9, 141.4, 133.4, 130.1, 115.9, 105.5, 82.9, 82.5, 79.9, 63.2, 54.5, 38.8, 28.3, 27.9.

Compound 36 can be used for purification and/or immobilization according to the invention.

4-(cyanoethynyl)-N-(2-(2-(2-(5-((3aS,4S,6aR)-2-oxohexahydro-1H-thieno[3,4-d]imidazol-4-yl)pentanamido)ethoxy)ethoxy)ethyl)benzamide (37)

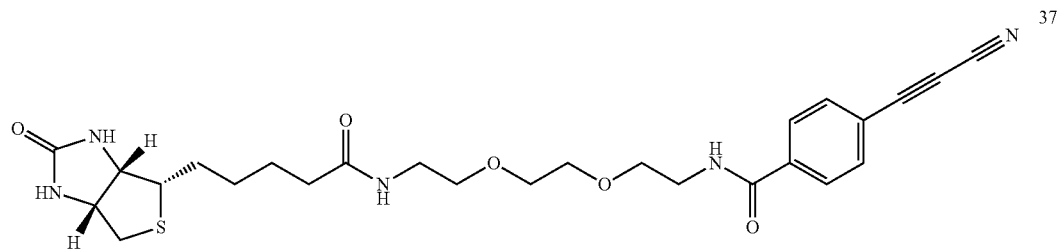 [SMILES: N#CC#Cc1ccc(C(=O)NCCOCCOCCNC(=O)CCCC[C@@H]2SC[C@@H]3NC(=O)N[C@@H]32)cc1]

To the solution of N-(2-(2-(2-aminoethoxy)ethoxy)ethyl)-5-((3aS,4S,6aR)-2-oxohexahydro-1H-thieno[3,4-d]imidazol-4-yl)pentanamide (1 eq., 222 mg, 0.593 mmol) in dry DMF (1 mL) was added sodium 4-((4-(cyanoethynyl)benzoyl)oxy)-2, 3,5,6-tetrafluorobenzenesulfonate (1.2 eq., 300 mg, 0.712 mmol) and DIEA (5.1 eq., 391 mg, 0.5 mL, 3.03 mmol). The mixture was stirred at r.t. for 3 hours and then purified by semi-preparative HPLC to give the desired product (68.8 mg, 0.13 mmol, 22% yield) as a yellow oil.

$^1$H NMR (400 MHz, METHANOL-d$_4$) δ=7.92 (d, J=8.5 Hz, 2H), 7.81 (d, J=8.5 Hz, 2H), 4.49 (dd, J=4.8, 7.8 Hz, 1H), 4.30 (dd, J=4.5, 7.8 Hz, 1H), 3.71-3.56 (m, 8H), 3.54 (t, J=5.5 Hz, 2H), 3.34 (t, J=5.5 Hz, 2H), 3.24-3.14 (m, 1H), 2.92 (dd, J=4.8, 12.8 Hz, 1H), 2.70 (d, J=12.8 Hz, 1H), 2.19 (t, J=7.4 Hz, 2H), 1.78-1.50 (m, 4H), 1.48-1.35 (m, 2H).

$^{13}$C NMR (101 MHz, METHANOL-d$_4$) δ=176.3, 168.8, 166.2, 138.9, 135.0, 129.1, 121.5, 105.9, 83.1, 71.5, 71.4, 70.7, 70.6, 64.6, 63.5, 61.8, 57.1, 41.2, 40.4, 36.9, 29.9, 29.6, 27.0.

2-((4-((4-(Cyanoethynyl)phenyl)amino)-4-oxobutyl)-amino)-2-oxoethyl)tris(2,4,6-trimethoxyphenyl) phosphonium trifluoroacetate (38)

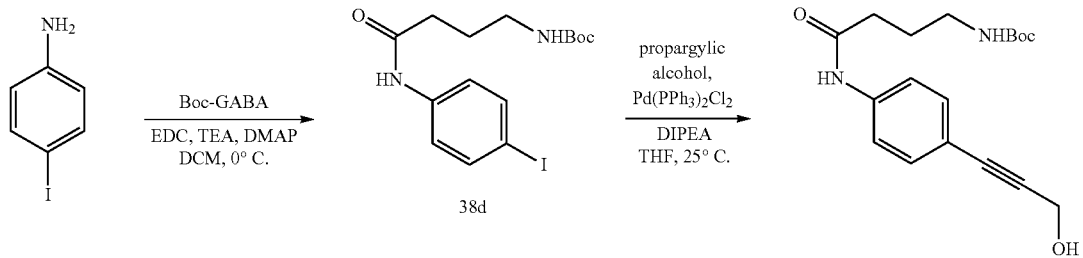

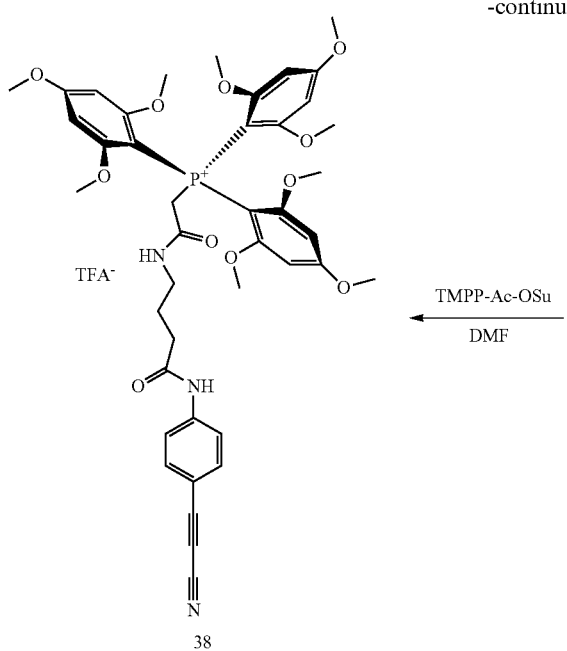

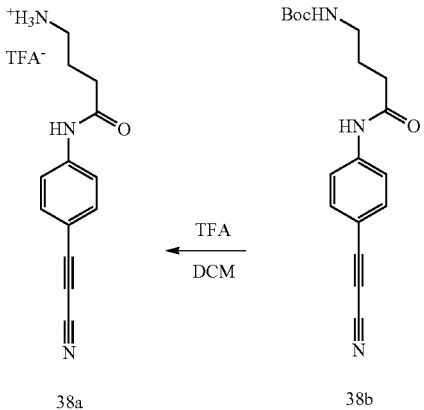

38a           38b

38d: tert-Butyl (4-((4-iodophenyl)amino)-4-oxobutyl)carba-mate

To the cooled to 0° C. solution of Boc-GABA (1 eq., 0.928 g, 4.57 mmol), TEA (3 eq., 1.39 g, 1.9 mL, 13.7 mmol) and DMAP (0.05 eq., 0.0279 g, 0.228 mmol) in DCM (11.7 mL), EDC (1 eq., 0.875 g, 4.57 mmol) was added. The obtained reaction mass was stirred for another 10 minutes at 0° C., an ice bath was removed, and p-iodoaniline (1 eq., 1 g, 4.57 mmol) was added and the reaction was left overnight at 25° C. The obtained reaction mass was washed with 1M HCl (2×20 mL), water (1×20 mL), and dried over $Na_2SO_4$ to give 38d (1125 mg, 2.79 mmol, 61%), which was used without further purification.

$^1$H NMR (400 MHz, CHLOROFORM-d) δ 9.04 (br. s., 1H), 7.58-7.72 (m, J=8.50 Hz, 2H), 7.37-7.51 (m, J=8.50 Hz, 2H), 4.81 (br. s., 1H), 3.27 (m, 2H), 2.30-2.50 (m, 2H), 1.88 (m, 2H), 1.49 (s, 9H); $^{13}$C NMR (101 MHz, CHLOROFORM-d) δ 174.2, 157.4, 137.8, 120.9, 120.0, 87.3, 77.0, 33.1, 32.8, 28.4, 26.0; ESI-MS: $C_{15}H_{22}N_2O_3^+[M+H]^+$, 405.0. found 405.1.

38c: tert-Butyl (4-((4-(3-hydroxyprop-1-yn-1-yl)phenyl)-amino)-4-oxobutyl)carbamate Synthesised following the protocol B for Sonogashira coupling. Yellowish solid, yield: 79%.

$^1$H NMR (400 MHz, METHANOL-d$_4$) δ 7.54-7.58 (m, J=8.50 Hz, 2H), 7.34-7.38 (m, J=8.50 Hz, 2H), 4.40 (s, 2H), 3.13 (t, J=6.90 Hz, 2H), 2.41 (t, J=7.40 Hz, 2H), 1.81-1.89 (m, 2H), 1.44 (s, 9H); $^{13}$C NMR (101 MHz, METHANOL-d$_4$) δ 174.0, 158.6, 140.1, 133.2, 120.8, 119.5, 88.3, 85.3, 80.1, 51.3, 40.9, 35.3, 28.8, 27.1; ESI-MS: $C_{18}H_{25}N_2O_4^+$ $[M+H]^+$, 332.1. found 332.0.

38b: tert-Butyl (4-((4-(cyanoethynyl)phenyl)amino)-4-oxobutyl)carbamate

Synthesised using standard protocol of $MnO_2$ oxidation. Reaction time: 1 hour. White solid, yield: 85%.

$^1$H NMR (400 MHz, METHANOL-d$_4$) δ 7.61-7.65 (m, J=8.80 Hz, 2H), 7.54-7.59 (m, J=8.50 Hz, 2H), 3.04 (t, J=6.85 Hz, 2H), 2.34 (t, J=7.40 Hz, 2H), 1.74-1.81 (m, 2H), 1.34 (s, 9H); $^{13}$C NMR (101 MHz, METHANOL-d$_4$) δ 174.3, 159.1, 143.8, 135.7, 120.8, 112.8, 106.3, 84.6, 62.7, 40.8, 35.3, 34.8, 28.8, 26.9; ESI-MS: $C_{18}H_{22}N_3O_3^+[M+H]^+$, 328.1. found 328.1.

38a: 4-((4-(Cyanoethynyl)phenyl)amino)-4-oxobutan-1-aminium trifluoroacetate

To a suspension of 38b (1 eq., 62.8 mg, 0.192 mmol) in DCM (1 mL), TFA (20 eq., 285 μL, 3.83 mmol) was added and the obtained solution was stirred at 25° C. for 30 minutes. The target product 38a (TFA salt, 65.0 mg, 0.19 mmol, 99%) was obtained after the evaporation of the reaction mass and was used without further purification in the next step.

$^1$H NMR (400 MHz, METHANOL-d$_4$) δ 7.71-7.79 (m, J=9.15 Hz, 2H), 7.63-7.70 (m, J=9.15 Hz, 2H), 3.04 (t, J=6.80 Hz, 2H), 2.6 (t, J=7.05 Hz, 2H), 1.98-2.08 (m, 2H); $^{13}$C NMR (101 MHz, METHANOL-d$_4$) δ 173.1, 143.6, 135.7, 120.7, 112.9, 106.2, 84.5, 62.7, 40.4, 34.5, 24.0; ESI-MS: $C_{13}H_{14}N_3O^+[M+H]^+$, 228.1. found 228.1.

38: (2-((4-((4-(Cyanoethynyl)phenyl)amino)-4-oxobutyl)amino)-2-oxoethyl)tris(2,4,6-trimethoxyphenyl)phosphonium trifluoroacetate To the solution of 38a (1 eq., 10.1 mg, 0.0296 mmol) in DMF (250 μL), TEA (1 eq., 4 μL, 0.0296 mmol) was added. TMPP-Ac-OSu (1 eq., 22.7 mg, 0.0296 mmol) was added to the obtained solution and the reaction mass was for 15 minutes at room temperature. The crude product was purified by HPLC to isolate 38 (9.9 mg, 0.0126 mmol, 42%) as a main product.

$^1$H NMR (400 MHz, METHANOL-d$_4$) δ 7.44-7.59 (m, 4H), 6.13 (d, J=4.52 Hz, 6H), 3.75 (s, 9H), 3.50 (s, 18H), 3.00 (td, J=7.91, 15.31 Hz, 2H), 2.26 (t, J=6.90 Hz, 2H), 1.64-1.75 (m, 2H), 1.25-1.43 (m, 2H); $^{13}$C NMR (101 MHz, METHANOL-$d_4$) δ 174.2, 167.4, 167.4, 165.3, 143.6, 135.8, 120.6, 112.8, 106.3, 92.2 (d, J=8 Hz), 84.5, 62.7, 56.5, 56.2, 37.5, 29.4 (d, J=64 Hz), 27.9, 27.7, 24.9; ESI-HRMS: $C_{42}H_{47}N_3O_{11}P^+$ [M]$^+$, 800.29427. found 800.29401.

(5-((4-(Cyanoethynyl)phenyl)amino)-5-oxopentyl)tris(2,4,6-trimethoxyphenyl)phosphonium bromide (39)

39d: 5-Bromopentanoyl chloride

Degassed solution of 5-bromopentanoic acid (1 eq., 2.85 g, 15.7 mmol) and SOCl$_2$ (1 eq., 1.87 g, 1.14 mL, 15.7 mmol) in DCM (50 mL) was refluxed for 3 hours. The obtained reaction mass was evaporated under reduced pressure to give 39d (3.11 g, 100%) as a yellowish oil. The crude product was used in the next step without purification.

39c: 5-Bromo-N-(4-iodophenyl)pentanamide

Solution of 39d (1 eq., 3.11 g, 15.7 mmol) in DCM (50 mL) was poured into a cooled to −78° C. solution of 4-iodoaniline (1 eq., 3.45 g, 15.7 mmol) and DIPEA (1 eq., 2.03 g, 2.6 mL, 15.7 mmol) in DCM (50 mL). Obtained reaction mass was allowed to warm to room temperature, stirred for another 30 min, washed with 1N HCl (2×25 mL),

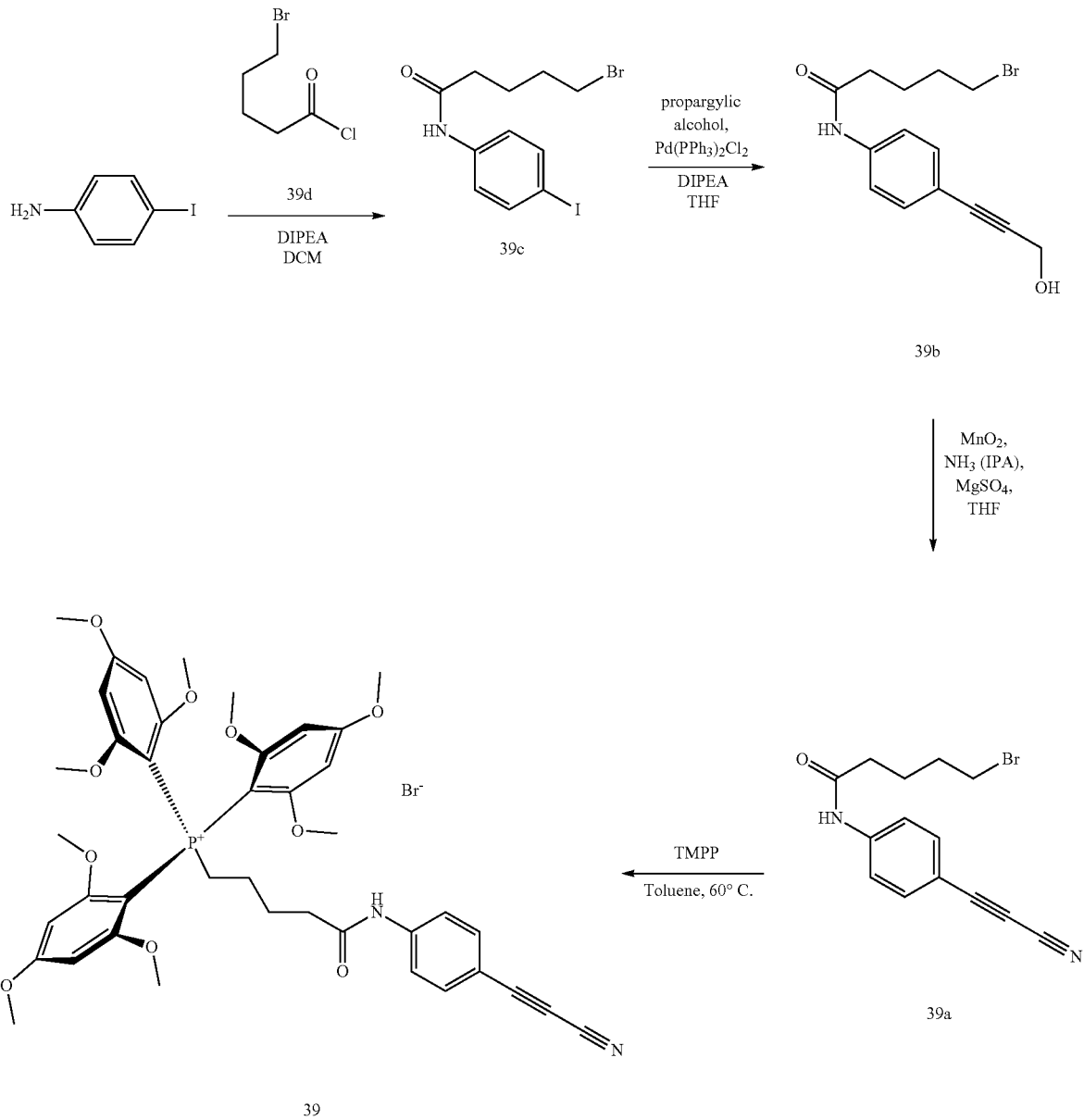

water (1×25 mL), dried over Na$_2$SO$_4$ and evaporated to give 39c (5.60 g, 14.66 mmol, 93%) as brown solid.

$^1$H NMR (400 MHz, METHANOL-$d_4$) δ 7.62-7.66 (m, 2H), 7.38-7.43 (m, 2H), 3.50 (t, J=6.53 Hz, 2H), 2.42 (t, J=7.28 Hz, 2H), 1.81-1.98 (m, 4H), 1.37-1.42 (m, 1H); $^{13}$C NMR (101 MHz, METHANOL-$d_4$) δ 174.0, 140.5, 138.9, 123.1, 87.6, 36.9, 33.8, 33.4, 25.3; ESI-MS: $C_{11}H_{14}BrINO^+$ [M+H]$^+$, 381.9. found 381.8.

39b: 5-Bromo-N-(4-(3-hydroxyprop-1-yn-1-yl)phenyl)pentanamide

Synthesised following the protocol A for Sonogashira coupling. Brown solid, yield: 92%.
$^1$H NMR (400 MHz, METHANOL-d$_4$) δ7.49-7.63 (m, J=8.53 Hz, 2H), 7.32-7.43 (m, J=8.53 Hz, 2H), 4.40 (s, 2H), 4.26 (s, 1H), 3.50 (t, J=6.53 Hz, 2H), 2.43 (t, J=7.15 Hz, 2H), 1.90-2.04 (m, 2H), 1.74-1.90 (m, 2H), 1.32 (s, 1H); $^{13}$C NMR (101 MHz, METHANOL-d$_4$) δ173.9, 140.0, 133.1, 120.7, 119.6, 88.2, 85.2, 51.2, 36.8, 33.7, 33.3, 25.3; ESI-MS: C$_{14}$H$_{17}$BrNO$^+$[M+H]$^+$, 310.0. found 310.0.

39a: 5-Bromo-N-(4-(cyanoethynyl)phenyl)pentanamide 2M solution of NH$_3$ (4 eq., 94.8 mg, 5.56 mmol) in IPA and anhydrous MgSO$_4$ (15 eq., 2511 mg, 20.9 mmol) were added to a stirred solution of 39b (1 eq., 431 mg, 1.39 mmol) in THF (3.42 mL). Activated MnO$_2$ (15 eq., 1814 mg, 20.9 mmol) was added to the solution and the resulting mixture was stirred at room temperature for 4 hours (controlled by TLC, no more starting alcohol; NB: too long reaction time gives hydrolysis product), diluted with DCM (13 mL). The mixture was filtered, washed thoroughly with DCM and the combined filtrates were concentrated under reduced pressure. The solid residue was purified by flash chromatography (EtOAc-cyclohexane, 20 min gradient from 0 to 100% of EtOAc) to give 39 as a white solid (288 mg, 0.946 mmol, 68%).

$^1$H NMR (400 MHz, METHANOL-d$_4$) δ7.69-7.79 (m, J=8.78 Hz, 2H), 7.59-7.69 (m, J=8.78 Hz, 2H), 3.50 (t, J=6.53 Hz, 2H), 1.79-1.99 (m, 4H), 1.26 (t, J=7.15 Hz, 2H); $^{13}$C NMR (101 MHz, METHANOL-d$_4$) δ174.3, 143.8, 135.7, 120.7, 112.8, 106.2, 101.4, 84.6, 37.0, 33.7, 33.4, 25.2. ESI-MS: C$_{14}$H$_{14}$BrN$_2$O$^+$[M+H]$^+$, 304.0. found 304.0.

39: (5-((4-(Cyanoethynyl)phenyl)amino)-5-oxopentyl)tris(2,4,6-trimethoxy-phenyl)phosphonium bromide 39a (1 eq., 20 mg, 0.0655 mmol) and tris(2,4,6-trimethoxy-phenyl)phosphane (TMPP, 1.2 eq., 41.9 mg, 0.0786 mmol) were dissolved in dry toluene (1 mL) and stirred overnight at room temperature. 39 (TFA salt, 22 mg, 39%) was obtained after reverse-phase HPLC as a white solid.

$^1$H NMR (400 MHz, METHANOL-d$_4$) δ 7.51-7.55 (m, 4H), 6.13 (d, J=4.77 Hz, 6H), 3.75 (s, 9H), 3.50 (s, 18H), 3.00 (td, J=6.90, 15.31 Hz, 2H), 2.26 (t, J=6.90 Hz, 2H), 1.73 (m, 2H), 1.22-1.45 (m, 2H); $^{13}$C NMR (101 MHz, METHANOL-d$_4$) δ 174.2, 167.4, 165.3, 143.6, 135.8, 120.6, 112.8, 106.2, 93.6, 92.3, 92.2, 84.5, 62.7, 56.3, 37.5, 29.7, 27.7, 24.9; ESI-HRMS: C$_{41}$H$_{46}$N$_2$O$_{10}$P+[M]$^+$, 757.28846. found 757.29552.

(4-(4-(Cyanoethynyl)benzamido)butyl)tris(2,4,6-trimethoxyphenyl)phosphonium trifluoroacetate (40)

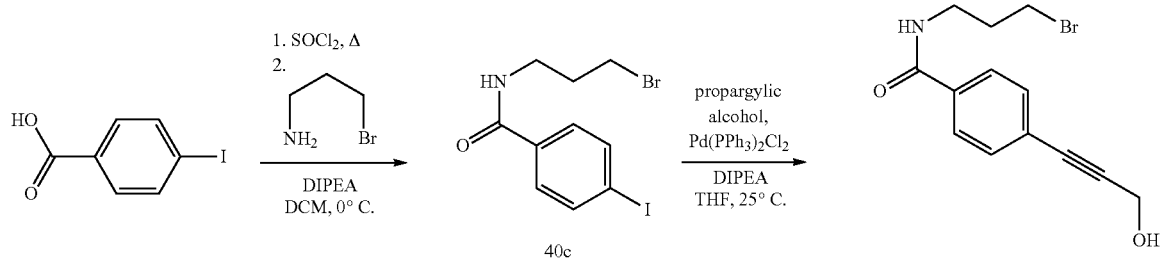

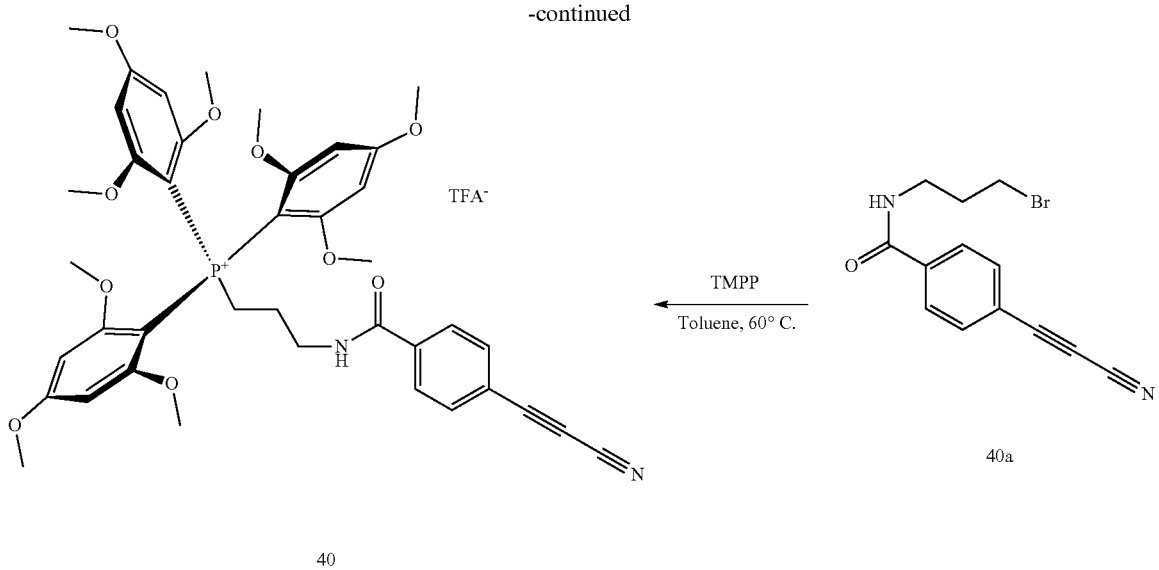

40c: N-(4-Bromobutyl)-4-iodobenzamide 4-iodobenzoic acid (1 eq., 1.45 g, 5.85 mmol) was heated at 110° C. in $SOCl_2$ (9 eq., 3.8 mL, 52.6 mmol) until complete dissolving (around 15 min). Excess of $SOCl_2$ was removed in vacuo and obtained solid was poured into DCM (15 mL), cooled to −78° C. and DIPEA (3.1 eq., 3 mL, 18.2 mmol) was added under vigorous stirring. 3-Bromopropylamine hydrobromide (1.5 eq., 1.90 g, 8.77 mmol) was added to the obtained reaction mass was left stirring for 5 minutes still at −78° C., let to warm up to room temperature, while stirring for another 20 minutes. Ethyl acetate (100 mL) was added with 1M HCl (5 mL), obtained solid was filtered (product), washed with water and dried to yield 40c (2.09 g, 5.67 mmol, 97%) as a white solid.

$^1$H NMR (400 MHz, METHANOL-$d_4$) δ 7.85 (m, J=8.40 Hz, 2H), 7.58 (m, J=8.40 Hz, 2H), 3.48-3.56 (m, 4H), 2.12-2.23 (m, 2H); $^{13}$C NMR (101 MHz, METHANOL-$d_4$) δ 160.1, 139.2, 136.0, 132.8, 102.4, 50.1, 43.2, 23.0; ESI-MS: $C_{10}H_{12}BrINO^+[M+H]^+$, 367.9. found 368.0.

40b: N-(4-Bromobutyl)-4-(3-hydroxyprop-1-yn-1-yl)benzamide

Synthesised following the protocol B for Sonogashira coupling. Brown solid, yield: 81%.

$^1$H NMR (400 MHz, METHANOL-$d_4$) δ 7.73 (m, J=8.40 Hz, 2H), 7.38 (m, J=8.40 Hz, 2H), 4.37 (t, J=5.30 Hz, 2H), 4.34 (s, 2H), 3.51 (t, J=5.80 Hz, 2H), 1.92-1.98 (m, 2H); $^{13}$C NMR (101 MHz, METHANOL-$d_4$) δ 159.2, 134.2, 132.4, 128.2, 127.1, 91.2, 84.8, 67.2, 51.2, 43.3, 22.5; ESI-MS: $C_{13}H_{15}BrNO_2^+[M+H]^+$, 295.0. found 295.0.

40a: N-(3-Bromopropyl)-4-(cyanoethynyl)benzamide

Synthesised using standard protocol of $MnO_2$ oxidation. Reaction time: 45 minutes. Brown solid, yield: 52%.

$^1$H NMR (400 MHz, METHANOL-$d_4$) δ 7.90 (m, J=8.50 Hz, 2H), 7.80 (m, J=8.50 Hz, 2H), 3.42-3.55 (m, 2H), 3.25-3.35 (m, 2H), 2.13-2.23 (m, 2H), 1.92-1.98 (m, 2H); $^{13}$C NMR (101 MHz, METHANOL-$d_4$) δ 168.7, 138.8, 134.9, 128.9, 121.4, 105.8, 83.0, 67.3, 41.9, 39.8, 22.8; ESI-MS: $C_{13}H_{12}BrN_2O^+[M+H]^+$, 291.0. found 291.2.

40: (4-(4-(Cyanoethynyl)benzamido)butyl)tris(2,4,6-trimethoxyphenyl)phosphonium trifluoroacetate 40a (1 eq., 30 mg, 0.103 mmol) and tris(2,4,6-trimethoxyphenyl)phosphane (TMPP, 1 eq., 54.9 mg, 0.103 mmol) were dissolved in dry toluene (2 mL). The obtained solution was left overnight at room temperature. The precipitate was filtered, resolubilised in DMSO, and purified by HPLC to give 40 (35 mg, 0.0409 mmol, 40%) as a white solid.

$^1$H NMR (400 MHz, METHANOL-$d_4$) δ7.75 (d, J=8.50 Hz, 2H), 7.69 (d, J=8.50 Hz, 2H), 6.16 (d, J=4.70 Hz, 2H), 3.76 (s, 9H), 3.51 (s, 18H), 3.35 (t, J=7.10 Hz, 2H), 2.98-3.10 (m, 2H), 1.53-1.64 (m, 2H); $^{13}$C NMR (101 MHz, METHANOL-$d_4$) δ 168.5, 167.5, 165.3, 138.7, 134.9, 128.8, 121.2, 105.8, 94.0, 92.9, 92.3, 82.9, 64.5, 56.5, 41.7, 27.8, 25.7; ESI-HRMS: $C_{40}H_{44}N_2O_{10}P^+[M]^+$, 743.22728. found 743.23946.

Compounds 38-40 can be used for detection and/or separation method according to the invention.

3-(4-(2,5-Dioxo-2,5-dihydro-1H-pyrrol-1-yl)phenyl)propiolonitrile (41)

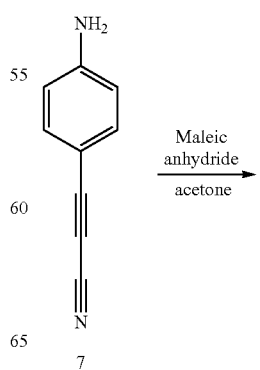

-continued

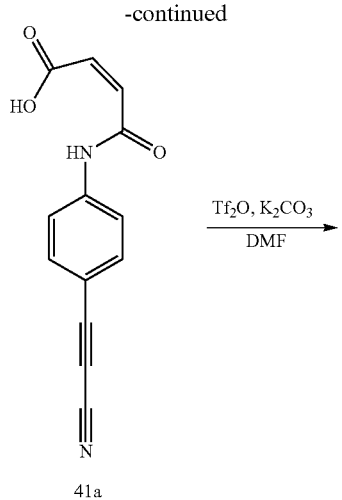

41a

41a: (Z)-4-((4-(Cyanoethynyl)phenyl)amino)-4-oxobut-2-enoic acid

To the solution of 7 (1 eq., 76.8 mg, 0.541 mmol) in acetone (2 mL), maleic anhydride (2 eq., 106 mg, 1.08 mmol) was added. A yellowish solid was obtained after about 7 hours of stirring. The reaction mass was evaporated, an excess of maleic anhydride and maleic acid was washed with methanol. 41a (127 mg, 0.53 mmol, 98%) was obtained as yellowish solid, no further purification was needed.

$^1$H NMR (400 MHz, DMSO-$d_6$) δ 12.90 (br. s., 1H), 10.70 (s, 1H), 7.62-7.90 (m, 4H), 6.50 (d, J=11.90 Hz, 1H), 6.34 (d, J=11.90 Hz, 1H); $^{13}$C NMR (101 MHz, DMSO-$d_6$) δ 166.8, 163.8, 142.4, 135.0, 131.7, 130.1, 119.3, 110.2, 105.6, 84.3, 61.9; ESI-MS: $C_{13}H_7N_2O_3^-$ [M−H]$^-$, 239.0. found 239.0.

41: 3-(4-(2,5-Dioxo-2,5-dihydro-1H-pyrrol-1-yl)phenyl)-propiolonitrile

To the solution of 41a (1 eq., 75 mg, 0.312 mmol) in dry DMF (1.21 mL) trifluoroacetic anhydride (2 eq., 86.9 µL, 0.624 mmol) was added. Stirring continued for another 5 minutes at room temperature and $K_2CO_3$ (3 eq., 129 mg, 0.937 mmol) was added. The reaction mass stirred for another 60 minutes, then directly purified by HPLC to give 41 (65.9 mg, 0.297 mmol, 95%) as a slightly yellow solid.

$^1$H NMR (400 MHz, DMSO-$d_6$) δ 7.81 (m, J=8.50 Hz, 2H), 7.52 (m, J=8.50 Hz, 2H), 6.96 (s, 2H); $^{13}$C NMR (101 MHz, DMSO-$d_6$) δ169.0, 134.4, 134.0, 126.0, 117.3, 117.0, 82.2, 78.5, 62.3; ESI-MS: $C_{13}H_7N_2O_2^+$[M+H]$^+$, 223.0. found 229.9.

Compound 41 can be used for a bioconjugation method according to the invention.

2,5-Dioxopyrrolidin-1-yl 5-((4-(cyanoethynyl)-phenyl)-amino)-5-oxopentanoate (42)

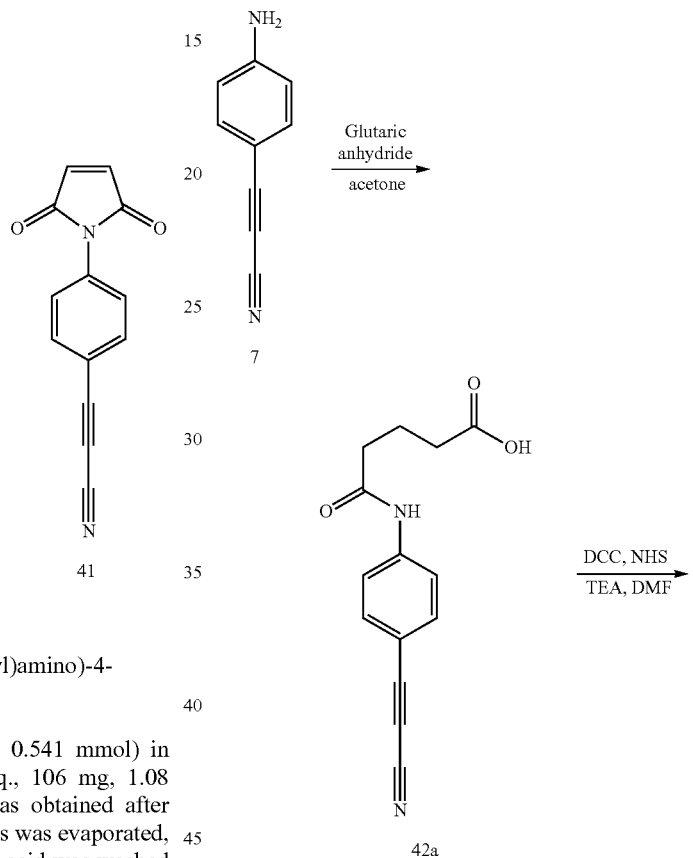

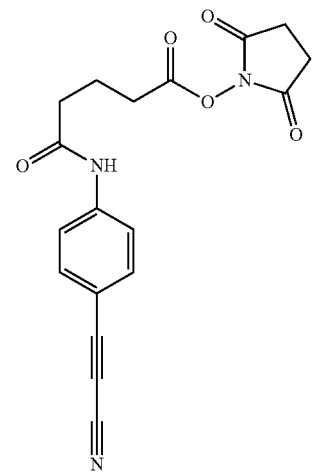

42

42a: 5-((4-(Cyanoethynyl)phenyl)amino)-5-oxopentanoic acid

To a solution of 7 (1 eq., 200 mg, 1.41 mmol) in acetone (1 mL), glutaric anhydride (2 eq., 321 mg, 2.81 mmol) was added. The obtained solution was stirred for 24 hours at room temperature. Acetone was evaporated, the crude product was recrystallised from IPA-cyclohexane to give 42a (324 mg, 1.27 mmol, 90%) as a grey solid.

$^1$H NMR (400 MHz, DMSO-$d_6$) δ10.21 (s, 1H), 8.15 (br. s., 1H), 7.60 (d, J=8.72 Hz, 2H), 7.52 (d, J=8.72 Hz, 2H), 2.52-2.62 (m, 4H), 2.22-2.32 (m, 2H); $^{13}$C NMR (101 MHz, DMSO-$d_6$) δ170.0, 168.5, 140.9, 134.2, 119.0, 111.9, 105.4, 84.1, 63.3, 30.1, 29.0, 21.2; ESI-MS: $C_{14}H_{11}N_2O_3^-[M-H]^-$, 255.1. found 255.1.

42: 2,5-Dioxopyrrolidin-1-yl 5-((4-(cyanoethynyl)phenyl)-amino)-5-oxopentanoate To a solution of 42a (1 eq., 18 mg, 0.0702 mmol) in DCM (1 mL), DCC (1.02 eq., 14.8 mg, 0.0716 mmol) and TEA (1 eq., 6.52 mg, 0.00895 mL, 0.0644 mmol) were added. The obtained reaction mass was stirred for 5 minutes, NHS (1 eq., 8.08 mg, 0.0702 mmol) was added. The resulting solution stirred for another 2 hours at room temperature. The crude product was purified by flash chromatography (cyclohexane-EtOAc) to give 42 (6.45 mg, 0.0183 mmol, 26%) as a white solid.

$^1$H NMR (400 MHz, CHLOROFORM-d) δ 8.27 (br. s., 1H), 7.64 (d, J=8.78 Hz, 2H), 7.57 (d, J=8.78 Hz, 2H), 2.94 (s, 4H), 2.74 (t, J=6.53 Hz, 2H), 2.52 (t, J=6.90 Hz, 2H), 2.23 (m, 2H); $^{13}$C NMR (101 MHz, CHLOROFORM-d) δ 170.3, 169.5, 168.2, 141.3, 134.6, 119.4, 112.4, 105.7, 83.2, 62.9, 35.6, 29.9, 25.7, 21.2; ESI-MS: $C_{18}H_{16}N_3O_{5+}[M+H]^+$, 353.1. found 353.2.

Compound 42 can be used for a bioconjugation method according to the invention.

3-(4-azidophenyl)propiolonitrile (43)

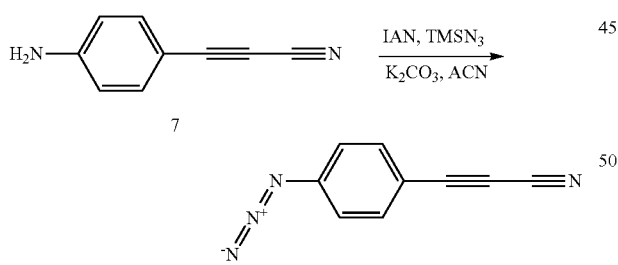

7 (1 eq., 151 mg, 1.07 mmol) was dissolved in acetonitrile (2.34 mL) in a 25 mL roundbottomed flask and cooled to 0° C. in an ice bath. To this stirred mixture was added isoamyl nitrite (IAN, 1.5 eq., 215 µL, 1.6 mmol) followed by trimethylsilyl azide (1.2 eq., 147 mg, 0.168 mL, 1.28 mmol) dropwise. The resulting solution was stirred at room temperature for 45 minutes. The reaction mixture was concentrated under vacuum and the crude product was resolubilised in EtOAc, washed with water, dried and evaporated to give 43 (177 mg, 1.06 mmol, 99%).

$^1$H NMR (400 MHz, ACETONITRILE-$d_3$) δ 7.58-7.81 (m, J=8.78 Hz, 2H), 7.11-7.26 (m, J=8.78 Hz, 2H); $^{13}$C NMR (101 MHz, ACETONITRILE-$d_3$) δ 144.9, 136.0, 120.4, 113.6, 105.9, 83.4, 62.9; GC-ESI-MS: $C_9H_5N_4^+[M+H]^+$, 169.0. found 169.0.

5-Azido-N-(4-(cyanoethynyl)phenyl)pentanamide (44)

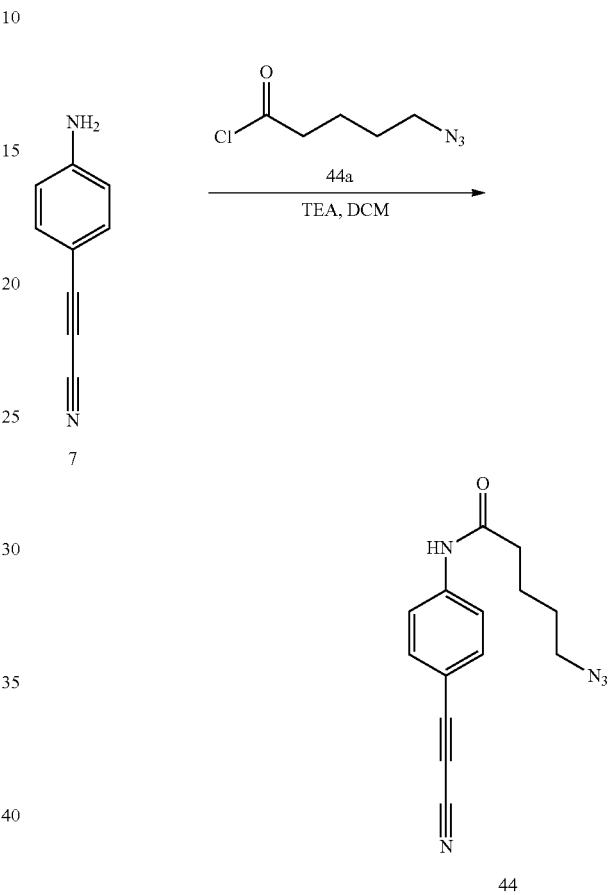

44a: 5-Azidopentanoyl chloride 5-azidopentanoic acid (1 eq., 1.1 g, 6.99 mmol) was refluxed in $SOCl_2$ (10 eq., 5.1 mL, 69.9 mmol) for 30 minutes. Excess of $SOCl_2$ was removed in vacuo and the obtained crude solid was used in the next step without purification.

44: 5-Azido-N-(4-(cyanoethynyl)phenyl)pentanamide 7 (1 eq., 16.1 mg, 0.113 mmol) and TEA (1.5 eq., 24 µL, 0.17 mmol) were dissolved in DCM (3 mL), cooled to −78° C., and 44a (1.1 eq., 20.1 mg, 0.125 mmol) was added to the reaction mixture that was then left to warm to room temperature while stirring for another 1 hour. The reaction mass was washed with 1M HCl (2×1 mL), water (2 mL), dried over $Na_2SO_4$, and evaporated to give crude product, which was purified by flash chromatography to give 44 (25.5 mg, 0.101 mmol, 89%) as a grey solid.

$^1$H NMR (400 MHz, METHANOL-$d_4$) δ 7.58-7.67 (m, J=8.70 Hz, 2H), 7.40-7.58 (m, J=8.70 Hz, 2H), 3.23-3.28

(m, 2H), 2.34 (t, J=7.28 Hz, 2H), 1.61-1.72 (m, 2H), 1.49-1.61 (m, 2H); $^{13}$C NMR (101 MHz, METHANOL-d$_4$) δ173.0, 144.0, 135.7, 134.3, 120.7, 113.0, 106.2, 84.5, 40.4, 34.4, 28.8, 24.0; ESI-MS: $C_{14}H_{14}N_5O^+[M+H]^+$, 268.1. found 268.1.

1-[4-(Cyanoethynyl)benzyl]-3,3,6,6-tetramethyl-4,5-didehydro-2,3,6,7-tetrahydrothiepinium triflate (45)

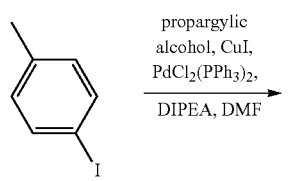

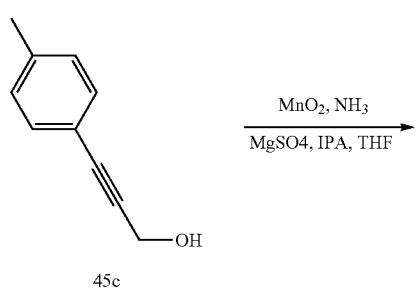

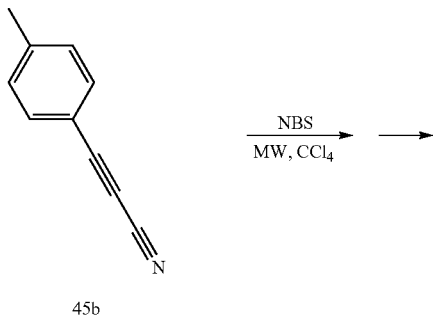

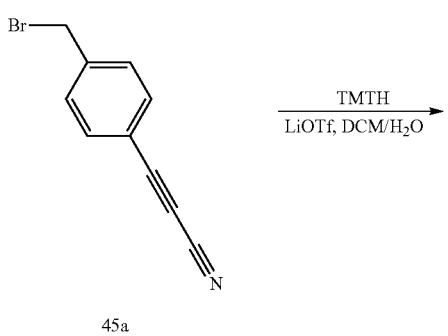

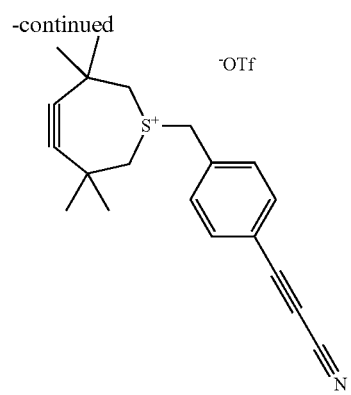

45

45c: 3-(p-Tolyl)prop-2-yn-1-ol

Synthesised using protocol A for Sonogashira coupling. Yellowish solid, yield: 88%.

$^1$H NMR (400 MHz, ACETONITRILE-d$_3$) δ 7.25-7.49 (m, J=8.03 Hz, 2H), 7.04-7.25 (m, J=8.03 Hz, 2H), 4.34 (d, J=6.02 Hz, 2H), 3.31 (t, J=6.02 Hz, 1H), 2.32 (s, 3H); $^{13}$C NMR (101 MHz, ACETONITRILE-d$_3$) δ139.8, 132.4, 130.3, 120.8, 88.8, 85.1, 51.2, 21.5; ESI-MS: $C_{10}H_{11}O^+[M+H]^+$, 146.1. found 146.0.

45b: 3-(p-Tolyl)propiolonitrile

The compound was obtained as the only product of the standard MnO$_2$ oxidation protocol. Reaction time: 3 hours. White solid, yield: 67%.

$^1$H NMR (400 MHz, METHANOL-d$_4$) δ7.37-7.59 (m, J=8.03 Hz, 2H), 7.02-7.31 (m, J=8.03 Hz, 2H), 2.29 (s, 3H); $^{13}$C NMR (101 MHz, METHANOL-d$_4$) 143.2, 133.3, 129.5, 114.0, 104.8, 83.2, 61.3, 20.4; ESI-MS: $C_{10}H_8N^+[M+H]^+$, 141.1. found 141.0.

45a: 3-(4-(Bromomethyl)phenyl)propiolonitrile

Degased solution of 45b (1 eq., 68 mg, 0.482 mmol) in DCM (1 mL) was MW-irradiated (100° C.) for 5 minutes. The reaction mixture was evaporated, the crude was purified by preparative HPLC to give 45a (42.4 mg, 0.193 mmol, 40%) as a yellowish solid.

$^1$H NMR (400 MHz, CHLOROFORM-d) δ 7.56-7.71 (m, J=8.28 Hz, 2H), 7.40-7.49 (m, J=8.28 Hz, 2H), 4.48 (s, 2H); $^{13}$C NMR (101 MHz, CHLOROFORM-d) 141.8, 133.9, 129.5, 117.5, 105.3, 82.3, 63.7, 31.8; GC-ESI-MS: $C_{10}H_7BrN^+[M+H]^+$, 219.0. found 219.0.

45: 1-[4-(Cyanoethynyl)benzyl]-3,3,6,6-tetramethyl-4,5-didehydro-2,3,6,7-tetrahydrothiepinium triflate To a degassed solution of 45a (1 eq., 43.7 mg, 0.199 mmol) and TMTH (1.29 eq., 43 mg, 0.255 mmol; synthesised following previously described procedure[83.1]) in DCM (1.34 mL), a solution of LiOTf (11.6 eq., 360 mg, 2.31 mmol) in distilled and degased H$_2$O (0.668 mL) was added. The obtained biphasic mixture was vigorously stirred for 5 days at 25° C. (degasing once per day). Two phases were separated, the organic one was washed with DCM (5×2 mL). United organic fractions were evaporated and the crude was purified by HPLC to give 45 (46.9 mg, 0.111 mmol, 56%) as colourless oil (crystallizes slowly at 0° C. to yield a white solid).

$^1$H NMR (400 MHz, CHLOROFORM-d) δ7.65-7.73 (m, J=8.03 Hz, 2H), 7.56-7.65 (m, J=8.03 Hz, 2H), 5.07 (s, 2H), 4.12 (d, J=12.30 Hz, 2H), 3.72 (d, J=12.30 Hz, 2H), 1.36 (s, 6H), 1.30 (s, 6H); $^{13}$C NMR (101 MHz, DMSO-d$_6$) δ135.1, 133.6, 131.9, 117.8, 106.4, 105.8, 83.3, 63.6, 60.1, 43.2, 34.6, 26.4, 25.4; HR-ESI-MS: C$_{20}$H$_{22}$NS$^+$[M]$^+$, 308.1. found 308.1.

Compounds 43-45 can be used for a click chemistry (such as reaction click—azide) according to the invention.

Compound 45 can be used for strain promoted click according to the invention.

1-({4-[1-{[2-({3-Carboxylato-4-[6-(dimethylamino)-3-(dimethyliminiumyl)-3H-xanthen-9-yl]phenyl}formamido)ethyl]sulfanyl}-2-cyanoeth-1-en-1-yl]phenyl}methyl)-3,3,6,6-tetramethyl-1-thiacyclohept-4-yn-1-ium trifluoroacetate (46)

46a: 2-(6-(Dimethylamino)-3-(dimethyliminio)-3H-xanthen-9-yl)-5-((2-mercaptoethyl)carbamoyl)benzoate To a solution of TAMRA-5'-COOH (1 eq., 68.3 mg, 0.159 mmol) in DMF (0.228 mL), HATU (1 eq., 60.3 mg, 0.159 mmol), DIPEA (6 eq., 123 mg, 0.157 mL, 0.952 mmol) and cystamine dichloride (5 eq., 178 mg, 0.793 mmol) were subsequently added; the obtained solution mass was stirred overnight. A solution of DTT (5 eq., 122 mg, 0.118 mL, 0.793 mmol) in DCM (0.911 mL) was added to the reaction mass, the stirring continued for 2 hours. Solvents were evaporated; the obtained crude mass was purified by HPLC to yield 46a (33.5 mg, 0.0555 mmol, 35%) as a dark-violet solid.

$^1$H NMR (400 MHz, DMSO-d$_6$) δ9.06 (t, J=5.4 Hz, 1H, 8.70 (d, J=1.8 Hz, 1H), 8.30 (dd, J=1.8, 8.0 Hz, 1H), 7.59 (d, J=8.0 Hz, 1H), 7.08-7.02 (m, 4H), 6.95 (s, 2H), 3.52-3.42 (m, 2H), 3.26 (s, 12H), 2.72 (dt, J=6.8, 8.0 Hz, 2H); $^{13}$C NMR (101 MHz, DMSO-d$_6$) δ166.0, 164.7, 156.8, 156.6, 135.9, 131.2, 130.6, 114.6, 96.3, 42.9, 40.5, 23.3; HR-ESI-MS: C$_{27}$H$_{27}$N$_3$O$_4$S: 489.1722. found 489.1723.

46: 1-({4-[(1Z)-1-{[2-({3-Carboxylato-4-[6-(dimethylamino)-3-(dimethyliminiumyl)-3H-xanthen-9-yl]phenyl}formamido)ethyl]sulfanyl}-2-cyanoeth-1-en-1-yl]phenyl}methyl)-3,3,6,6-tetramethyl-1-thiacyclohept-4-yn-1-ium trifluoroacetate (TAMRA-APN-TMTI)

A solution of 45 (1 eq., 6.74 mg, 0.016 mmol) in ACN (1 mL) was mixed with a solution of 46a (1 eq., 9.64 mg, 0.016 mmol) in DMF (1 mL). DIPEA (5 eq., 132 μL, 0.08 mmol) was then added and obtained reaction mass was injected into HPLC after 5 minutes of reaction to yield 46 (11.9 mg, 0.0149 mmol, 93%) as a dark-violet solid.

$^1$H NMR (400 MHz, DMSO-d$_6$) δ8.98 (t, J=5.40 Hz, 1H), 8.30 (d, J=8.28 Hz, 1H), 8.10-8.20 (m, 1H), 7.85 (s, 1H), 7.57-7.69 (m, 4H), 6.97-7.15 (m, 5H), 6.07 (s, 1H), 4.85 (s, 2H), 2.81-2.90 (m, 4H), 3.28 (br. s., 16H), 1.25 (s, 6H), 1.05 (s, 6H); $^{13}$C NMR (101 MHz, DMSO-d$_6$)—not informative (low resolved signals); HR-ESI-MS: C$_{47}$H$_{49}$N$_4$O$_4$S$_2^+$, 797.31897. found 797.32739.

1-({4-[2-Cyano-1-[(2-{4-[(E)-2-[4-(dimethylamino)phenyl]diazen-1-yl]benzenesulfonamido}ethyl)sulfanyl]eth-1-en-1-yl]phenyl}methyl)-3,3,6,6-tetramethyl-1-thiacyclohept-4-yn-1-ium (47, BHQ2-APN-TMTI)

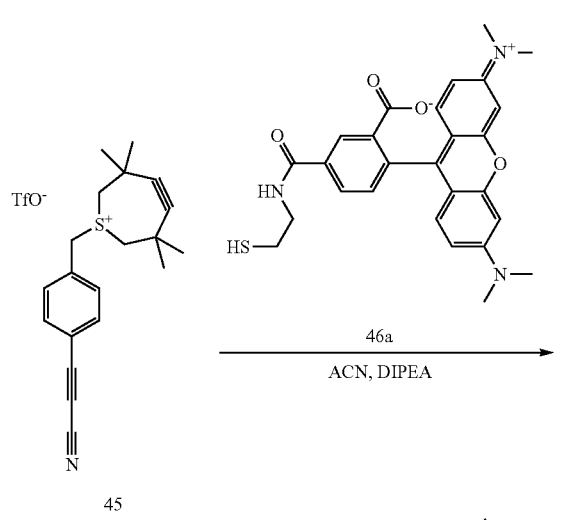

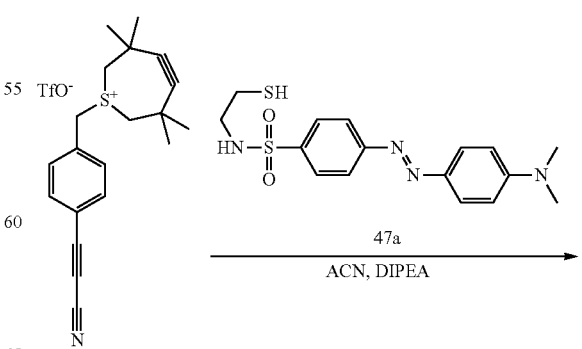

89
-continued

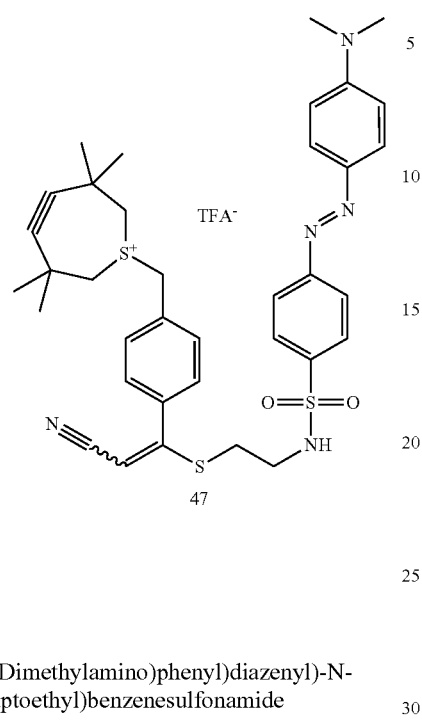

47a: (E)-4-((4-(Dimethylamino)phenyl)diazenyl)-N-(2-mercaptoethyl)benzenesulfonamide To a cooled to 0° C. solution of Dabsyl chloride (1 eq., 100 mg, 0.309 mmol) in dry ACN (3 mL), TEA (7 eq., 218 mg, 0.3 mL, 2.16 mmol) and cystamine dihydrochloride (5 eq., 347 mg, 1.54 mmol) were subsequently added. After 2 hours of stirring, DTT (6 eq., 285 mg, 0.275 mL, 1.85 mmol) was added to the reaction mass. The obtained solution was stirred for another 2 hours, evaporated and the obtained crude product was purified by flash chromatography (cyclohexane-EtOAc) to yield 47a (105.9 mg, 94%) as an orange solid.

47: 1-({4-[(2-Cyano-1-[(2-{4-[(E)-2-[4-(dimethylamino)phenyl]diazen-1-yl]benzenesulfonamido}ethyl)sulfanyl]eth-1-en-1-yl]phenyl}methyl)-3,3,6,6-tetramethyl-1-thiacyclohept-4-yn-1-ium trifluoroacetate The same procedure as for the synthesis of the 46. Yield: 94%.

$^1$H NMR (400 MHz, DMSO-$d_6$) δ8.03 (t, J=4.89 Hz, 1H), 7.91 (d, J=8.53 Hz, 2H), 7.80-7.87 (m, J=9.04 Hz, 2H), 7.72-7.79 (m, J=8.53 Hz, 2H), 7.68 (s, 4H), 6.87 (d, J=9.04 Hz, 2H), 6.08 (s, 1H), 4.86 (s, 2H), 3.92 (d, J=12.05 Hz, 2H), 3.84 (d, J=12.30 Hz, 2H), 3.10 (s, 6H), 2.71-2.87 (m, 4H), 1.32 (s, 6H), 1.17 (s, 6H); $^{13}$C NMR (101 MHz, DMSO-$d_6$) 6160.2, 158.6, 158.3, 155.1, 153.7, 143.1, 140.3, 136.8, 131.9, 131.3, 129.5, 128.2, 125.9, 122.8, 117.2, 112.1, 106.4, 99.4, 60.0, 43.3, 42.9, 34.5, 26.4, 25.3; HR-ESI-MS: $C_{36}H_{42}N_5O_2S_3^+$, 672.24951. found 672.25042.

Compounds 46-47 can be used for the preparation of compounds otherwise not accessible (TMTI).

90

5-(3-{4-[1-(4-{[4-(2-Cyanoeth-1-yn-1-yl)phenyl]carbamoyl}butyl)-1H-1,2,3-triazol-4-yl]butanamido}propyl)-2-[(E)-2-[4-hydroxy-2-(2-{2-[2-(2-{5-[(4S)-2-oxo-hexahydro-1H-thieno[3,4-d]imidazolidin-4-yl]pentanamido}ethoxy)ethoxy]ethoxy}ethoxy)phenyl]diazen-1-yl]benzoic (48, APN-HAZA-biotin)

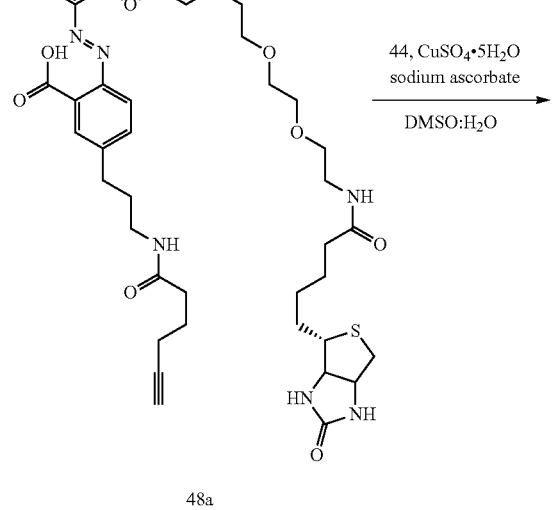

48a

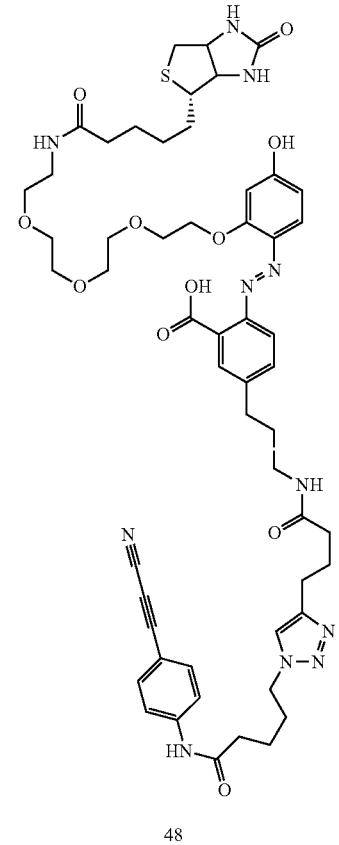

48

Compound 48 can be used for purification and/or immobilization according to the invention.

48a: 2-(6-(Dimethylamino)-3-(dimethyliminio)-3H-xanthen-9-yl)-5-((2-mercaptoethyl)carbamoyl)benzoate This compound was synthesised following the previously reported protocol.

48: 5-(3-{4-[1-(4-{[4-(2-Cyanoeth-1-yn-1-yl)phenyl]carbamoyl}butyl)-1H-1,2,3-triazol-4-yl]butanamido}propyl)-2-[(E)-2-[4-hydroxy-2-(2-{2-[2-(2-{5-[(4S)-2-oxo-hexahydro-1H-thieno[3,4-d]imidazolidin-4-yl]pentanamido}ethoxy)ethoxy]ethoxy}ethoxy)phenyl]diazen-1-yl]benzoic (APN-HAZA-biotin)

To a solution of 48a (1 eq., 10 mg, 0.0123 mmol) and 77 (1 eq., 3.12 mg, 0.0123 mmol) in DMSO (0.472 mL), solution of sodium ascorbate (10 eq., 24.4 mg, 0.123 mmol) and CuSO$_4$·5H$_2$O (5 eq., 15.4 mg, 0.0617 mmol) in water was added. The obtained reaction mass was degassed and stirred overnight at 25° C. The reaction mass was directly purified by HPLC to give 48 (8.3 mg, 0.0078 mmol, 63%) as a yellow solid.

$^1$H NMR (400 MHz, METHANOL-d$_4$) δ7.78 (br. s., 2H), 7.72 (d, J=8.28 Hz, 1H), 7.67 (s, 1H), 7.58 (d, J=8.78 Hz, 2H), 7.50 (d, J=8.78 Hz, 2H), 7.29 (d, J=8.28 Hz, 1H), 7.25 (d, J=8.53 Hz, 1H), 6.29 (d, J=7.78 Hz, 1H), 3.70-3.81 (m, 8H), 3.62 (d, J=4.77 Hz, 2H), 3.58 (d, J=5.02 Hz, 2H), 3.48-3.53 (m, 2H), 3.41-3.48 (m, 2H), 3.01-3.07 (m, 6H), 2.89-3.00 (m, 10H), 2.78 (dd, J=4.89, 12.93 Hz, 1H), 2.52-2.67 (m, 8H), 2.33 (t, J=7.28 Hz, 2H), 2.09-2.19 (m, 2H), 1.81-1.91 (m, 4H), 1.65-1.78 (m, 2H), 1.52-1.63 (m, 2H), 1.42-1.52 (m, 1H), 1.23-1.31 (m, 1H); HR-ESI-MS: C$_{56}$H$_{67}$N$_{11}$O$_{11}$S, 1077.47422. found 1077.45931.

2-((4-(cyanoethynyl)phenyl)amino)-N,N,N-trimethyl-2-oxoethan-1-aminium trifluoroacetate (49)

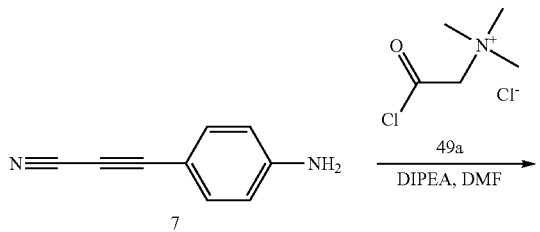

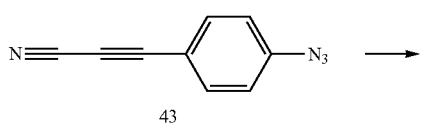

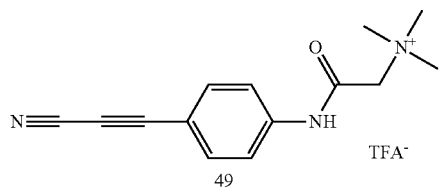

49a: 2-chloro-N,N,N-trimethyl-2-oxoethan-1-aminium

Synthesised as previously described by Vassel and Skelly (10.1002/0471264180.os035.09).

49: 2-((4-(cyanoethynyl)phenyl)amino)-N,N,N-trimethyl-2-oxoethan-1-aminium trifluoroacetate To a solution of 3-(4-aminophenyl)prop-2-ynenitrile (1 eq., 66.3 mg, 0.466 mmol) and DIPEA (1.1 eq., 66.3 mg, 0.0848 mL, 0.513 mmol) in DMF (1 mL), a cooled to −20° C. solution of (2-chloro-2-oxoethyl)trimethylazanium chloride (1.1 eq., 88.3 mg, 0.513 mmol) in DMF (1 mL) was added. The obtained reaction mass was stirred at 25° C. for 10 hours, purified by RP-flash chromatography to give 49 as a yellowish solid (39 mg, 0.110 mmol, 24%).

$^1$H NMR (400 MHz, ACETONITRILE-d$_3$) δ11.14 (br. s., 1H), 7.70-7.83 (m, J=8.78 Hz, 2H), 7.56-7.70 (m, J=8.78 Hz, 2H), 4.33 (s, 2H), 3.28 (s, 9H); $^{13}$C NMR (101 MHz, ACETONITRILE-d$_3$) δ163.5, 142.5, 135.8, 121.2, 113.5, 106.5, 84.4, 66.3, 63.1, 55.2; ESI-MS: C$_{14}$H$_{16}$N$_3$O$^+$[M]$^+$, 242.13. found 242.13.

3-(1-(1-(4-(cyanoethynyl)phenyl)-1H-1,2,3-triazol-4-yl)-2,5,8,11,14-pentaoxaheptadecan-17-amido)pentanedioic acid (50)

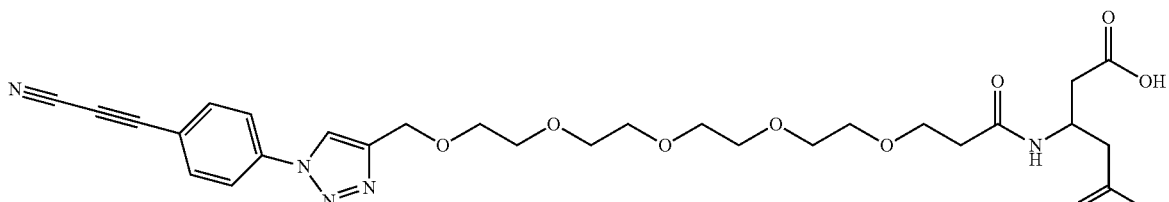

A solution of 43 (1 eq., 5.65 mg, 0.0336 mmol) in DMSO (0.0331 mL), a solution of di-acid-alkyne (1 eq., 14.6 mg, 0.0336 mmol) in water (0.0331 mL) was added. A solution of copper sulfate pentahydrate (0.1 eq., 0.839 mg, 0.00336 mmol) in minimum amount of water was added to the obtained reaction mass followed by the addition of a solution of sodium ascorbate (0.5 eq., 3.33 mg, 0.0168 mmol) in minimum amount of water. The addition repeated after 30 minutes until complete disappearance of the strasting material (2 times overall). Excess of water was evaporated to vacuo (no heating should be used, otherwise hydrolysis product starts to appear), the obtained crude mass was purified by HPLC after the filtration of copper salts through a seringe filter to give 50 (11 mg, 0.01828 mmol, 54%) as a white solid.

$^1$H NMR (400 MHz, ACETONITRILE-d$_3$) δ8.41 (s, 1H), 7.95-8.02 (m, 2H), 7.88-7.94 (m, 2H), 6.86 (d, J=7.78 Hz, 1H), 4.71 (s, 2H), 4.49 (td, J=6.71, 8.41 Hz, 1H), 3.68-3.76 (m, 3H), 3.49-3.68 (m, 21H), 2.53-2.64 (m, 5H), 1.97 (td, J=2.42, 4.96 Hz, 15H); $^{13}$C NMR (101 MHz, ACETONITRILE-d$_3$) δ188.7, 173.3, 161.6, 146.5, 135.1, 131.3, 130.8, 122.5, 121.0, 117.9, 115.4, 64.2, 40.4, 39.5, 36.7, 30.6; ESI-MS: C$_{28}$H$_{34}$N$_5$O$_{10}{}^-$ [M−H]$^-$, 600.21. found 600.23.

N1,N5-bis(23-amino-3,6,9,12,15,18,21-heptaoxatricosyl)-3-(1-(1-(4-(cyanoethynyl)phenyl)-1H-1,2,3-triazol-4-yl)-2,5,8,11,14-pentaoxaheptadecan-17-amido)pentanediamide (51)

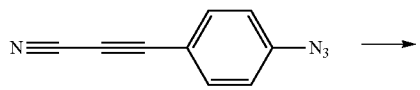

43

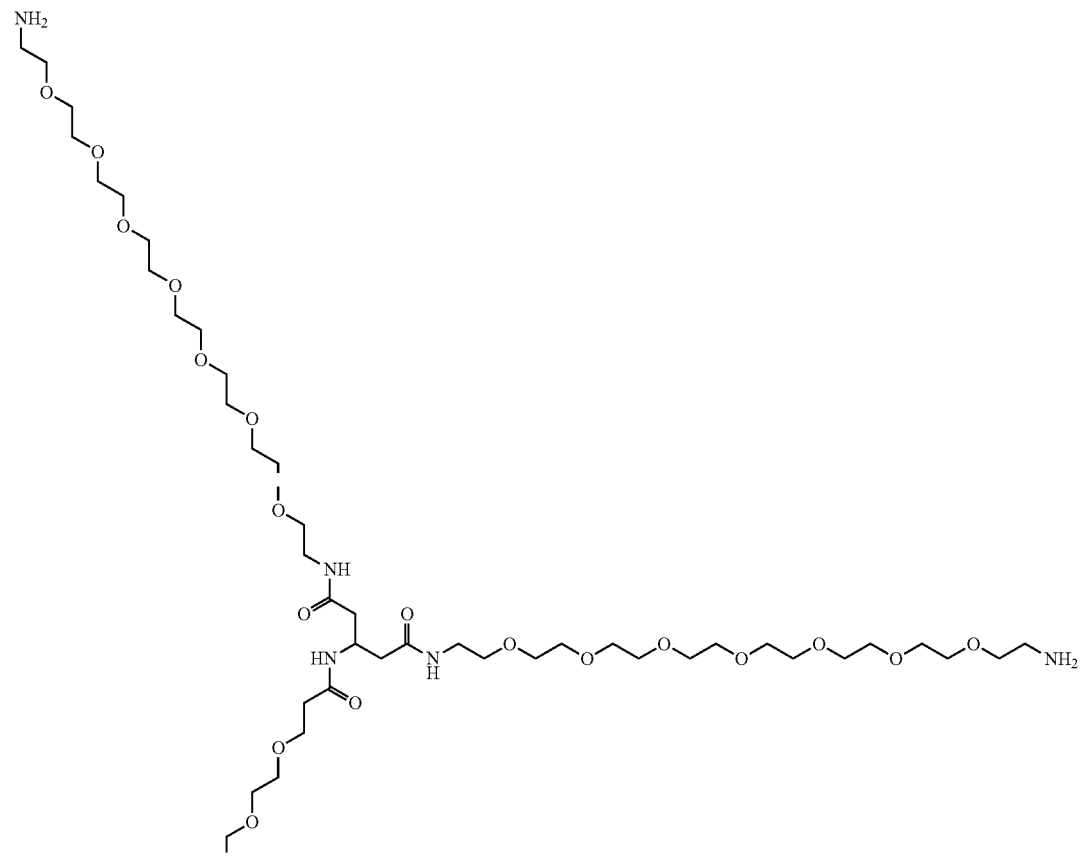

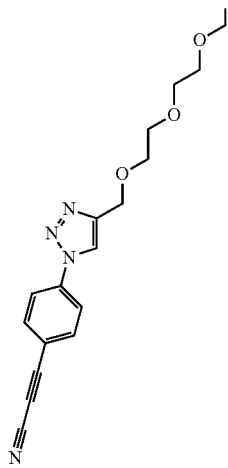

51

A solution of 43 (1 eq., 1.64 mg, 0.00973 mmol) and PEG-Alkyne (1 eq., 11 mg, 0.00973 mmol) in DMSO was added to a mixture of DMSO (0.00958 mL) and water (0.00958 mL). A solution of copper sulfate pentahydrate (0.1 eq., 0.243 mg, 0.000973 mmol) in minimum amount of water was added to the obtained reaction mass followed by the addition of a 5 solution of sodium ascorbate (0.5 eq., 0.964 mg, 0.00487 mmol) in minimum amount of water. The reaction mass was filtered and purified by HPLC to give 51 (5 mg, 0.003839 mmol, 39%) as a colorless liquid.

ESI-HRMS: $C_{60}H_{103}N_9O_{22}$, 1301.72177. found 1301.72204.

N-(17-amino-3,6,9,12,15-pentaoxaheptadecyl)-1-(1-(4-(cyanoethynyl)phenyl)-1H-1,2,3-triazol-4-yl)-2,5,8,11,14-pentaoxaheptadecan-17-amide (52)

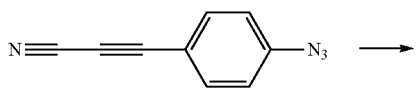

43

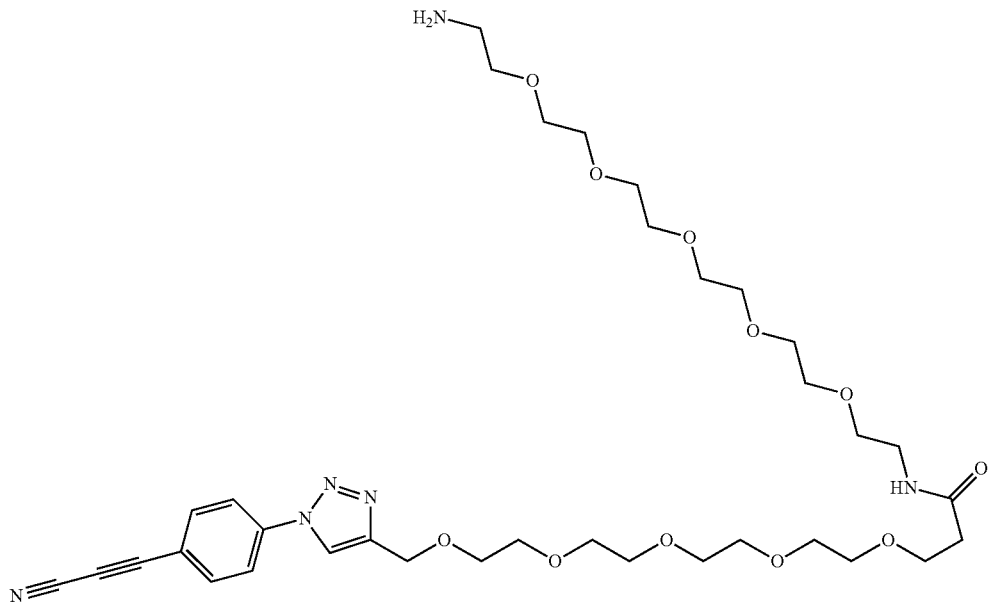

52

A solution of 3-(4-azidophenyl)prop-2-ynenitrile (1 eq., 14.9 mg, 0.0886 mmol) in DMSO (0.0872 mL), a solution of PEG-alkyne (1 eq., 50.2 mg, 0.0886 mmol) in water (0.0872 mL). To the obtained mixture a solution of copper sulfate pentahydrate (0.1 eq., 2.21 mg, 0.00886 mmol) in minimum amount of water was added followed by the addition of a solution of sodium ascorbate (0.5 eq., 8.77 mg, 0.0443 mmol) in minimum amount of water. The addition of copper sulfate pentahydrate (0.1 eq., 2.21 mg, 0.00886 mmol) and sodium ascorbate (0.5 eq., 8.77 mg, 0.0443 mmol) were repeated after 30 minutes if starting azide was still present. Excess of water was evaporated to vacuo, the crude product was purified by HPLC to give 52 (55 mg, 0.07485 mmol, 84%) as a colorless oil.

$^1$H NMR (400 MHz, ACETONITRILE-$d_3$) δ8.42 (s, 1H), 7.95-8.02 (m, J=9.03 Hz, 2H), 7.86-7.95 (m, J=8.78 Hz, 2H), 7.30 (br. s., 2H), 7.19 (br. s., 1H), 4.71 (s, 2H), 3.73-3.79 (m, 2H), 3.65-3.73 (m, 7H), 3.54-3.65 (m, 29H), 3.51 (t, J=5.40 Hz, 2H), 3.34 (q, J=5.35 Hz, 2H), 3.13 (d, J=4.52 Hz, 2H), 2.37-2.46 (m, 2H), 1.92-2.01 (m, 5H); $^{13}$C NMR (126 MHz, CHLOROFORM-d) δ177.5, 151.3, 144.6, 140.7, 140.7, 140.6, 127.2, 126.0, 125.9, 125.8, 122.4, 110.5, 87.2, 75.4, 75.3, 75.3, 75.2, 75.2, 75.1, 75.1, 75.1, 75.0, 74.9, 74.8, 74.8, 72.2, 71.9, 68.9, 68.5, 45.0, 44.2, 41.6; ESI-MS: $C_{35}H_{55}N_6O_{11}^+$[M+H]$^+$, 735.39. found 735.20.

1-(4-(cyanoethynyl)phenyl)-3-(3-(dimethylamino)propyl)urea (53)

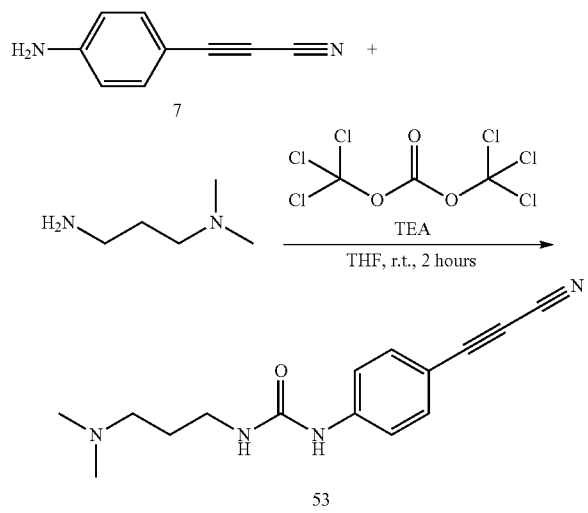

To a solution of triphosgene (1 eq., 56.3 mg, 31.6 μL, 0.19 mmol) in THF (0.404 μL) was added a solution of 3-(4-aminophenyl)prop-2-ynenitrile (3 eq., 80.9 mg, 0.569 mmol) in THF (0.404 μL). Then triethylamine (6 eq., 115 mg, 158 μL, 1.14 mmol). The mixture was stirred for 5 min and then 3-dimethylaminopropylamine (3 eq., 58.1 mg, 71.8 μL, 0.569 mmol) and triethylamine (2 eq., 38.4 mg, 52.7 μL, 0.379 mmol) was added in THF (0.404 L). The reaction mixture was stirred for 10 minutes and then concentrated. The obtained residue was purified by HPLC to give 53 (47 mg, 0.1764 mmol, 93%) as a white solid.

$^1$H NMR (400 MHz, METHANOL-$d_4$) δ7.45-7.50 (m, 2H), 7.41-7.45 (m, 2H), 3.23-3.25 (m, 1H), 3.04-3.11 (m, 2H), 2.80 (s, 6H), 1.77-1.91 (m, 2H); $^{13}$C NMR (101 MHz, METHANOL-$d_4$) δ156.5, 143.7, 134.4, 118.0, 109.3, 105.0, 83.7, 61.0, 55.2, 42.1, 35.9, 25.3; ESI-MS: $C_{15}H_{20}N_4O^+$ [M+H]$^+$, 271.16. found 271.15.

3-((3-(3-(4-(cyanoethynyl)phenyl)ureido)propyl)dimethylammonio)propane-1-sulfonate (54)

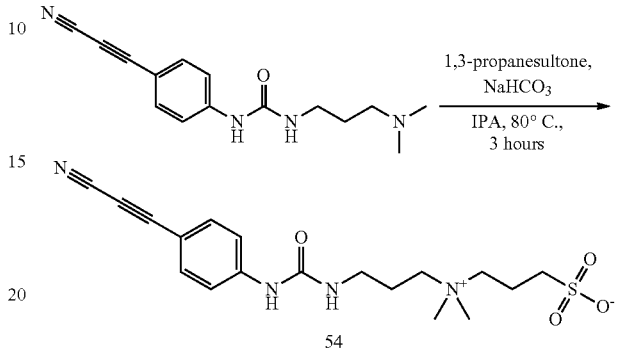

53 (1 eq., 27 mg, 0.0702 mmol) and 1,3-propanesultone (1.1 eq., 9.44 mg, 0.00678 mL, 0.0773 mmol) were dissolved in IPA (0.5 mL) and refluxed for 3 h. The reaction mixture was cooled to room temperature and the precipitate was filtered and washed with cold distilled water to remove any unreacted propanesultone to give 54 (27 mg, 0.0688 mmol, 98%) as a white solid.

$^1$H NMR (400 MHz, DEUTERIUM OXIDE) δ7.45-7.67 (m, 2H), 7.33 (br. s., 2H), 3.61 (br. s., 4H), 3.53 (br. s., 1H), 3.39 (br. s., 2H), 3.31 (br. s., 2H), 3.25 (br. s., 2H), 3.03 (br. s., 7H), 2.89 (br. s., 7H), 2.13 (br. s., 1H), 1.89 (br. s., 7H), 1.08 (br. s., 2H); ESI-HRMS: $C_{18}H_{24}N_4O_4S$, 392.15183. found 392.15254. Compounds 49-54 can be used for a conjugation method according to the invention, for instance for changing ADME parameters (solubilizing agents).

3-(4-(4-(hydroxymethyl)-1H-1,2,3-triazol-1-yl)phenyl)propiolonitrile (55)

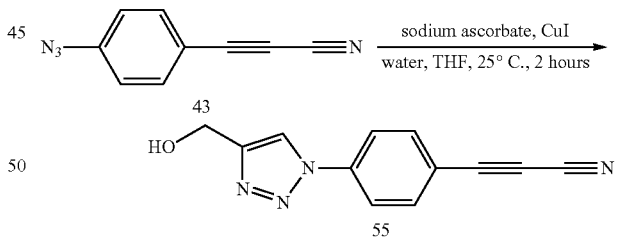

3-(4-azidophenyl)prop-2-ynenitrile (1 eq., 300 mg, 1.78 mmol), 2-propyn-1-ol (2 eq., 200 mg, 0.211 mL, 3.57 mmol) were solubilized in THF (9 mL). To this mixture was added a solution of copper sulfate pentahydrate (10%, 44.5 mg, 0.178 mmol) in 1.5 mL of water followed by the solution of sodium ascorbate (0.5 eq., 176 mg, 0.892 mmol) in 1.5 mL of water. The resulting solution was stirred for 2 h and then concentrated on rotary evaporator. The residue was extracted with DCM. The organic layer was washed with NH$_4$Cl (sat.) and water, dried over MgSO$_4$ and then evaporated. The residue was resolubilised in DCM and the product was filtered to give 55 (23.28 mg, 0.08108 mmol, 92%) as a slightly yellowish solid.

1H NMR (400 MHz, MeOD) δ 8.58 (s, 1H), 8.04 (d, J=7.4 Hz, 2H), 7.93 (d, J=7.4 Hz, 2H), 4.77 (s, 2H); ESI-MS: C$_{12}$H$_9$N$_4$O$^+$[M+H]$^+$, 225.08. found 225.05.

3-(4-(4-(bromomethyl)-1H-1,2,3-triazol-1-yl)phenyl) propiolonitrile (56)

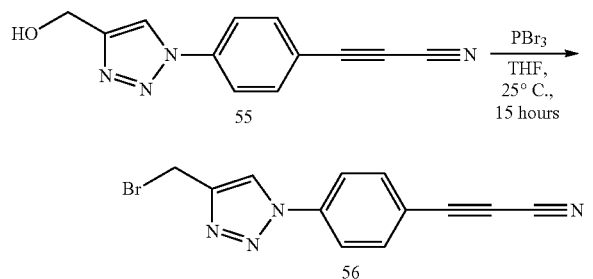

55 (1 eq., 19.8 mg, 0.0881 mmol) was dissolved in THF (1 mL) under nitrogen at room temperature and 3-{4-[4-(bromomethyl)-1H-1,2,3-triazol-1-yl]phenyl}prop-2-ynenitrile (23.3 mg, 0.0811 mmol, 92%) was added. The reaction mixture was stirred at room temperature for 15 hours. Solvents were evaporated, the crude product was purified by HPLC to give 56 (23.3 mg, 0.0811 mmol, 92%) as a white solid.

$^1$H NMR (400 MHz, ACETONITRILE-d$_3$) δ8.44 (s, 1H), 7.78-8.03 (m, 5H), 4.74 (s, 2H); $^{13}$C NMR (101 MHz, CHLOROFORM-d) δ150.9, 144.3, 140.6, 140.5, 126.0, 125.9, 110.4, 87.1, 68.5, 27.0; ESI-MS: C$_{12}$H$_8$BrN$_4^+$[M+H]$^+$, 286.99. found 287.08.

Compound 56 can be used for a bioconjugation method according to the invention.

1-({1-[4-(cyanoethynyl)phenyl]-1H-1,2,3-triazol-4-yl}methyl)-3,3,6,6-tetramethyl-4,5-didehydro-2,3,6,7-tetrahydrothiepinium trifluoroacetate (57)

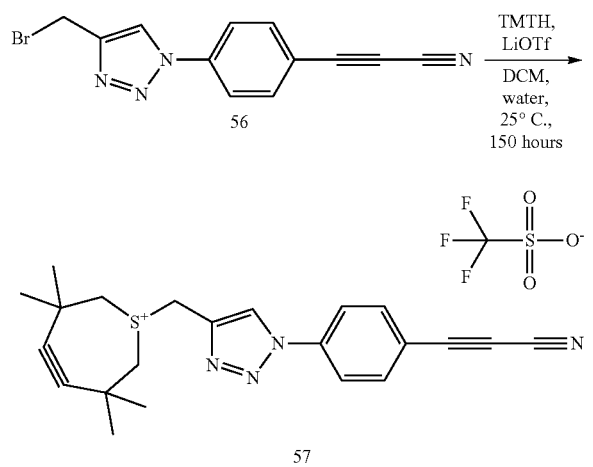

To a degassed solution of 3-{4-[4-(bromomethyl)-1H-1,2,3-triazol-1-yl]phenyl}prop-2-ynenitrile (1 eq., 19.6 mg, 0.0684 mmol) and TMTH (1.89 eq., 21.7 mg, 0.129 mmol) in DCM (0.982 mL), a solution of lithium triflate (10 eq., 106 mg, 0.684 mmol) in water (0.982 mL) was added. The obtained biphasic mixture was vigorously mixed for 2 days at 25° C. Phases were separated, organic phase was washed with DCM (5×2 mL). United organic fractions were evaporated and the crude was purified by HPLC to give 57 (23.7 mg, 0.0451, 66%) as a white solid.

ESI-HRMS: C$_{22}$H$_{23}$N$_4$S, 375.16434. found 375.16497.

Compound 57 can be used for click-chemistry (strain promoted click) according to the invention.

4-(((1-(4-(cyanoethynyl)phenyl)-1H-1,2,3-triazol-4-yl)methyl)carbamoyl)-2-(6-(dimethylamino)-3-(dimethyliminio)-3H-xanthen-9-yl)benzoate (58)

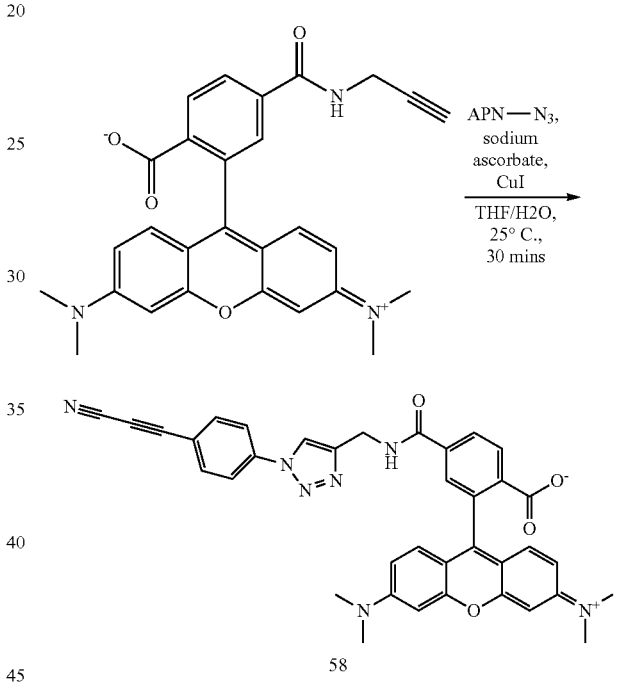

2-[6-(dimethylamino)-3-(dimethyliminiumyl)-3H-xanthen-9-yl]-4-[(prop-2-yn-1-yl)carbamoyl]benzoate (1 eq., 52.8 mg, 0.113 mmol) and 3-(4-azidophenyl)prop-2-ynenitrile (1 eq., 19 mg, 0.113 mmol) were solubilized in THF (1 mL). H2O (1 mL) was added to the obtained reaction mixture followed by the addition of solutions of Copper Sulphate pentahydrate (10%, 2.82 mg, 0.0113 mmol) and sodium ascorbate (50%, 11.2 mg, 0.0565 mmol) in minimum amount of water (separately). The obtained reaction mixture was stirred for another 30 minutes, evaporated and purified by HPLC to give 58 (66.8 mg, 0.105 mmol, 93%) as a dark-violet solid.

$^1$H NMR (400 MHz, METHANOL-d$_4$) δ8.51 (s, 1H), 8.33 (d, J=8.28 Hz, 1H), 8.16 (dd, J=1.51, 8.28 Hz, 1H), 7.86-8.02 (m, 2H), 7.64-7.86 (m, 3H), 7.02-7.12 (m, 2H), 6.84-7.02 (m, 4H), 4.58-4.71 (m, 2H); ESI-HRMS: C$_{37}$H$_{29}$N$_7$O$_4$, 635.22811. found 635.22861.

3-(9-(diethylamino)-5-oxo-5H-benzo[a]phenoxazin-2-yl)propiolonitrile (59)

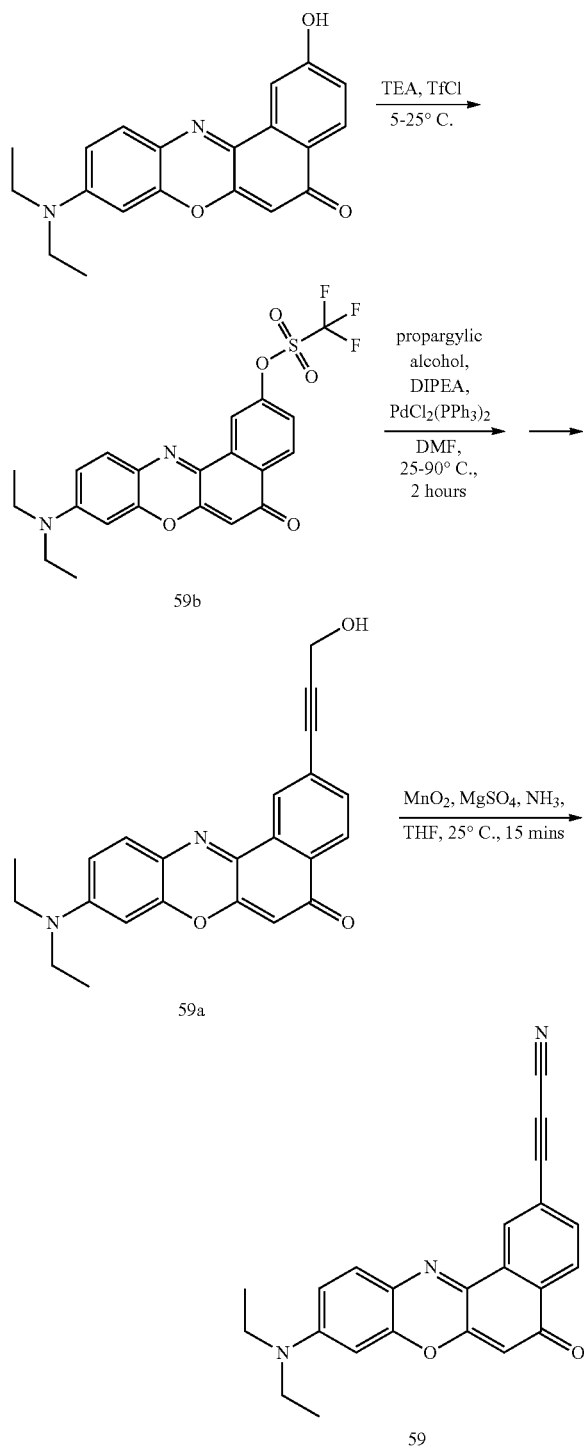 [SMILES: CCN(CC)c1ccc2nc3c4cc(O)ccc4c(=O)cc-3oc2c1 ; CCN(CC)c1ccc2nc3c4cc(OS(=O)(=O)C(F)(F)F)ccc4c(=O)cc-3oc2c1 ; CCN(CC)c1ccc2nc3c4cc(C#CCO)ccc4c(=O)cc-3oc2c1 ; CCN(CC)c1ccc2nc3c4cc(C#CC#N)ccc4c(=O)cc-3oc2c1]

59b: 8-(diethylamino)-3-hydroxy-12H-10-oxa-5-azatetraphen-12-one (1 eq., 65 mg, 0.194 mmol) was dissolved in dry DCM (2 mL) and cooled to 5° C. Then TEA (1.2 eq., 23.6 mg, 0.0324 mL, 0.233 mmol) was added followed by the addition of TfCl (1.2 eq., 39.3 mg, 0.0249 mL, 0.233 mmol). The addition of Tf2O was repeated untile complete disappearance of the starting material. The solvent was evaporated and the residue was treated with water. The precipitate was filtered off and washed with water and heptane to give the desired product (76 mg, 0.163 mmol, 84%) as a dark-violet solid.

ESI-HRMS: $C_{21}H_{17}F_3N_2O_5S$, 466.08103. found 466.08221.

59a: Under an inert atmosphere, DIPEA (2 eq., 16.1 mg, 0.0206 mL, 0.124 mmol) and Propargylic alcohol (1.5 eq., 5.23 mg, 0.00551 mL, 0.0933 mmol) were added to a solution of 59b (1 eq., 29 mg, 0.0622 mmol), $PdCl_2(PPh_3)_2$ (5%, 2.18 mg, 0.00311 mmol) and CuI (10%, 1.18 mg, 0.00622 mmol) in DMF (1 mL). After stirring for 2 hours at 90° C., the solvent was removed under reduced pressure. The crude product was purified by flash chromatography (DCM-MeOH from 100-0 to 80-20).

ESI-HRMS: $C_{23}H_{20}N_2O_3$, 372.14739. found 372.14735.

59: To the solution of 59a (1 eq., 10 mg, 0.0269 mmol) in THF (0.121 mL) was added $MgSO_4$ (15 eq., 48.5 mg, 0.403 mmol), $NH_3$ (4 eq., 2 M, 0.0537 mL, 0.107 mmol), and $MnO_2$ (15 eq., 35 mg, 0.403 mmol). The reaction mixture was stirred at r.t. for 15 mins and followed by HPLC. After completion the mixture was filtered through Celite and washed thoroughly with THF. Evaporation of the filtrate gave crude 59 (9.47 mg, 0.0258 mmol, 96%) which was purified by HPLC.

$^1$H NMR (400 MHz, CHLOROFORM-d) δ8.91 (s, 1H), 8.26 (d, J=8.03 Hz, 1H), 7.79 (dd, J=1.51, 8.03 Hz, 1H), 7.62 (d, J=9.29 Hz, 1H), 6.74 (dd, J=2.63, 9.16 Hz, 1H), 6.51 (d, J=2.51 Hz, 1H), 6.35 (s, 1H), 5.31 (s, 2H), 3.49 (q, J=7.11 Hz, 4H), 1.09-1.36 (m, 6H); ESI-HRMS: $C_{23}H_{17}N_3O_2$, 367.13208. found 367.13145.

(E)-3-(4-((4-(dimethylamino)phenyl)diazenyl)phenyl)propiolonitrile (60)

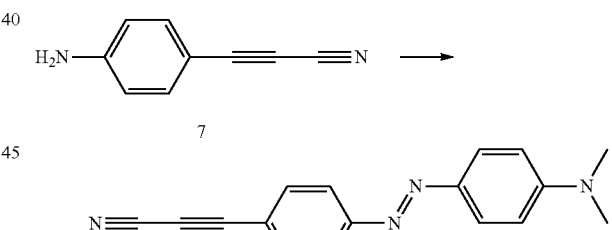

7 (1 eq., 167 mg, 1.17 mmol) was dissolved in acetonitrile (2.58 mL). To this stirred mixture was added Isoamyl nitrite (1.5 eq., 206 mg, 0.237 mL, 1.76 mmol), stirring continued for another 2 minutes, then dimethylaniline (1.1 eq., 156 mg, 0.165 mL, 1.29 mmol) was added. The resulting reaction mixture was stirred overnight (turned red), evaporated and purified by flash chromatography (DCM, first peak) to give 60 (120 mg, 0.437 mmol, 37%) as red solid.

$^1$H NMR (400 MHz, CHLOROFORM-d) δ7.91 (d, J=9.03 Hz, 2H), 7.82-7.88 (m, J=8.53 Hz, 2H), 7.62-7.77 (m, J=8.53 Hz, 2H), 6.77 (d, J=9.03 Hz, 2H), 3.08-3.18 (m, 6H); $^{13}$C NMR (101 MHz, CHLOROFORM-d) δ154.7, 153.2, 143.7, 134.4, 125.8, 122.5, 117.3, 111.6, 105.6, 83.3, 64.2, 40.3; ESI-HRMS: $C_{17}H_{14}N_4$, 274.12185. found 274.12247.

Compounds 58-60 can be used for a detection method according to the invention.

tert-butyl ((1-(4-(cyanoethynyl)phenyl)-1H-1,2,3-triazol-4-yl)methyl)carbamate (61)

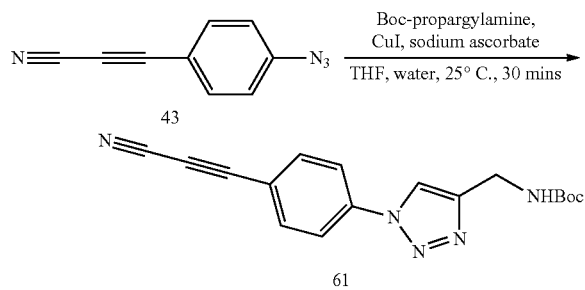

To a solution of 43 (1 eq., 51.5 mg, 0.306 mmol) and boc-propargylamine (1 eq., 47.5 mg, 0.306 mmol) in THF (2 mL) were added H$_2$O (1 mL) and solution of CuSO$_4$ (10%, 4.89 mg, 0.0306 mmol) and sodium ascorbate (50%, 30.3 mg, 0.153 mmol) in water (50 uL each). Stirring continued for 10 minutes, one more portion of CuSO$_4$ (10%, 4.89 mg, 0.0306 mmol) and sodium ascorbate (50%, 30.3 mg, 0.153 mmol) was added. After another 15 minutes of stirring, Et$_2$O (15 mL) and NH$_4$Cl (sat, 10 mL) were added. Organic phase was washed two more times with NH$_4$Cl (sat, 10 mL), dried over MgSO$_4$ and evaporated to give 61 (98 mg, 0.303 mmol, 99%) as a yellow solid. Used without further purification.

$^1$H NMR (400 MHz, CHLOROFORM-d) δ7.97 (s, 1H), 7.74-7.81 (m, J=8.78 Hz, 2H), 7.67-7.74 (m, J=8.78 Hz, 2H), 4.41 (d, J=6.02 Hz, 2H), 1.32-1.41 (m, 9H); $^{13}$C NMR (101 MHz, CHLOROFORM-d) δ139.0, 135.1, 120.4, 117.8, 107.2, 105.1, 81.3, 64.5, 28.4; ESI-MS: C$_{17}$H$_{18}$N$_5$O$_2^+$[M+H]$^+$, 323.14. found 323.13.

(1-(4-(cyanoethynyl)phenyl)-1H-1,2,3-triazol-4-yl)methanaminium trifluoroacetate (62)

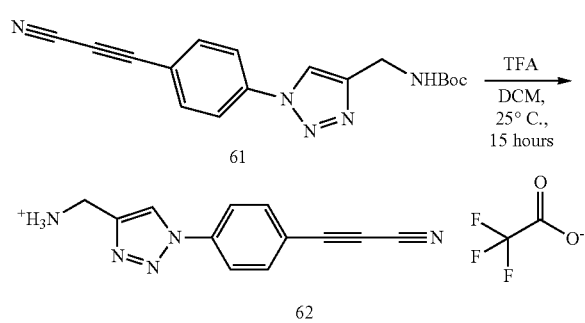

To a solution of 61 (1 eq., 21.5 mg, 0.0665 mmol) in DCM (1 mL) was added TFA (20 eq., 151 mg, 0.0988 mL, 1.33 mmol). The obtained reaction mixture was left overnight at room temperature (or 2 hours at 37° C.) to the targeted product (22.4 mg, 0.0665 mmol, 100%) after the evaporation of all volatile compounds.

$^1$H NMR (400 MHz, METHANOL-d$_4$) δ8.74 (s, 1H), 7.99-8.15 (m, 2H), 7.85-7.97 (m, 2H), 4.25-4.45 (m, 2H); $^{13}$C NMR (101 MHz, METHANOL-d$_4$) δ141.2, 138.9, 135.2, 122.3, 120.3, 117.7, 104.4, 81.1, 62.9, 34.0; ESI-MS: C$_{12}$H$_{10}$N$_5^+$[M]$^+$, 227.09. found 227.10.

N-((1-(4-(cyanoethynyl)phenyl)-1H-1,2,3-triazol-4-yl)methyl)-4-(3-(trifluoromethyl)-3H-diazirin-3-yl)benzamide (63)

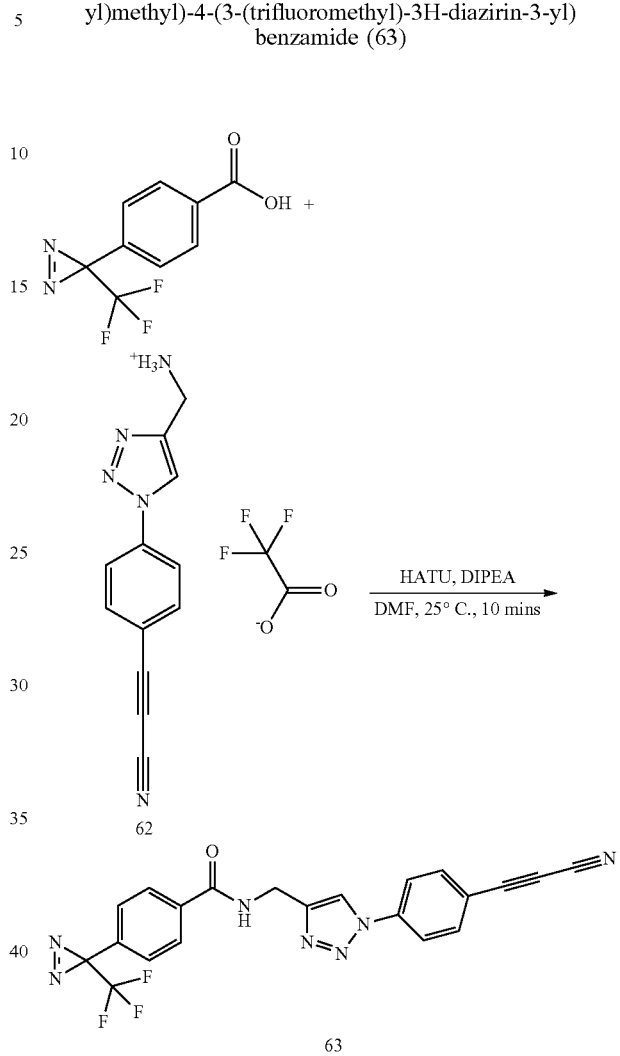

A solution of 4-[3-(trifluoromethyl)-3H-diazirin-3-yl]benzoic acid (1 eq., 57.8 mg, 0.251 mmol), HATU (1 eq., 95.5 mg, 0.251 mmol), and DIPEA (3 eq., 97.4 mg, 0.125 mL, 0.753 mmol) in DMF (2 mL) was added onto 62 (1 eq., 84.7 mg, 0.251 mmol). The obtained reaction mass was stirred for 10 minutes and purified by HPLC to give the targeted compound (76.5 mg, 0.176 mmol, 70%) as a white solid.

ESI-HRMS: C$_{21}$H$_{12}$F$_3$N$_7$O, 435.10554. found 435.10512.

Compound 63 can be used for a labeling method according to the invention, such as for photolabeling of proteins.

tert-Butyl (2-((2-(4-(cyanoethynyl)benzamido)ethyl)disulfanyl)ethyl)carbamate (64)

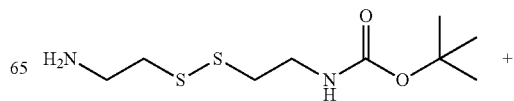

2-((2-(4-(cyanoethynyl)benzamido)ethyl)disulfanyl)ethan-1-aminium trifluoroacetate (65)

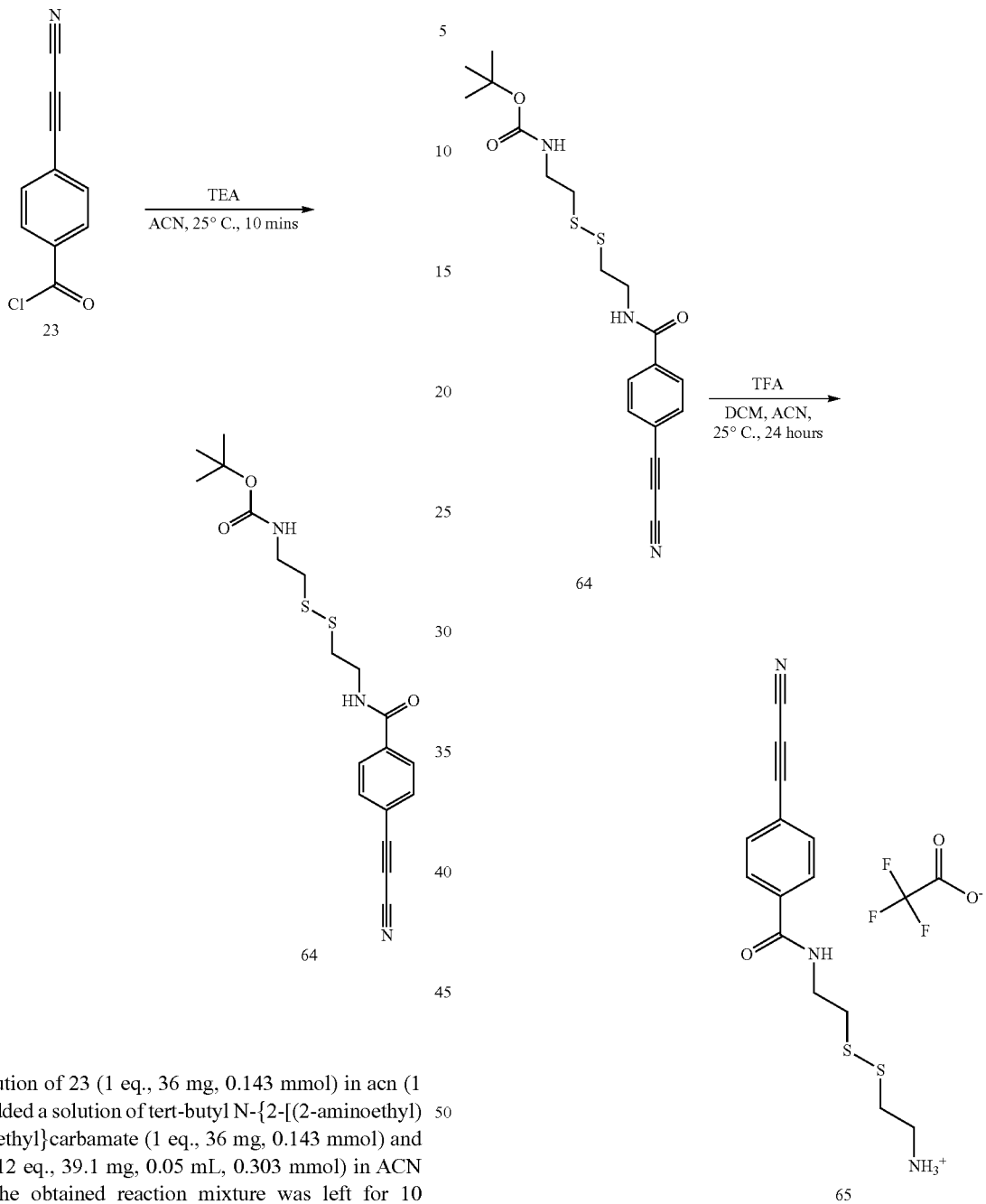

To a solution of 23 (1 eq., 36 mg, 0.143 mmol) in acn (1 mL) was added a solution of tert-butyl N-{2-[(2-aminoethyl)disulfanyl]ethyl}carbamate (1 eq., 36 mg, 0.143 mmol) and DIPEA (2.12 eq., 39.1 mg, 0.05 mL, 0.303 mmol) in ACN (1 mL). The obtained reaction mixture was left for 10 minutes, then solvents were evaporated and the crude product was purified by flash chromatography to give the targeted product (29.3 mg, 0.0723 mmol, 51%) as a yellowish solid.

$^1$H NMR (400 MHz, METHANOL-$d_4$) δ7.74-7.84 (m, J=8.53 Hz, 2H), 7.58-7.74 (m, J=8.53 Hz, 2H), 3.60 (t, J=6.78 Hz, 2H), 3.23-3.35 (m, 2H), 2.85 (t, J=6.78 Hz, 2H), 2.71 (t, J=6.90 Hz, 2H), 1.32 (s, 9H); $^{13}$C NMR (101 MHz, METHANOL-$d_4$) δ167.3, 157.0, 137.3, 133.5, 127.5, 120.1, 104.4, 81.5, 78.8, 63.1, 39.3, 39.1, 37.8, 27.4, 26.6; ESI-MS: $C_{19}H_{24}N_3O_3S_2^+$[M+H]$^+$, 406.12. found 406.10.

To a solution of 64 (1 eq., 29.3 mg, 0.0723 mmol) in ACN-DCM mixture (1 mL of each solvent) was added TFA (10 eq., 82.4 mg, 0.0537 mL, 0.723 mmol). The obtained reaction mixture was stirred for 24 hours, and evaporated to give the targeted compound 65 (30 mg, 0.0715 mmol, 99%) as a colorless liquid.

ESI-HRMS: $C_{14}H_{16}N_3OS_2^+$, 306.07293. found 306.07312.

2-((2-(4-(cyanoethynyl)benzamido)ethyl)disulfanyl)ethan-1-aminium trifluoroacetate (66)

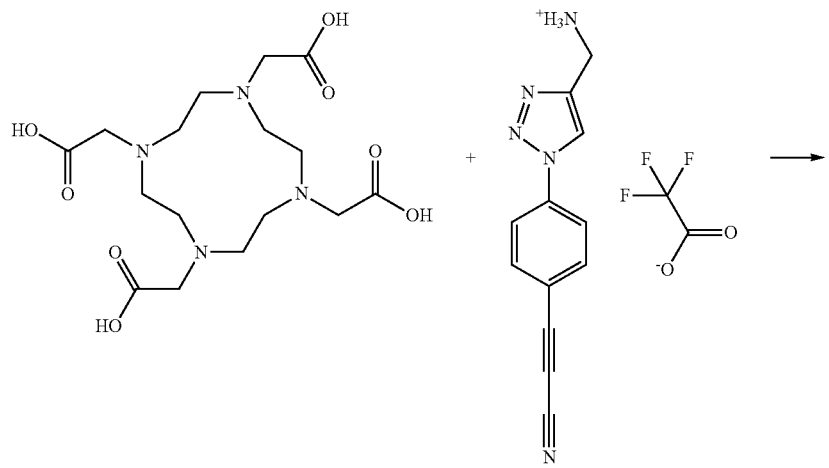

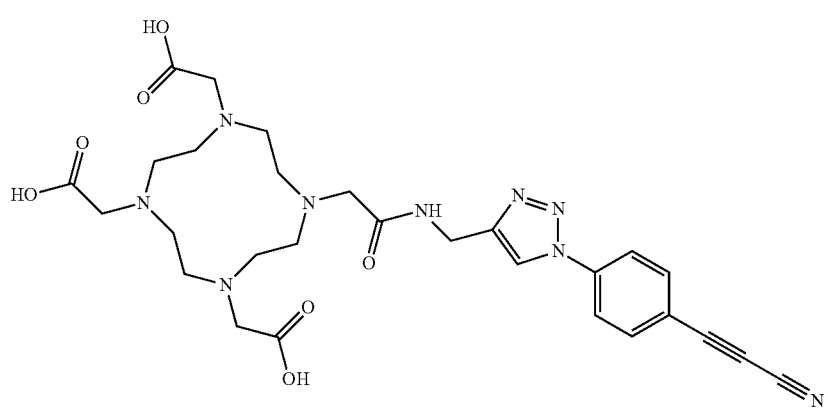

62 (0.567 eq., 10.1 mg, 0.0299 mmol) solution in MeOH (0.0881 mL) was slowly added to a solution of 2-[4,7,10-tris(carboxymethyl)-1,4,7,10-tetraazacyclododecan-1-yl] acetic acid (1 eq., 21.4 mg, 0.0528 mmol) in water (0.661 mL). The mixture was cooled by ice and pH was adjusted to 5 using DIPEA (25.2 eq., 172 mg, 0.22 mL, 1.33 mmol). An aqueous solution of EDC (0.65 eq., 6.59 mg, 0.0344 mmol) was added dropwise and stirred for 20 min with ice cooling. pH was raised to 8 using DIPEA and reacted for 30 min at room temperature. The end point of the reaction was monitored using HPLC.

ESI-HRMS: $C_{28}H_{35}N_9O_7^+$, 609.26594. found 609.26417. Compound 66 can be used as a chelating agent.

5-((4-((4-(2-Cyano-1-((2-(4-((4-((E)-(2,5-dimethoxy-4-((E)-(4-nitrophenyl)diazenyl)phenyl)diazenylphenyl)-(methyl)amino)butanamido)ethyl)thio)vinyl)phenyl)amino)-4-oxobutyl)carbamoyl)-2-(6-(dimethylamino)-3-(dimethyliminio)-3H-xanthen-9-yl)benzoate (A)

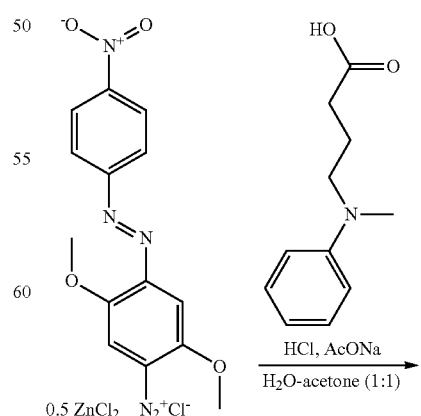

Fast Black K

-continued

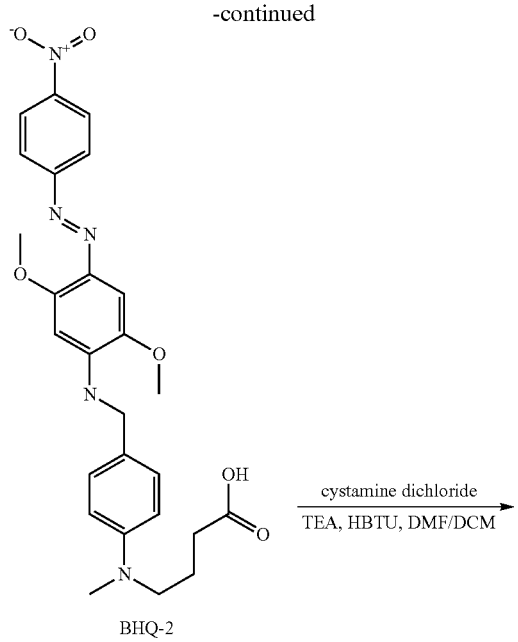

BHQ-2

-continued

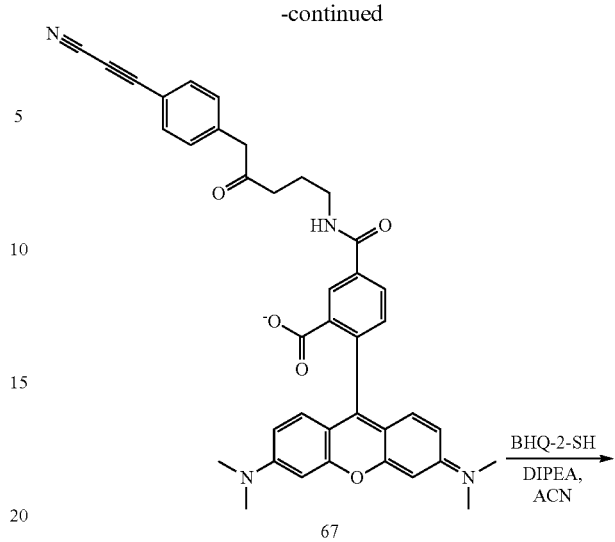

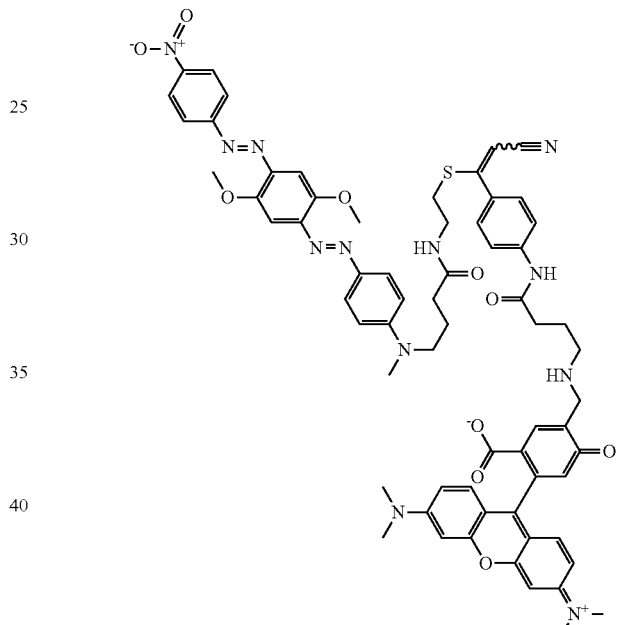

4-((4-((E)-(2,5-Dimethoxy-4-((E)-(4-nitrophenyl)diazenyl)phenyl)diazenyl)phenyl)(methyl)amino)-butanoic acid (BHQ-2)

Fast Black K hemi (zinc chloride) salt (practical grade, ≈30% dye content) (7.76 g) was suspended in cold water (150.0 mL, 0° C.) and stirred for 20 minutes. The suspension was filtered, and the red solution was added dropwise to a cold (0° C.) mixture of 4-(methyl(phenyl)amino)butanoic acid (1.33 g, 6.88 mmol), concentrated hydrochloric acid (3.1 mL) and sodium acetate (3.6 g, 43.90 mmol) in water-acetone mixture (1:1) (150.0 mL). The reaction mixture was stirred at 10° C. for 15 minutes and at room temperature for 2 hours. Then the reaction crude was extracted with ethyl acetate (3×150 mL) and the combined organic layers were dried over Na$_2$SO$_4$. The crude product was purified by column chromatography on silica gel (100% EtOAc, then 100% DCM to DCM/MeOH (95:5)). BHQ-2 (1.36 g, 39%) was obtained as a dark violet solid.

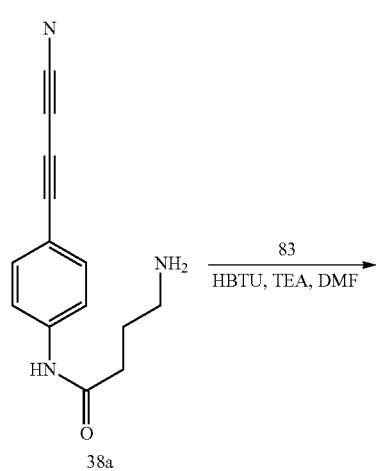

1H NMR (400 MHz, METHANOL-d₄) δ 8.31 (d, J=9.0 Hz, 2H), 8.00 (d, J=9.0 Hz, 2H), 7.86 (d, J=9.0 Hz, 2H), 7.45 (s, 1H), 7.40 (s, 1H), 6.77 (d, J=9.0 Hz, 2H), 4.05 (s, 3H), 4.00 (s, 3H), 3.5 (t, J=7.1 Hz, 2H), 2.36 (t, J=7.1 Hz, 2H), 1.98-1.90 (m, 2H); 13C NMR (101 MHz, METHANOL-d₄) δ 176.2, 157.1, 154.3, 153.0, 151.4, 149.0, 147.4, 145.0, 142.6, 126.9, 125.3, 124.2, 112.1, 101.7, 100.7, 57.2, 52.3, 39.0, 31.6, 22.9.

65b: 4-((4-((E)-(2,5-Dimethoxy-4-((E)-(4-nitrophenyl)diazenyl)phenyl)diazenyl)phenyl)(methyl)amino)-N-(2-mercaptoethyl)butanamide ((BHQ-2)-SH)

BHQ-2 (1 eq., 92.2 mg, 0.182 mmol) was dissolved in a mixture of DMF (5 mL) and DCM (10 mL). TEA (6 eq., 152 µL, 1.09 mmol) and cystamine dichloride (5 eq., 204 mg, 0.91 mmol) were added. The mixture was cooled to 0° C. and HBTU (1 eq., 69 mg, 0.182 mmol) was added. The solution was allowed to reach room temperature and stirred for 15 hours. When total conversion was reached, DTT (6 eq., 168 mg, 0.162 mL, 1.09 mmol) was added. After the resulting mixture has been stirred for 10 minutes at room temperature, the crude was diluted with saturated NaHCO₃ solution (75 mL) and extracted with EtOAc (2×50 mL). The organic layers were combined, washed with water (50 mL), brine (50 mL) and dried over Na₂SO₄. The crude product was purified by column chromatography on silica gel (DCM/MeOH from 100:0 to 95:5) to yield (BHQ-2)-SH (60.7 mg, 0.107 mmol, 59%) as a dark violet solid.

¹H NMR (400 MHz, CHLOROFORM-d) δ 8.33 (d, J=9.0 Hz, 2H), 8.0 (d, J=9.1 Hz, 2H), 7.9 (d, J=9.1 Hz, 2H), 7.42 (s, 1H), 7.42 (s, 1H), 6.75 (d, J=9.00 Hz, 2H), 5.90 (t, J=5.6 Hz, 1H), 4.06 (s, 3H), 4.01 (s, 3H), 3.49 (t, J=7.4 Hz, 2H), 3.41 (dt, J=6.2, 6.4 Hz, 2H), 2.64 (td, J=6.4, 8.47 Hz, 2H), 2.24 (t, J=7.4 Hz, 2H), 2.01-1.94 (m, 2H); 13C NMR (101 MHz, CHLOROFORM-d) δ 172.2, 156.6, 153.8, 152.4, 151.1, 148.5, 147.0, 144.7, 142.3, 126.4, 124.9, 123.7, 111.6, 101.2, 100.3, 57.0, 56.9, 51.8, 42.5, 38.7, 33.4, 24.9, 23.0; HR-ESI-MS: $C_{27}H_{31}N_7O_5S$, 565.2107. found 565.2105.

67: 5-((4-((4-(Cyanoethynyl)phenyl)amino)-4-oxobutyl)carbamoyl)-2-(6-(dimethylamino)-3-(dimethyliminio)-3H-xanthen-9-yl)benzoate To a cooled to 0° C. degased solution of 62a (1 eq., 17.3 mg, 0.0507 mmol) and TAMRA-5'-COOH (1 eq., 21.8 mg, 0.0507 mmol) in DMF (1.4 mL), HBTU (1 eq., 19.2 mg) was added at 0° C. Obtained reaction mass was stirred for 5 minutes and TEA was added. The reaction mass was stirred for 1 hour at 25° C., evaporated and purified by HPLC to yield 65a (22 mg, 68%) as a dark-violet solid.

¹H NMR (400 MHz, METHANOL-d₄) δ 8.8 (br. s, 1H), 8.7 (s, 1H), 8.08-8.16 (d, J=8.2 Hz, 1H), 7.60-7.70 (d, J=8.9 Hz, 2H), 7.49-7.58 (d, J=8.9 Hz, 2H), 7.32-7.39 (d, J=8.2, 1H), δ 7.01 (s, 4H), 6.93 (s, 2H), 3.48-3.58 (m, 2H), 3.26 (s, 12H), 2.44-2.54 (t, J=7.17 Hz, 2H), 1.98-2.12 (m, 2H); ¹³C NMR (101 MHz, METHANOL-d₄)—not informative; HR-ESI-MS: 639.24817. found 639.24310.

A: 5-((4-((4-(2-Cyano-1-((2-(4-((4-((E)-(2,5-dimethoxy-4-((E)-(4-nitrophenyl)diazenyl)phenyl)diazenylphenyl -(methyl)amino)butanamido)ethyl)thio)vinyl)phenyl)amino)-4-oxobutyl)carbamoyl)-2-(6-(dimethylamino)-3-(dimethyliminio)-3H-xanthen-9-yl)benzoate To a degased solution of BHQ-SH (1.13 eq., 2 mg, 0.00354 mmol) in DCM (0.5 mL), a degased solution of 67 (1 eq., 2 mg, 0.00313 mmol) in methanol (0.5 mL) was added. TEA (4.6 eq., 2 µL, 0.0144 mmol) was added and the obtained reaction mass was left overnight at 25° C. Solvents were evaporated; the crude product was solubilised in DMSO (0.5 mL) and purified by HPLC to give BHQ-APN-TAMRA (A, 2.7 mg, 0.00225 mmol, 72%) as dark-violet solid.

¹H NMR (400 MHz, METHANOL-d4) δ 8.63 (d, J=2.0 Hz, 1H), 8.34 (d, J=8.8 Hz, 2H), 8.22 (dd, J=7.8, 2.0 Hz, 1H), 8.00 (d, J=8.8 Hz, 2H), 7.75 (d, J=9.0 Hz, 2H), 7.69 (d, J=8.5 Hz, 2H), 7.53 (d, J=8.0 Hz, 1H), 7.39 (d, J=8.5 Hz, 2H), 7.34 (d, J=9.0 Hz, 2H), 6.75-6.86 (m, 8H), 5.48 (s, 1H), 4.02 (s, 3H), 3.92 (s, 3H), 3.58-3.63 (m, 2H), 3.45-3.52 (m, 2H), 3.21 (s, 12H), 3.16 (t, J 6.9 Hz, 2H), 3.08 (s, 3H), 2.71 (t, J=6.5 Hz, 2H), 2.55 (t, J=6.2 Hz, 2H), 2.22 (t, J=6.9 Hz, 2H), 2.08-2.16 (m, 2H), 1.88-1.96 (m, 2H), 1.61 (br.s, 1H); ¹³C NMR (101 MHz, METHANOL-d₄)—not informative; HR-ESI-MS: $C_{65}H_{65}N_{12}O_{11}S^+$ [M+H]⁺, 1205.46618. found 1205.46748.

5-((3-(3-((2-(4-((4-((E)-(2,5-Dimethoxy-4-((E)-(4-nitrophenyl)diazenyl)phenyl)diazenyl)phenyl)(methyl)amino)butanamido)ethyl)thio)-2,5-dioxopyrrolidin-1-yl)propyl)carbamoyl)-2-(6-(dimethylamino)-3-(dimethyliminio)-3H-xanthen-9-yl)benzoate (B)

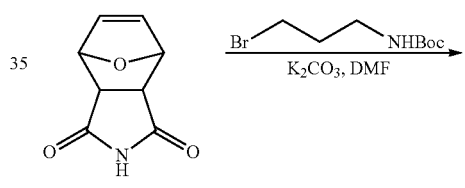

B-4

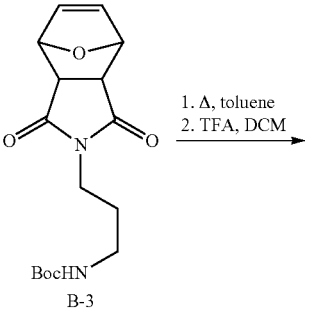

B-3

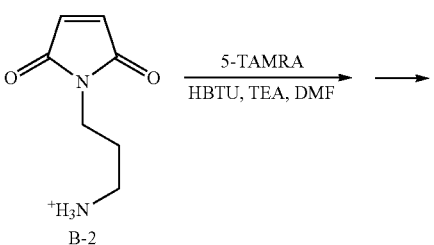

B-2

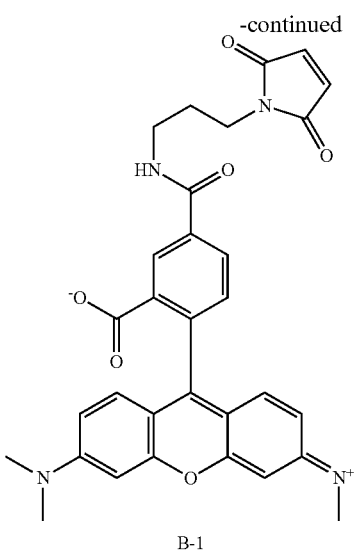

B-1

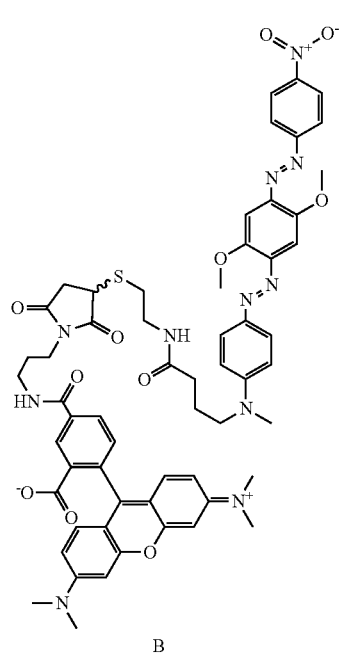

B

B-4: 3a,4,7,7a-Tetrahydro-1H-4,7-epoxyisoindole-1,3(2H)-dione

This compound was synthesised according to the previously described procedure.[845]

B-3: tert-Butyl (3-((3aR,7aS)-1,3-dioxo-3a,4,7,7a-tetrahydro-1H-4,7-epoxyisoindol-2(3H)-yl)propyl)carbamate To the solution of B-4 (1 eq., 1.76 g, 10.7 mmol) and tert-butyl N-(3-bromopropyl)carbamate (2 eq., 5.07 g, 21.3 mmol) in DMF (20 mL), $K_2CO_3$ (1.2 eq., 1.77 g, 12.8 mmol) was added. The obtained reaction mass was heated at 50° C. for 18 hours. The solution was left to cool down; a solid residue was filtered and washed with DMF. United organic fractions were evaporated, hexane (50 mL) was added to the obtained slurry mass. Obtained suspensions were stirred for another hour, filtered and washed with hexane to give B-3 (3.36 g, 10.4 mmol, 98%) as white solid.

$^1$H NMR (400 MHz, CHLOROFORM-d) δ 6.49 (s, 2H), 5.23 (s, 2H), 3.52 (t, J=6.5 Hz, 2H), 2.96-3.09 (m, 2H), 2.82 (s, 2H), 1.66-1.75 (m, 2H), 1.41 (s, 9H); $^{13}$C NMR (101 MHz, CHLOROFORM-d) δ 176.5, 155.9, 136.5, 81.0, 79.3, 47.5, 37.1, 36.0, 28.4, 27.8.

B-2: 1-(3-Aminopropyl)-1H-pyrrole-2,5-dione (TFA salt)

A solution of 66c (1 eq., 243 mg, 0.754 mmol) in toluene (25 mL) was refluxed for 3 hours. Toluene was evaporated; the obtained white crude product was resolubilised in DCM (5 mL), TFA (0.5 mL) was added. Stirring was continued for 2 hours until complete disappearance of a starting material (controlled by TLC). Solvent were evaporated after the reaction was quenched by methanol (3 mL). Obtained 1-(3-aminopropyl)-1H-pyrrole-2,5-dione (B-2, TFA salt, 190 mg, 94%) was used without further purification.

$^1$H NMR (400 MHz, METHANOL-$d_4$) δ 6.76 (s, 2H), 3.52 (t, J=6.7 Hz, 2H), 2.80-2.88 (m, 2H), 1.76-1.88 (m, 2H); $^{13}$C NMR (101 MHz, METHANOL-d4) δ 170.6, 135.6, 38.5, 35.4, 28.0.

B-1: 2-(6-(Dimethylamino)-3-(dimethyliminio)-3H-xanthen-9-yl)-5-((3-(2,5-dioxo-2,5-dihydro-1H-pyrrol-1-yl)propyl)carbamoyl)benzoate (TAMRA-maleimide)

To a solution of TAMRA-5'-COOH (1 eq., 71.5 mg, 0.166 mmol) in DMF (3.21 mL), TEA (2.5 eq., 57.7 µL, 0.415 mmol) and HATU (1.12 eq., 70.7 mg, 0.186 mmol) here added. Obtained reaction mass was stirred for another 5 minutes and B-2 (1 eq., 71.5 mg, 0.166 mmol) was added. Stirring continued for 25 minutes and the reaction mass was evaporated under reduced pressure to the volume of about 1 mL, and the reaction mass was purified by preparative HPLC to give TAMRA-Maleimide (B-1, 34.8 mg, 0.0615 mmol, 37%) as a pink solid.

$^1$H NMR (400 MHz, METHANOL-$d_4$) δ 8.66 (d, J=1.8 Hz, 1H), 8.14 (dd, J=1.8, 8.0 Hz, 2H), 7.41 (d, J=8.0 Hz, 2H), 7.02 (d, J=9.5 Hz, 1H), 6.92 (dd, J=9.5, 2.2 Hz, 2H), 6.81 (d, J=2.2 Hz, 2H), 6.72 (s, 2H), 3.52 (t, J=6.8 Hz, 2H), 3.34 (t, J=7.0 Hz, 2H), 3.17 (s, 12H), 1.80-1.90 (m, 2H); $^{13}$C NMR (101 MHz, METHANOL-$d_4$) δ 172.5, 168.2, 167.4, 160.6, 159.0, 158.9, 138.1, 137.7, 137.6, 135.5, 132.9, 132.3, 132.0, 131.4, 115.6, 114.8, 97.5, 82.4, 41.0, 38.6, 36.4, 29.3. HR-ESI-MS: $C_{32}H_{30}N_4O_6$, 566.21653. found 566.21654.

B: 5-((3-(3-((2-(4-((4-((E)-(2,5-Dimethoxy-4-((E)-(4-nitro-phenyl)diazenyl)phenyl)diazenyl)phenyl)(methyl)amino)butanamido)ethyl)thio)-2,5-dioxopyrrolidin-1-yl)propyl)carbamoyl)-2-(6-(dimethylamino)-3-(dimethyliminio)-3H-xanthen-9-yl)benzoate To a degased solution of BHQ-SH (1.15 eq., 4.6 mg, 0.00812 mmol) in DCM (0.5 mL), a degased solution of TAMRA-Maleimide (B-1) (1 eq., 4 mg, 0.00313 mmol) in methanol (0.5 mL) was added. TEA (5 eq., 5 µL, 0.0353 mmol) was added and the obtained reaction mass was left overnight at 25° C. Solvents were evaporated; the crude product was solubilized in DMSO (0.5 mL) and purified by HPLC to give B (7 mg, 0.00621 mmol, 88%) as dark-violet solid.

$^1$H NMR (400 MHz, DMSO-$d_6$) δ 8.91 (t, J=6.1 Hz, 1H), 8.68 (s, 1H), 8.43 (d, J=9.1 Hz, 2H), 8.31 (d, J=8.9 Hz, 1H), 8.01-8.10 (m, 3H), 7.77 (d, J=9.1 Hz, 2H), 7.60 (d, J=7.8 Hz, 1H), 7.39 (s, 1H), 7.33 (s, 1H), 6.99 (s, 3H), 6.89 (s, 1H), 6.85 (d, J=9.1 Hz, 2H), 4.04 (dd, J=3.9, 8.9 Hz, 1H), 3.98 (s, 3H), 3.92 (s, 3H), 3.41-3.45 (m, 2H), 3.27-3.38 (m, 6H), 3.23 (m, 12H), 3.06 (s, 3H), 2.85-2.95 (m, 1H), 2.72-2.81 (m, 1H), 2.52-2.56 (m, 2H), 2.17 (t, J=7.3 Hz, 2H), 1.74-1.88 (m, 4H). HR-ESI-MS: $C_{59}H_{62}N_{11}O_{11}S^+$ $[M+H]^+$, 1132.43455. found 1132.43384.

Example 2

Labeling of a Cysteine Derivative with Compounds of the Invention

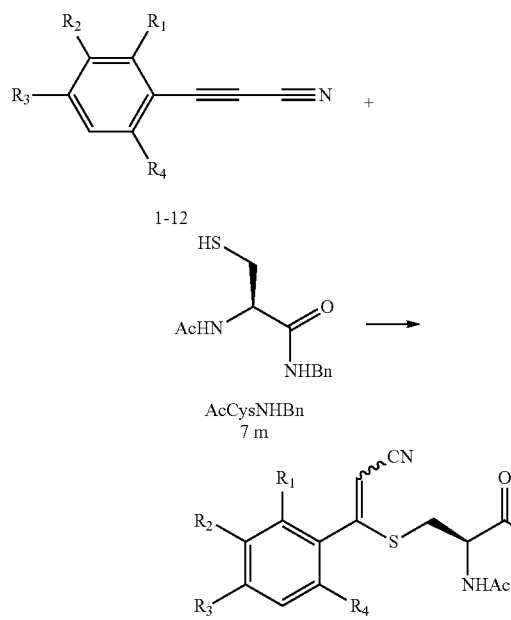

General Procedure

To a vial containing 985 μL of PBS (1×, pH 7.6), were subsequently added 5 μL of the stock solution of benzamide (10 mM in water), 5 μL of the stock solution of arylpropiolonitrile (1-12, 10 mM in DMSO) and 5 μL of stock solution of AcCysNHBn (7m, 10 mM in DMSO). Aliquots of the reaction mixture (50 μL) were analyzed by HPLC (injection at 0 and 30 minutes of reaction). Areas under the peaks of the starting materials and hydrolysis products were normalized according to the area of the peak of the internal standard.

Results

Obtained results are summed up in table 2 below, which presents the conversion of the compounds 1-12 in 30 minutes in presence of 7m at 50 μM concentration of each reagent and 25° C. The reaction is extremely sensitive to steric hindrances induced by substituents in ortho-position to propiolonitrile group (entries 1, 5, 8-9, 4) as well as to electronic effect of the substituent: -I and -M substituents increase (entries 10 and 12), while +M substituents decrease the reactivity of the compound (entries 3 and 7).

TABLE 2

| compound | | Conversion | compound | | Conversion |
|---|---|---|---|---|---|
| 1 | o-OMe | 10.1% | 10 | o-NO$_2$ | 70.4%* |
| 2 | m-OMe | 46.8% | 12 | p-CONHMe | 85.5% |
| 3 | p-OMe | 14.6% | 11 | p-NHAc | 52.3% |

TABLE 2-continued

| compound | | Conversion | compound | | Conversion |
|---|---|---|---|---|---|
| 5 | o-NH$_2$ | 10.8% | 8 | o-Me | 10.3% |
| 6 | m-NH$_2$ | 42.0% | 9 | o,o'-diMe | 2.3%** |
| 7 | p-NH$_2$ | 7.4% | 4 | o,o'-diOMe | 4.8%** |

*Byproducts were observed;
**conversion in 60 minutes.

Example 3

Hydrolytic Stability of a Compound of Formula (I) and Comparison with Phenylmaleimide To a vial containing 980 μL of PBS (1×, pH 7.6), were subsequently added 10 μL of a stock solution of benzamide and 10 μL of a stock solution of electrophile (phenylmaleimide 1 or

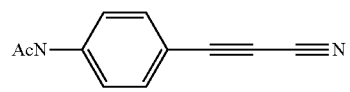

11) to give final concentration of 1 mM (both internal standard and electrophile). Aliquots of the reaction mixture (50 μL) were analyzed by HPLC for 5 hours of hydrolysis (injection every 30 min). Areas under the peaks of the starting materials and hydrolysis products were normalized according to the area of the peak of the internal standard.

The obtained results are presented in FIGS. 4 and 5. Noticeable hydrolysis was observed only for phenylmaleimide 1 (PhMal, $k_{obs}=7\times10^{-5}s^{-1}$). 11 showed no detectable change in concentration.

Example 4

Stability of Compounds of Formula (III)

Stability of the following compound in different conditions

A 100 mM stock solution of the "addition product"

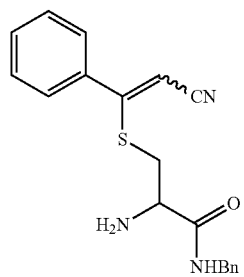

was prepared in DMSO and stored at −20° C. 1 μL of the stock solution was added to 999 μL of working solutions to give 100 μM final concentration of substrate. Aliquots were analyzed at 0, 30 and 60 min. Areas under peak of starting material were normalized according to the area of the peak of the internal standard (benzamide). All measurements were carried at 25° C.

Table 3 below shows the conversion of "the addition product" in different media in one hour.

TABLE 3

| # | Working solution | Conversion of "addition product" in 1 h |
|---|---|---|
| A | 100 mM PhSH in PBS(7.4):DMSO = 80:20 | 0.7% |
| B | 1M H2O2 | 1.8% |
| C | 1M HCl (pH = 0) | 0.1% |
| D | 1M NaOH (pH = 14) | 3.4% |
| E | 1M Glutathione reduced (GSH) in PBS (7.4) | 0.4% |
| F | 1M Imidazole in PBS (7.4) | 0.5% |

This experiment clearly show that the addition product is stable and undergoes very little degradation in a wide range of conditions, in particular for pH ranging from 0 to 14.

In addition, hardly any thiol exchange is observed when the addition product is exposed for 1 hour to a medium comprising an excess of another thiol, such as phenylthiol or glutathione.

Stability of a compound of formula (III) and comparison with maleimide

The stability of compounds A (according to the invention) and B (reference compound) below was studied in different biological conditions.

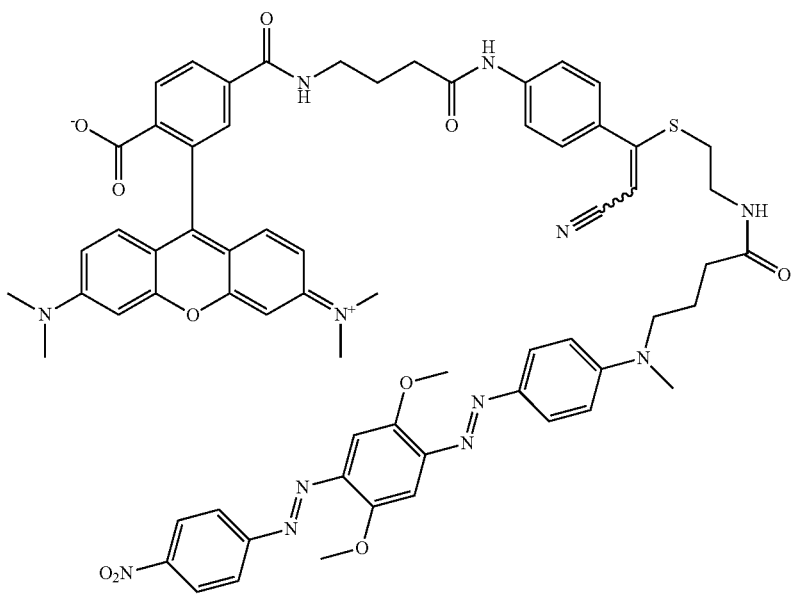

A

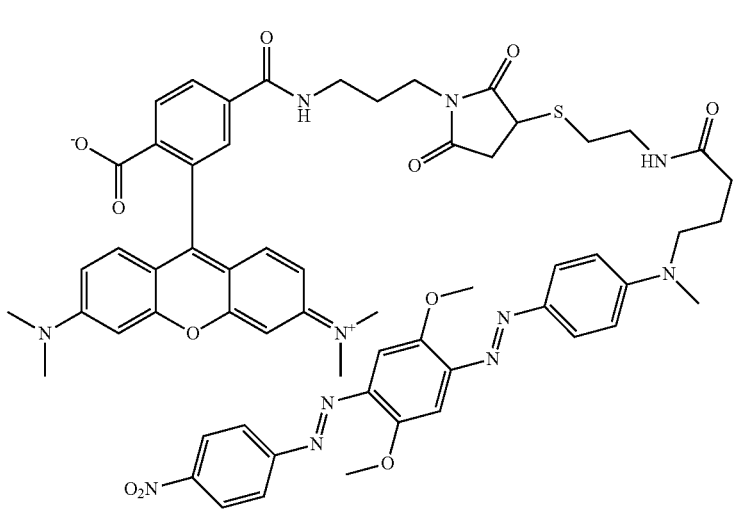

B

Cell Culture:

Normal liver BNL CL.2 cells from mouse were grown in Dulbecco's MEM medium with 1 g/l glucose (Eurobio, Les Ulis, France) supplemented with 10% fetal bovine serum (Perbio, Brebieres, France), 2 mM L-Glutamine, 100 U/mL penicillin, 100 µg/mL streptomycin (Eurobio). Cells were maintained in a 5% $CO_2$ humidified atmosphere at 37° C.

Microscopy:

Twenty four hours prior to experiment, $2.5 \times 10^4$ BNL CL.2 cells were seeded per well in 8-well Lab-Tek II Chambered coverglass plates (ref 155409, Nunc, Naperville, Ill., USA). The required amounts of probes A and B were diluted up to 300 µl in MEM complete medium to give final concentration of 1 µM and then added onto the cells. A 5 µg/ml of Hoechst 118 solution was used as a nuclear marker. Cells were observed with a confocal Leica TSC SPE II microscope after washing with 10% FBS red phenol free Eagle's MEM medium.

Cytometry:

The day before experiment, BNL CL.2 cells were seeded in 96-plates (Greiner Bio One, Frickenhausen, Germany) at $2.0 \times 10^4$ cells/well in Dulbecco's MEM complete medium. Both probes (A and B) were prepared at 1 µM concentrations in Dulbecco's MEM complete and added onto cells during different times (2, 6 and 24 hours). After washing with PBS (Eurobio), 5 min incubation with 40 µl trypsine, and addition of 160 µl of PBS EDTA 5 mM, cells were analyzed by flow cytometry on a PCA-96 Guava cytometer (Guava Technologies Merck Millipore, Billerica, Mass., USA) with a green laser.

First, compound A was far more stable than compound B in human plasma (see FIG. 1).

Figure 2C:
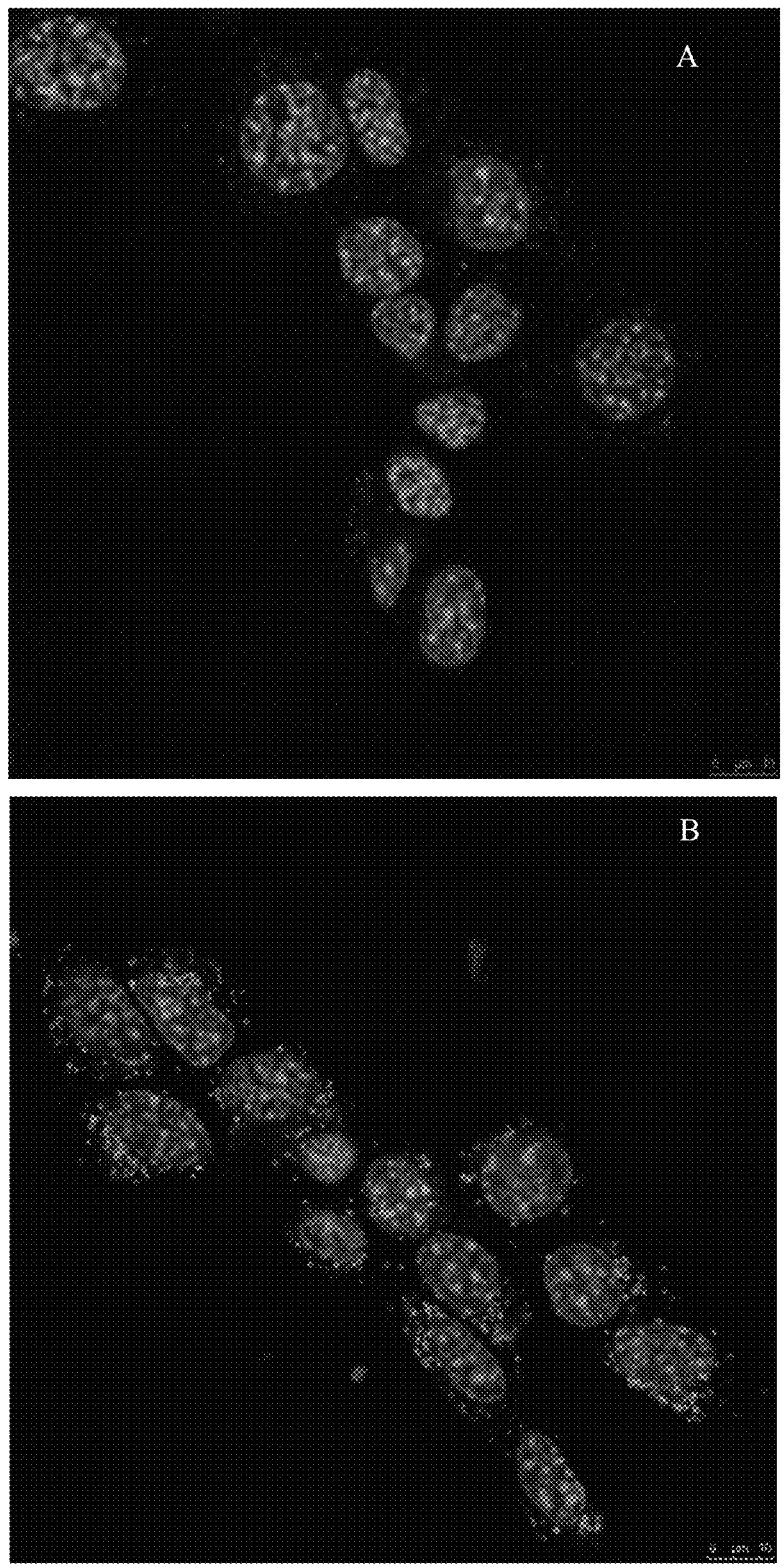
Figure 3A:
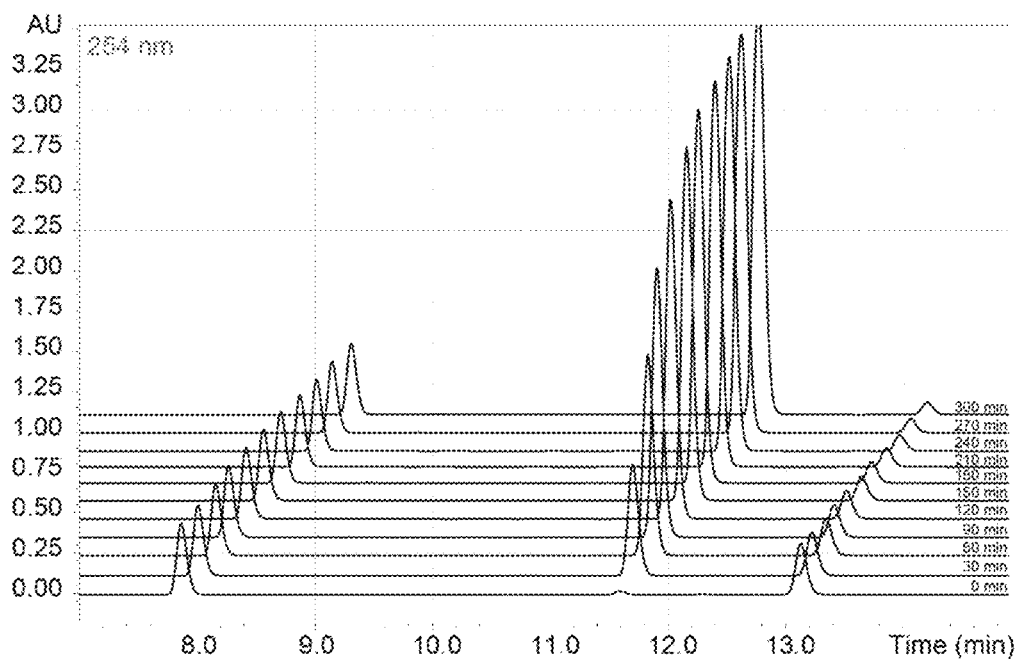
Figure 3B:
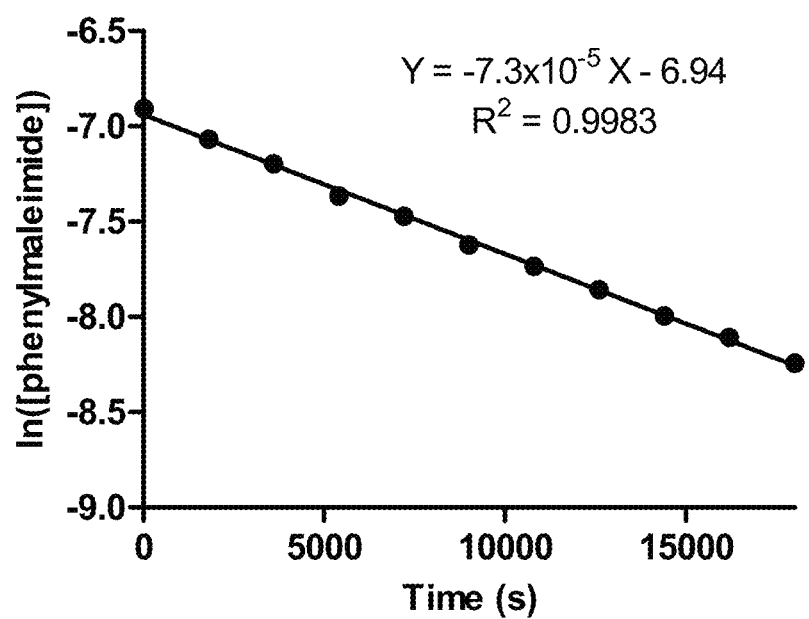

Second, compound A was far more stable than compound B in cellulo (see FIG. 2).

Example 4

Selectivity of Compounds of the Invention Towards the Thiol Moiety

Screening for selectivity was done on benzylamides of non-protected amino acids. 100 mM stock solutions of benzylamides of amino acids (in form of TFA salts) and electrophiles (phenylpropiolonitrile and phenylmaleimide) were prepared in DMSO and stored at −20° C. A 100 mM stock solution of benzamide (used as an internal standard) was prepared in distilled water and stocked at −20° C. Analyses of reaction mixtures were conducted with Shimadzu LC with SunFire™ C18 5 µM 4.6×150 mm column (Waters). HPLC parameters were as follows: flow rate 1 mL/min, gradient from 5 to 95% of mobile phase B from 0 to 20 min, followed by 5 min at 95% of mobile phase and post time of 5 min. Mobile phase A was 0.05% TFA in water (mQ) (v/v), and mobile phase B was acetonitrile (HPLC grade). Data were analyzed using Shimadzu analysis software. Signals were normalized according to the area of the peak of the internal standard (benzamide). Areas under the peaks of the amino acid benzylamides were used to calculate their conversion during reaction.

10 µL of the stock solution of amino acid benzamide and 2.5 µL of the stock solution of benzamide were added to a vial containing 977.5 µL of PBS (1×, pH 7.6). The solution was stirred and 10 µL of the stock solution of electrophile were added to give 1 mM final concentrations of reagents and 0.25 mM concentration of benzamide. Aliquots of the reaction mixture (50 µL) were analyzed by HPLC for 1 hour of hydrolysis (injections at 0, 30 and 60 min). Areas under the peaks of the starting materials and hydrolysis products were normalized according to the area of peak of the internal standard. In case of phenylpropiolonitrile, none of amino acid models gave more than 1.6% conversion (see table 3 below). Conversely, when phenylmaleimide was tested, some amino acid benzylamides showed conversions up to 8.5%. Masses of corresponding adducts were detected by mass spectrometry (ESI-LCMS) in some cases (shown in bold, Table 4).

Table 4 below presents the conversion of benzylamides in 1 hour in PBS (1×, pH 7.6) in presence of phenylpropiolonitrile (1).

TABLE 4

| Amino acid benzamide | Conversion |
|---|---|
| CysNHBn (7a) | 98% |
| GlyNHBn (7b) | 0.2% |
| AlaNHBn (7c) | 0.1% |
| ValNHBn (7d) | 0.7% |
| SerNHBn (7e) | 0.3% |
| MetNHBn (7f) | 0.1% |
| TyrNHBn (7g) | 1.6% |
| HisNHBn (7h) | 0.6% |
| GlnNHBn (7i) | 0.1% |
| TrpNHBn (7j) | 1.3% |
| ArgNHBn (7k) | 0.4% |
| AspNHBn (7l) | 0.6% |

Table 5 below presents the conversion of benzylamides in 1 hour in PBS (1×, pH 7.6) in presence of phenylmaleimide. Bold values correspond to those for which the mass of the corresponding adduct was detected by ESI-LCMS.

TABLE 5

| Amino acid benzamide | Conversion |
|---|---|
| CysNHBn (7a) | 100% |
| GlyNHBn (7b) | 3.3% |
| AlaNHBn (7c) | 0.2% |
| ValNHBn (7d) | 0.9% |
| SerNHBn (7e) | 2.8% |
| MetNHBn (7f) | 1.9% |
| TyrNHBn (7g) | 2.4% |
| HisNHBn (7h) | 8.5% |
| GlnNHBn (7i) | 1.7% |
| TrpNHBn (7j) | 1.0% |
| ArgNHBn (7k) | 2.9% |
| AspNHBn (7l) | 1.3% |

In conclusion, the selectivity of compounds of the invention towards the thiol moiety when compared to other moieties is clearly higher than the selectivity obtained for corresponding compounds, wherein the propiolonitrile moiety is replaced with a maleimide moiety.

Example 5

Toxicity Tests

Toxicity of the following "linker" compounds of formula (II) was studied by MTT assay on HaCaT cell lines:

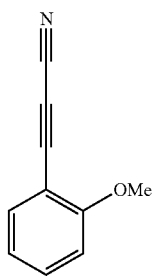

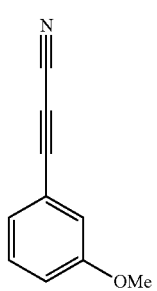

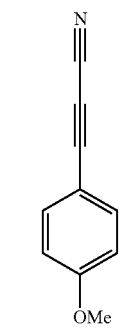

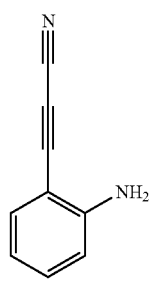

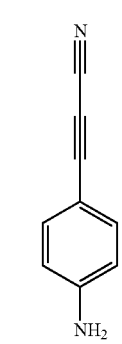

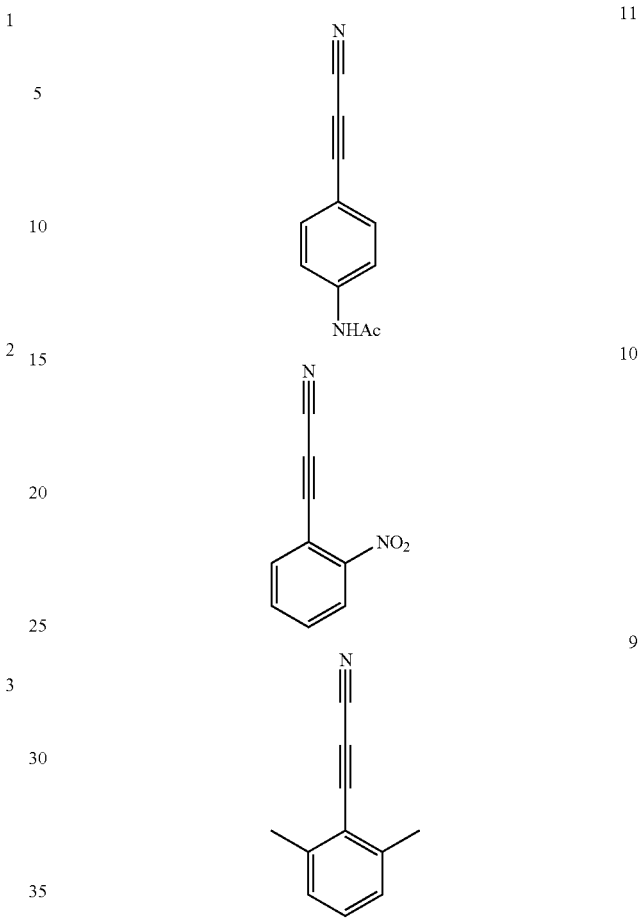

In vitro cytotoxicity was measured using an MTT (3-(4, 5-Dimethylthiazol-2-yl)-2,5-diphenyltetrazolium bromide) assay. The experiments were performed in 96-well plates with HaCaT cells grown to confluence in cell culture media (RPMI 1640 media supplemented with 10% fetal calf serum and 1 mM Glutamin, 200 μL per well). Cells were incubated with chemical reagent at different concentrations (100 μM to 0.78 μM by serial ½ dilutions) at 37° C. for 24 hours. After incubation, the supernatant was replaced with fresh culture media containing MTT (300 μg/mL). After 2 hours of incubation at 37° C., the media was carefully removed and 100 μL of DMSO were added to dissolve the formazan crystals generated by mitochondrial enzymes-induced reduction of the MTT. The absorbance was measured at 595 nm using a microplate reader (Biotek, Synergy HT). The cell viabilities were expressed as percent of untreated control cells.

The results of the MTT test are presented on FIG. 5, and clearly show that compounds of formula (II) are not toxic and may thus be used for instance for biological applications.

Example 6

Labeling of Lysozyme with a Compound of Formula (I)

Labeling of Tryptic Digest of Lysozyme 1 nmol of lysozyme was solubilized in NH$_4$HCO$_3$ (25 mM) and reduced with 1 mM of TCEP at 57° C. during 1 hour. A solution of APN-TMPP (1 mM in DMSO) was added to the protein at a molar ratio of 1:200. Then, labeled protein was subjected to proteolysis by porcine trypsin (Promega V5111). Sample was digested with 1:100 (w/w) trypsin in 25 mM ammonium bicarbonate at 35° C. overnight. NanoLC-MS/MS analyses were performed to follow the reaction. The resulting peptide mixtures were analyzed by C18 reversed phase nanoHPLC on a nanoACQUITY Ultra-Performance-LC system (Waters, Milford, Mass.) coupled to a Q-TOF maXis (Bruker Daltonics, Bremen, Germany) mass spectrometer equipped with a nano-electrospray source. Chromatographic separation was performed on a nanoACQUITY Ultra-Performance-LC. The peptides were separated on an ACQUITY UPLC® BEH130 C18 column (Waters Corp.), 75 μm×200 mm, 1.7 μm particle size. The solvent system consisted of 0.1% formic acid in water (solvent A) and 0.1% formic acid in acetonitrile (solvent B). Trapping was performed on a 20×0.18 mm, 5 μm Symmetry C18 pre-column (Waters Corp.) during 3 minutes at 5 μL/min with 99% of solvent A and 1% of solvent B. Elution was performed at a flow rate of 300 nL/min, using a 1-50% gradient of solvent B for 30 minutes at 50° C. followed by a fast rise at 80% (5 minutes) of solvent B. The complete system was fully controlled by Hystar 3.2 (Bruker Daltonics). The Q-TOF instrument was operated with the following settings: source temperature was set to 200° C., drying gaz flow was 4 l/h, and the nano-electrospray voltage was 4 kV. Mass calibration of the TOF was achieved using ES-TOF Tuning Mix (Agilent Technologies) on the 50 to 2200 m/z range in positive mode. For tandem MS experiments, the system was operated with automatic switching between MS and MS/MS modes both on m/z range [50-2200]. In MS the summation time was 0.2 s. In MS/MS summation time was weighted between 0.2 s and 1.4 s in function of parent ion intensity. The 2 most abundant peptides (intensity threshold 400 au), preferably ions with two, three, four or five charges, were selected on each MS spectrum for further isolation and CID fragmentation with 2 energies set using collision energy profile. Fragmentation was performed using argon as the collision gas. Tryptic peptides were manually sequenced (de novo) to confirm their sequence and locate the cysteine tagged by the APN-TMPP probe. The peptides were identified using extracted ion chromatograms (EIC) based on monoisotopic mass of calculated peptide sequences.

Evaluation of APN-TMPP chemoselectivity was carried by studying of its reaction with tryptic digest at 200:1 molar ratio of APN-TMPP (1 μM) to protein (around 10:1 to cysteine moieties) at room temperature for one hour. Peptide mixtures obtained without and with chemical derivatization were analyzed by LC-MS/MS. All detectable cysteine-containing peptides reacted with a probe and were delayed while cysteine-free peptides were unaffected. The labeling efficiency was evaluated based on the ratio between intensities of labeled and non-labeled peptides by LC-MS. More than 98% of the detected peptides were completely labeled. LC-MS results show clearly that cysteine-containing peptides have an increased retention time due to the addition of the hydrophobic TMPP group, whereas the retention time of all other peptides was unchanged (Table 6).

Table 6 below shows the results of LC-MS analyses of tryptic digest of lysozyme before and after reaction with APN-TMPP.

TABLE 6

| Peptide sequence[a] | Before tagging | | After tagging | | | Number of |
| --- | --- | --- | --- | --- | --- | --- |
| | m/z (charge state) | RT (min) | m/z (charge state) | RT (min) | ΔRT (min) | tags |
| [24]CELAAAMK[31] | 418.70 (+2) | 13.9 | 645.89 (+3) | 24.2 | 10.3 | 1 |
| [24]CELAAAMoxK[31] | 426.70 (+2) | 12.6 | 551.23 (+3) | 23.7 | 11.1 | 1 |
| [40]GYSLGNWVCAAK[51] | 634.81 (+2) | 19.8 | 689.96 (+3) | 25.3 | 5.5 | 1 |
| [80]WWCNDGR[86] | 468.89 (+2) | 16.5 | 679.22 (+3) | 25.7 | 9.2 | 1 |
| [92]NLCNIPCSALLSSDITASVNCAK[114] | 779.71 (+2) | 23.7 | 949.20 (+5) | 30.3 | 6.6 | 3 |
| [52]FESNFNTQATNR[63] | 714.83 (+2) | 13.5 | 714.83 (+2) | 13.5 | 0 | 0 |
| [13]GTDVQAWIR[143] | 523.27 (+2) | 17.3 | 523.27 (+2) | 17.3 | 0 | 0 |
| [64]NTDGSTDYGILQINSR[79] | 585.28 (+2) | 18.2 | 585.28 (+2) | 18.2 | 0 | 0 |
| [118]IVSDGNGMNAWVAWR[130] | 559.27 (+2) | 20.9 | 559.27 (+2) | 20.9 | 0 | 0 |

[a]Cysteine residues are in bold.

Example 7

Conjugation of Solubilizating APN Reagents (49-54) with CD38 A275C Mutant

General scheme of the experiment (on the example of modification of CD38 mutant with 49) is illustrated on FIG. 6.

To 300 μL of CD38C275 solution (1 mg/mL) was added 6 μL of 50 mM solution of solubilizing APN reagent (49-54) in DMSO. In parallel, as a control, to 300 μL of CD38C275 was added 6 μL of DMSO. Both samples were incubated for 15 hours at 25° C., then dialyzed 5 times (membrane cut off of 10k) to give final volume of 30 μL each (10 mg/mL). Size of aggregates was measured by DLS.

Example 8

Labeling of CD38-CD375 Mutant and Comparison with Maleimide a) Stability of the Compound of the Invention and of the Corresponding Maleimide The compounds below were synthesized:

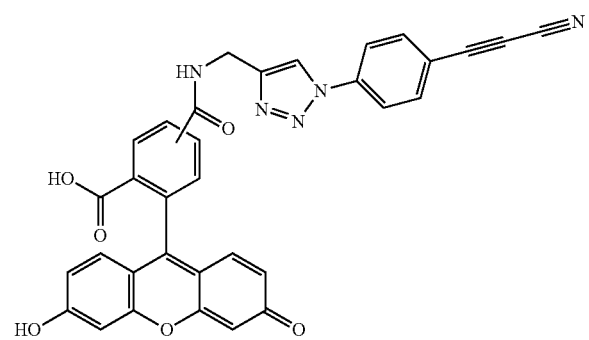

-continued

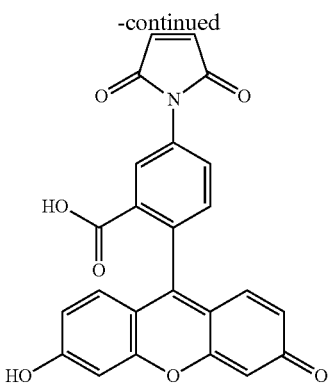

Stability studies proved that the compound according to the invention was stable for 24 hours in PBS (Phosphate Buffer Saline). Comparatively, the corresponding compound comprising a maleimide moiety was 70% degraded after one hour in PBS.

b) Reaction with the CD38 Mutant

Both compounds were reacted with a 2 μM solution of the CD38-C375 mutant.

Gel electrophoresis after purification showed that a higher labeling rate could be obtained with the compounds according to the invention than with the corresponding maleimide compound. FIG. 7 presents the gel electrophoresis obtained with the compound of the invention and the maleimide, before and after purification.

Example 9

Conjugation of Trastuzumab and TAMRA Using Compound 18

General scheme of the experiment is illustrated on FIG. 8.

To the solution of Trastuzumab (100 uL, 10 mg/mL in 50 mM borate buffer pH 8.5) was added 1.74 uL of the solution of 18 (10 mg/mL in DMSO). After incubation for 1 h at 25° C. was added 0.69 uL of TAMRA-SH (100 mM in DMSO). The mixture was incubated at 25° C. for 16 h and the conjugate was purified by size exclusion chromatography.

The comparison experiment was carried out using 4-(N-maleimidomethyl)cyclohexanecarboxylic acid N-hydroxysuccinimide ester (SMCC) instead of 18.

SDS-PAGE analysis of the obtained conjugates (FIG. 9) showed that compound 18 allows for higher levels of conjugation comparing to SMCC.

Native ESI-MS analysis of the conjugate prepared using 18 (FIG. 10, FIG. 11) showed that in average one molecule of TAMRA per antibody was conjugated.

Native ESI-MS analysis of the conjugate prepared using SMCC (FIG. 12, FIG. 13) showed a complex mixture of undistinguishable species.

Experiment shows that the compound 18 allows for higher levels of conjugation and gives cleaner population of conjugates comparing to generally applied SMCC.

Example 10

Direct Conjugation of the Compound 58 to Partially Reduced Trastuzumab

General scheme of the experiment is illustrated on FIG. 14.

To the solution of Trastuzumab (100 uL, 10 mg/mL in 50 mM PBS pH 7.4 with 10 mM of EDTA) was added the solution of TCEP (10 mM in water, 1.1 or 2.2 eq.). The mixture was incubated at 37° C. for 2 h and then the solution of 58 (8.25 μL, 10 mM in DMSO) was added. The mixture was incubated at 25° C. for 16 h and the conjugate was purified by size exclusion chromatography.

SDS-PAGE analysis of the obtained conjugates (FIG. 15) showed that compound 58 was covalently attached to the antibody. ESI-MS analysis showed that in average 4 molecules were conjugated per antibody using 2.2 eq. of TCEP.

Example 11

Rebridging of Antibody Fragments Using Compounds 33 and 34

Figure 16:
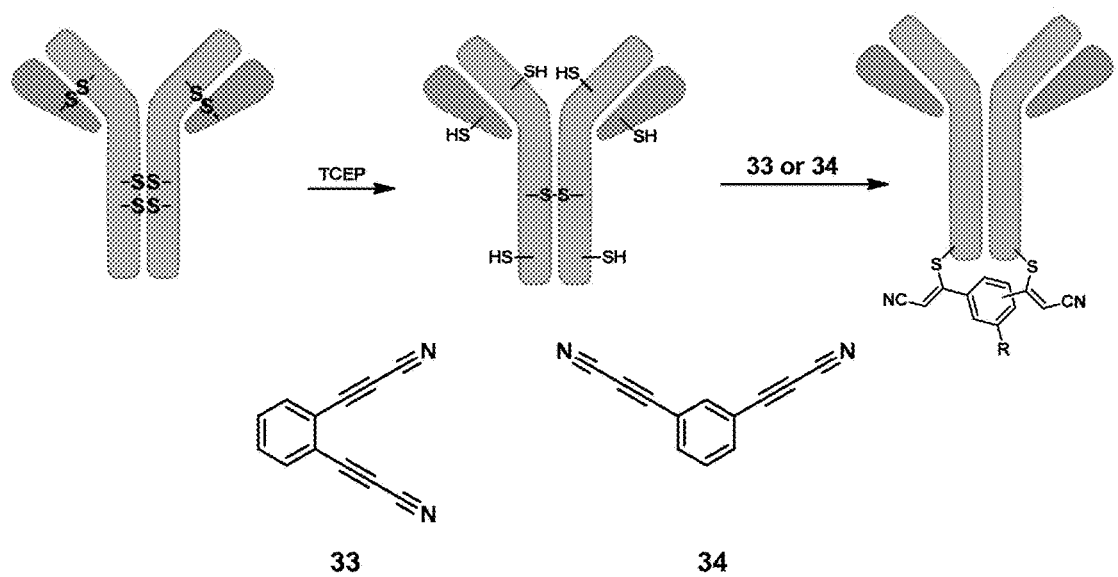

General scheme of the experiment is illustrated on FIG. 16.

To the solution of Trastuzumab (100 uL, 10 mg/mL in 50 mM PBS pH 7.4 with 10 mM of EDTA) was added the solution of TCEP (10 mM in water, 5 eq.). The mixture was incubated at 37° C. for 2 h and then the solution of 33 or 34 (10 mM in DMSO, 15 eq.) was added. The resulting solution was incubated for 16 h at 25° C. and then analyzed by SDS-PAGE in reducing conditions.

SDS-PAGE analysis showed that antibody fragments were successfully bridged by compounds 33 and 34 (FIG. 17).

We claim:

1. A process for the conjugation of a protein comprising at least one cysteine residue having a thiol moiety, the process comprising contacting the protein with a compound of formula (I):

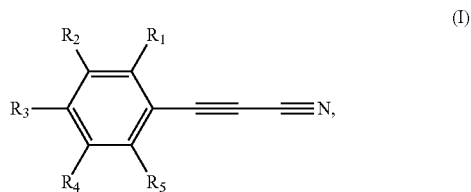

wherein each of $R_1$, $R_2$, $R_4$ and $R_5$ is hydrogen, and
wherein $R_3$ is selected from the group consisting of an antibody, a drug and a fluorescent probe bonded to the phenyl ring of the compound of formula (I), optionally through a linker group.

2. The process of claim 1, wherein the linker group is COO, NH—C(=O)—NH, NH—C(=O)—O, a triazole or CONH.

* * * * *

UNITED STATES PATENT AND TRADEMARK OFFICE
CERTIFICATE OF CORRECTION

PATENT NO. : 10,131,626 B2
APPLICATION NO. : 15/480420
DATED : November 20, 2018
INVENTOR(S) : Alain Wagner and Oleksandr Koniev Page 1 of 1

It is certified that error appears in the above-identified patent and that said Letters Patent is hereby corrected as shown below:

In the Specification

Column 83,
Line 35, "$C_{18}H_{16}N_3O_{5+}$" should read --$C_{18}H_{16}N_3O_5^+$--.

Column 95,
Line 32, "of a 5 solution" should read --of a solution--.

Column 98,
Lines 9-15, " 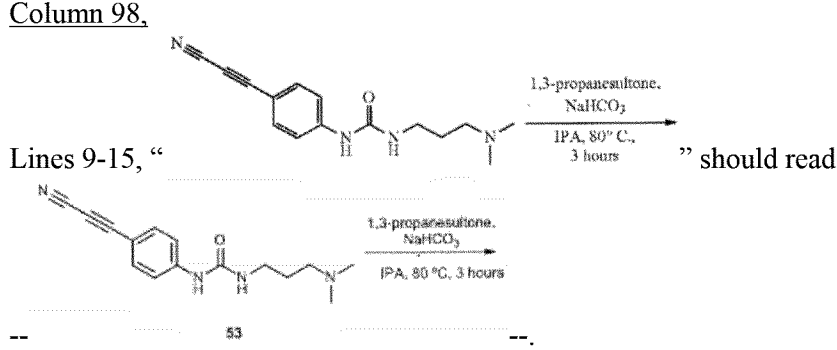 " should read -- -- .

Column 123,
Line 24, "$^{13}$GTDVQAWIR$^{143}$" should read --$^{135}$GTDVQAWIR$^{143}$--.

Column 124,
Line 18, "645.89 (+3)" should read --545.89 (+3)--.

Column 124,
Line 22, "679.22 (+3)" should read --579.22 (+3)--.

Signed and Sealed this
Twenty-fourth Day of September, 2019

Andrei Iancu
*Director of the United States Patent and Trademark Office*